United States Patent
Chen et al.

(10) Patent No.: US 7,056,685 B1
(45) Date of Patent: Jun. 6, 2006

(54) RECEPTOR LIGANDS AND METHODS OF MODULATING RECEPTORS

(75) Inventors: Jin-Long Chen, San Mateo, CA (US); Lei Ling, Foster City, CA (US); Hui Tian, Foster City, CA (US)

(73) Assignee: Amgen Inc., Thousands Oaks, CA (US)

( * ) Notice: Subject to any disclaimer, the term of this patent is extended or adjusted under 35 U.S.C. 154(b) by 0 days.

(21) Appl. No.: 10/703,145

(22) Filed: Nov. 5, 2003

Related U.S. Application Data

(60) Provisional application No. 60/424,093, filed on Nov. 5, 2002.

(51) Int. Cl.
  *G01N 33/53* (2006.01)
  *G01N 33/00* (2006.01)
  *C12P 21/06* (2006.01)
  *C07K 14/00* (2006.01)

(52) U.S. Cl. .................... 435/7.1; 435/7.93; 435/69.1; 530/350; 436/129

(58) Field of Classification Search ............... 530/350, 530/300; 435/6, 7.1, 7.93, 7.95; 436/129; 35/69.1
See application file for complete search history.

(56) References Cited

U.S. PATENT DOCUMENTS

| | | | |
|---|---|---|---|
| 5,436,128 A | 7/1995 | Harpold et al. | |
| 5,714,566 A | 2/1998 | Lubowtiz et al. | |
| 5,871,963 A | 2/1999 | Conley et al. | |
| 5,910,430 A | 6/1999 | Bergsma et al. | |
| 6,008,322 A | 12/1999 | Kuestner et al. | |
| 6,063,582 A | 5/2000 | Conley et al. | |
| 6,448,230 B1 | 9/2002 | Ruben et al. | |
| 6,555,339 B1 | 4/2003 | Liaw et al. | |
| 6,680,373 B1 | 1/2004 | Conley et al. | |
| 2002/0042372 A1 | 4/2002 | Olsen et al. | |
| 2002/0137887 A1 | 9/2002 | Hedrick et al. | |
| 2004/0019109 A1 | 1/2004 | Owman et al. | |

FOREIGN PATENT DOCUMENTS

| | | |
|---|---|---|
| DE | 10046970 A1 | 4/2002 |
| EP | 853126 A2 | 7/1998 |
| EP | 859053 A1 | 8/1998 |
| EP | 1094076 A1 | 4/2001 |
| EP | 1178053 A2 | 2/2002 |
| GB | 2365012 A | 2/2002 |
| GB | 2369364 A | 5/2002 |
| GB | 1219638 A2 | 7/2002 |
| JP | 10304887 | 11/1998 |
| WO | WO 95/24411 A1 | 9/1995 |
| WO | WO 97/20045 A2 | 6/1997 |
| WO | WO 97/24929 A1 | 7/1997 |
| WO | WO 98/40483 A2 | 9/1998 |
| WO | WO 99/15858 A2 | 4/1999 |
| WO | WO 00/14229 A1 | 3/2000 |
| WO | WO 00/22129 A1 | 4/2000 |

(Continued)

OTHER PUBLICATIONS see Bowie et. al., Science 247: 1306-1310, 1990.*

(Continued)

*Primary Examiner*—Eileen B. O'Hara
(74) *Attorney, Agent, or Firm*—Banner & Witcoff, Ltd.

(57) ABSTRACT

The invention provides natural ligands of various receptors and methods of identifying modulators of various receptors using the ligands. Methods of using the modulators to treat diseases or disorder associated with dysfunction of the receptor are also provided.

5 Claims, 10 Drawing Sheets

β–Alanine Dose Dependence of TGR2 in CHO Cells

FOREIGN PATENT DOCUMENTS

| | | |
|---|---|---|
| WO | WO 00/22131 A2 | 4/2000 |
| WO | WO 00/31258 A2 | 6/2000 |
| WO | WO 00/61628 A1 | 10/2000 |
| WO | WO 01/36471 A2 | 5/2001 |
| WO | WO 01/36473 A2 | 5/2001 |
| WO | WO 01/48188 A1 | 7/2001 |
| WO | WO 01/48189 A1 | 7/2001 |
| WO | WO 01/49847 A2 | 7/2001 |
| WO | WO 01/55338 A2 | 8/2001 |
| WO | WO 01/57085 A2 | 8/2001 |
| WO | WO 01/57190 A2 | 8/2001 |
| WO | WO 01/61359 A2 | 8/2001 |
| WO | WO 01/62797 A2 | 8/2001 |
| WO | WO 01/68750 A2 | 9/2001 |
| WO | WO 01/70814 A2 | 9/2001 |
| WO | WO 01/79449 A2 | 10/2001 |
| WO | WO 01/83555 A2 | 11/2001 |
| WO | WO 01/83748 A1 | 11/2001 |
| WO | WO 01/87937 A2 | 11/2001 |
| WO | WO 01/87980 A2 | 11/2001 |
| WO | WO 01/90304 A2 | 11/2001 |
| WO | WO 01/98330 A2 | 12/2001 |
| WO | WO 01/98351 A2 | 12/2001 |
| WO | WO 02/00719 A2 | 1/2002 |
| WO | WO 02/14511 A2 | 2/2002 |
| WO | WO 02/16548 A2 | 2/2002 |
| WO | WO 02/46414 A2 | 6/2002 |
| WO | WO 02/53737 A1 | 7/2002 |
| WO | WO 02/55702 A2 | 7/2002 |
| WO | WO 02/57441 A1 | 7/2002 |
| WO | WO 02/57452 A2 | 7/2002 |
| WO | WO 02/57783 A2 | 7/2002 |
| WO | WO 02/61087 A2 | 8/2002 |
| WO | WO 02/68591 A2 | 9/2002 |
| WO | WO 02/88183 A2 | 11/2002 |
| WO | WO 03/000893 A2 | 1/2003 |
| WO | WO 03/039443 A2 | 5/2003 |
| WO | WO 03/068959 A1 | 8/2003 |

OTHER PUBLICATIONS

Wells, Biochemistry 29:8509-8517, 1990.*

Altenhofen, W. et al.; "Control of ligand specificity in cyclic nucleotide-gated channels from rod photoreceptors and olfactory epitheilum"; *Proc. Natl. Acad. Sci. USA*; Nov. 1991; 88: 9868-9872.

An, Songzhu et al.; "Identification and characterization of a melanin-concentrating hormone receptor", *Proc. Natl. Acad. Sci. USA*; Jun. 19, 2001; 98(13):7578-7581.

Baldo, Allain et al.; " The Adipsin-Acylation Stimulating Protein System and Regulation of Intracellular Triglyceride Synthesis"; *J. Clin. Invest.*; 1993; 92:1543-1547.

Baldwin et al.; *Baillieres Clin. Endocrinol. Metab.* 1994; 8(1):185-214.

Barak, Larry S. et al.; "Internal Trafficking and Surface Mobility of a Functionality Intact $\beta_2$-Adrenergic Receptor-Green Fluorescent Protein Conjugate"; *Molecular Pharmacology*; 1997; 51:177-184.

Berridge, Michael J. & Robin F. Irvine; "Inositol triphosphate, a novel second messenger in cellular signal transduction"; *Nature*; 1984; 312:315-321.

Buck, Linda & Richard Axel; "A Novel Multigene Family May Encode Odorant Receptors: A Molecular Basis for Odor Recognition"; *Cell*; 1991; 65:175-187.

Chang, Andy C.-M. et al.; "A novel human cDNA highly homologous to the fish hormone stanniocalcin"; *Mol. Cell. Endocrinol.*; 1995; 112:241-247.

Dhallan, Ravinder S. et al.; "Primary structure and functional expression of a cyclic nucleotide-activated channel from olfactory neurons"; *Nature*: 1990; 347:184-187.

Felley-Bosco et al.; *Am. J. Resp. Cell and Mol. Biol.*; 1994; 11:159-164.

Fong, Tung Ming; "Mechanistic Hypotheses for the Activation of G-Protein-Coupled Receptors"; *Cell Signal*; 1996; 8(3):217-224.

Hsu, Sheau Yu et al.; "The Three Subfamilies of Leucine-Rich Repeat-Containing G Protein-Coupled Receptors (LGR): Identification of LGR6 and LGR7 and the Signaling Mechanism for LGR7"; *Molecular Endocrinology*; 2000; 14(8): 1257-1271.

Kyte, Jack & Russell F. Doolitlle; "A Simple Method for Displaying the Hydropathic Character of a Protein"; *J. Mol. Biol.*; 1982; 157:105-132.

Misteli, Tom & David L. Spector; "Applications of the green fluorescent protein in cell biology and biotechnology"; *Nature Biotechnology*; 1997; 15:961-964.

Murray, Ian et al.; "Acylation-stimulating protein (ASP): structure-function determinants of cell surface binding and triacylglycerol synthetic activity"; *Biochem. J.*; 1999; 342:41-48.

Offermanns, Stefan & Melvin I. Simon; "$G\alpha_{15}$ and $G1\alpha_{15}$ Couple a Wide Variety of Receptors to Phospholipase C"; *The Journal of Biological Chemistry*; 1995; 270(25):15175-15180.

Wilkie, Thomas M. et al.; "Characterization of G-protein $\alpha$ subunits in the $G_q$ class: Expression in murine tissues and in stromal and hematopoietic cell lines"; *Proc. Natl. Acad. Sci. USA*; Nov. 1991; 88:10049-10053.

* cited by examiner

Figure 3

| | | EC50 |
|---|---|---|
| ⋏⋏COOH | butyric acid | >1000 uM |
| ⋏⋏⋏COOH | hexanoic acid | 834 uM |
| ⋏⋏⋏⋏COOH | octanoic acid | 117 uM |
| ⋏⋏⋏⋏⋏COOH | decanoic acid | 78 uM |
| ⋏⋏⋏⋏⋏⋏COOH | dodecanoic acid | 43 uM |
| ⋏⋏⋏⋏⋏⋏⋏COOH | tetradecanoic acid | ~40 uM |
| ⋏⋏⋏⋏⋏⋏⋏⋏COOH | hexadecanoic acid | ~40 uM |
| ⋏⋏⋏⋏⋏⋏⋏⋏⋏COOH | Octadecanoic acid | N/D |
| ⋏⋏⋏⋏⋏⋏⋏⋏⋏⋏COOH | Arachidic acid | >1000 uM |

| | | EC50 |
|---|---|---|
|  COOH | Docosatetraaenoic acid | 8.1 uM |
|  COOH | Docosapentaenoic acid | 6.0 uM |
|  COOH | Docosahexaenoic acid | 4.0 uM |
|  COOH | Eicosatetraenoic acid (arachidonic) | 23.1 uM |
|  COOH | Eicosapentaenoic acid | 13.8 uM | succinic acid maleic acid fumaric acid oxalacetic acid methylmalonic acid itaconic acid succinic anhydride succinimide succinic acid semialdehyde alpha keto- glutaric acid itaconic acid succinic acid oxalacetic acid malic acid glutaric acid

SEQUENCE LISTING

<160> NUMBER OF SEQ ID NOS: 19

<210> SEQ ID NO 1
<211> LENGTH: 963
<212> TYPE: DNA
<213> ORGANISM: Homo sapiens
<220> FEATURE:
<223> OTHER INFORMATION: human TGR2 G-protein coupled receptor (GPCR)

<400> SEQUENCE: 1

```
atgaaccaga ctttgaatag cagtgggacc gtggagtcag ccctaaacta ttccagaggg      60
agcacagtgc acacggccta cctggtgctg agctccctgg ccatgttcac ctgcctgtgc     120
gggatggcag gcaacagcat ggtgatctgg ctgctgggct ttcgaatgca caggaacccc     180
ttctgcatct atatcctcaa cctggcggca gccgacctcc tcttcctctt cagcatggct     240
tccacgctca gcctggaaac ccagcccctg gtcaatacca ctgacaaggt ccacgagctg     300
atgaagagac tgatgtactt tgcctacaca gtgggcctga gcctgctgac ggccatcagc     360
acccagcgct gtctctctgt cctcttccct atctggttca agtgtcaccg gcccaggcac     420
ctgtcagcct gggtgtgtgg cctgctgtgg acactctgtc tcctgatgaa cgggttgacc     480
tcttccttct gcagcaagtt cttgaaattc aatgaagatc ggtgcttcag ggtggacatg     540
gtccaggccg ccctcatcat gggggtctta accccagtga tgactctgtc cagcctgacc     600
ctctttgtct gggtgcggag gagctcccag cagtggcggc ggcagcccac acggctgttc     660
gtggtggtcc tggcctctgt cctggtgttc ctcatctgtt ccctgcctct gagcatctac     720
tggtttgtgc tctactggtt gagcctgccg cccgagatgc aggtcctgtg cttcagcttg     780
tcacgcctct cctcgtccgt aagcagcagc gccaaccccg tcatctactt cctggtgggc     840
agccggagga gccacaggct gcccaccagg tccctgggga ctgtgctcca acaggcgctt     900
cgcgaggagc ccgagctgga aggtggggag acgcccaccg tgggcaccaa tgagatgggg     960
gct                                                                   963
```

<210> SEQ ID NO 2
<211> LENGTH: 321
<212> TYPE: PRT
<213> ORGANISM: Homo sapiens
<220> FEATURE:
<223> OTHER INFORMATION: human TGR2 G-protein coupled receptor (GPCR)

<400> SEQUENCE: 2

```
Met Asn Gln Thr Leu Asn Ser Ser Gly Thr Val Glu Ser Ala Leu Asn
  1               5                  10                  15

Tyr Ser Arg Gly Ser Thr Val His Thr Ala Tyr Leu Val Leu Ser Ser
                 20                  25                  30

Leu Ala Met Phe Thr Cys Leu Cys Gly Met Ala Gly Asn Ser Met Val
             35                  40                  45
```

```
Ile Trp Leu Leu Gly Phe Arg Met His Arg Asn Pro Phe Cys Ile Tyr
 50                  55                  60
Ile Leu Asn Leu Ala Ala Asp Leu Leu Phe Leu Phe Ser Met Ala
 65                  70                  75                  80
Ser Thr Leu Ser Leu Glu Thr Gln Pro Leu Val Asn Thr Asp Lys
                 85                  90                  95
Val His Glu Leu Met Lys Arg Leu Met Tyr Phe Ala Tyr Thr Val Gly
                100                 105                 110
Leu Ser Leu Leu Thr Ala Ile Ser Thr Gln Arg Cys Leu Ser Val Leu
                115                 120                 125
Phe Pro Ile Trp Phe Lys Cys His Arg Pro Arg His Leu Ser Ala Trp
130                 135                 140
Val Cys Gly Leu Leu Trp Thr Leu Cys Leu Leu Met Asn Gly Leu Thr
145                 150                 155                 160
Ser Ser Phe Cys Ser Lys Phe Leu Lys Phe Asn Glu Asp Arg Cys Phe
                165                 170                 175
Arg Val Asp Met Val Gln Ala Ala Leu Ile Met Gly Val Leu Thr Pro
                180                 185                 190
Val Met Thr Leu Ser Ser Leu Thr Leu Phe Val Trp Val Arg Arg Ser
                195                 200                 205
Ser Gln Gln Trp Arg Arg Gln Pro Thr Arg Leu Phe Val Val Leu
210                 215                 220
Ala Ser Val Leu Val Phe Leu Ile Cys Ser Leu Pro Leu Ser Ile Tyr
225                 230                 235                 240
Trp Phe Val Leu Tyr Trp Leu Ser Leu Pro Pro Glu Met Gln Val Leu
                245                 250                 255
Cys Phe Ser Leu Ser Arg Leu Ser Ser Ser Val Ser Ser Ser Ala Asn
                260                 265                 270
Pro Val Ile Tyr Phe Leu Val Gly Ser Arg Arg Ser His Arg Leu Pro
                275                 280                 285
Thr Arg Ser Leu Gly Thr Val Leu Gln Gln Ala Leu Arg Glu Glu Pro
290                 295                 300
Glu Leu Glu Gly Gly Glu Thr Pro Thr Val Gly Thr Asn Glu Met Gly
305                 310                 315                 320
Ala

<210> SEQ ID NO 3
<211> LENGTH: 1014
<212> TYPE: DNA
<213> ORGANISM: Homo sapiens
<220> FEATURE:
<223> OTHER INFORMATION: human GPR77 G-protein coupled receptor (GPCR)

<400> SEQUENCE: 3
atggggaacg attctgtcag ctacgagtat gggggattaca gcgacctctc ggaccgccct      60
gtggactgcc tggatggcgc ctgcctggcc atcgacccgc tgcgcgtggc cccgctccca     120
ctgtatgccg ccatcttcct ggtggggggtg ccgggcaatg ccatggtggc ctgggtggct     180
gggaaggtgg cccgccggag ggtgggtgcc acctggttgc tccacctggc cgtggcggat     240
ttgctgtgct gtttgtctct gcccatcctg gcagtgccca ttgcccgtgg aggccactgg     300
ccgtatggtc agtgggctg tcgggcgctg ccctccatca tcctgctgac catgtatgcc     360
agcgtcctgc tcctggcagc tctcagtgcc gacctctgct tcctggctct cgggcctgcc     420
tggtggtcta cggttcagcg ggcgtgcggg gtgcaggtgg cctgtggggc agcctggaca     480
```

| | | |
|---|---|---|
| ctggccttgc tgctcaccgt gccctccgcc atctaccgcc ggctgcacca ggagcacttc | 540 | |
| ccagcccggc tgcagtgtgt ggtggactac ggcggctcct ccagcaccga gaatgcggtg | 600 | |
| actgccatcc ggtttctttt tggcttcctg gggcccctgg tggccgtggc cagctgccac | 660 | |
| agtgccctcc tgtgctgggc agcccgacgc tgccggccgc tgggcacagc cattgtggtg | 720 | |
| gggttttttg tctgctgggc acctaccac ctgctgggc tggtgctcac tgtggcggcc | 780 | |
| ccgaactccg cactcctggc cagggccctg cgggctgaac ccctcatcgt gggccttgcc | 840 | |
| ctcgctcaca gctgcctcaa tcccatgctc ttcctgtatt ttgggagggc tcaactccgc | 900 | |
| cggtcactgc cagctgcctg tcactgggcc ctgaggggag cccagggcca ggacgaaagt | 960 | |
| gtggacagca agaaatccac cagccatgac ctggtctcgg agatggaggt gtag | 1014 | |

<210> SEQ ID NO 4
<211> LENGTH: 337
<212> TYPE: PRT
<213> ORGANISM: Homo sapiens
<220> FEATURE:
<223> OTHER INFORMATION: human GPR77 G-protein coupled receptor (GPCR)

<400> SEQUENCE: 4

```
Met Gly Asn Asp Ser Val Ser Tyr Glu Tyr Gly Asp Tyr Ser Asp Leu
 1               5                  10                  15

Ser Asp Arg Pro Val Asp Cys Leu Asp Gly Ala Cys Leu Ala Ile Asp
             20                  25                  30

Pro Leu Arg Val Ala Pro Leu Pro Leu Tyr Ala Ala Ile Phe Leu Val
         35                  40                  45

Gly Val Pro Gly Asn Ala Met Val Ala Trp Val Ala Gly Lys Val Ala
     50                  55                  60

Arg Arg Arg Val Gly Ala Thr Trp Leu Leu His Leu Ala Val Ala Asp
 65                  70                  75                  80

Leu Leu Cys Cys Leu Ser Leu Pro Ile Leu Ala Val Pro Ile Ala Arg
                 85                  90                  95

Gly Gly His Trp Pro Tyr Gly Ala Val Gly Cys Arg Ala Leu Pro Ser
            100                 105                 110

Ile Ile Leu Leu Thr Met Tyr Ala Ser Val Leu Leu Leu Ala Ala Leu
        115                 120                 125

Ser Ala Asp Leu Cys Phe Leu Ala Leu Gly Pro Ala Trp Trp Ser Thr
    130                 135                 140

Val Gln Arg Ala Cys Gly Val Gln Val Ala Cys Gly Ala Ala Trp Thr
145                 150                 155                 160

Leu Ala Leu Leu Leu Thr Val Pro Ser Ala Ile Tyr Arg Arg Leu His
                165                 170                 175

Gln Glu His Phe Pro Ala Arg Leu Gln Cys Val Val Asp Tyr Gly Gly
            180                 185                 190

Ser Ser Ser Thr Glu Asn Ala Val Thr Ala Ile Arg Phe Leu Phe Gly
        195                 200                 205

Phe Leu Gly Pro Leu Val Ala Val Ala Ser Cys His Ser Ala Leu Leu
    210                 215                 220

Cys Trp Ala Ala Arg Arg Cys Arg Pro Leu Gly Thr Ala Ile Val Val
225                 230                 235                 240

Gly Phe Phe Val Cys Trp Ala Pro Tyr His Leu Leu Gly Leu Val Leu
                245                 250                 255

Thr Val Ala Ala Pro Asn Ser Ala Leu Leu Ala Arg Ala Leu Arg Ala
            260                 265                 270
```

-continued

```
Glu Pro Leu Ile Val Gly Leu Ala Leu Ala His Ser Cys Leu Asn Pro
        275                 280                 285
Met Leu Phe Leu Tyr Phe Gly Arg Ala Gln Leu Arg Arg Ser Leu Pro
    290                 295                 300
Ala Ala Cys His Trp Ala Leu Arg Glu Ser Gln Gly Gln Asp Glu Ser
305                 310                 315                 320
Val Asp Ser Lys Lys Ser Thr Ser His Asp Leu Val Ser Glu Met Glu
                325                 330                 335
Val
```

<210> SEQ ID NO 5
<211> LENGTH: 1935
<212> TYPE: DNA
<213> ORGANISM: Homo sapiens
<220> FEATURE:
<223> OTHER INFORMATION: human LGR4 G-protein coupled receptor (GPCR)

<400> SEQUENCE: 5

```
atggtgcagc agttccccaa tcttacagga actgtccacc tggaaagtct gactttgaca      60
ggtacaaaga taagcagcat acctaataat ttgtgtcaag aacaaaagat gcttaggact     120
ttggacttgt cttacaataa tataagagac cttccaagtt ttaatggttg ccatgctctg     180
gaagaaattt ctttacagcg taatcaaatc taccaaataa aggaaggcac ctttcaaggc     240
ctgatatctc taaggattct agatctgagt agaaacctga tacatgaaat tcacagtaga     300
gcttttgcca cacttgggcc aataactaac ctagatgtaa gtttcaatga attaacttcc     360
tttcctacgg aaggcctgaa tgggctaaat caactgaaac ttgtgggcaa cttcaagctg     420
aaagaagcct tagcagcaaa agactttgtt aacctcaggt ctttatcagt accatatgct     480
tatcagtgct gtgcattttg gggttgtgac tcttatgcaa atttaaacac agaagataac     540
agcctccagg accacagtgt ggcacaggag aaaggtactg ctgatgcagc aaatgtcaca     600
agcactcttg aaaatgaaga acatagtcaa ataattatcc attgtacacc ttcaacaggt     660
gcttttaagc cctgtgaata tttactggga agctggatga ttcgtcttac tgtgtggttc     720
attttcttgg ttgcattatt tttcaacctg cttgttattt taacaacatt tgcatcttgt     780
acatcactgc cttcgtccaa attgtttata ggcttgattt ctgtgtctaa cttattcatg     840
ggaatctata ctggcatcct aacttttctt gatgctgtgt cctggggcag attcgctgaa     900
tttggcattt ggtgggaaac tggcagtggc tgcaaagtag ctgggtttct tgcagttttc     960
tcctcagaaa gtgccatatt tttattaatg ctagcaactg tcgaaagaag cttatctgca    1020
aaagatataa tgaaaaatgg gaagagcaat catctcaaac agttccgggt tgctgccctt    1080
ttggctttcc taggtgctac agtagcaggc tgttttcccc ttttccatag agggaatat     1140
tctgcatcac ccctttgttt gccatttcct acaggtgaaa cgccatcatt aggattcact    1200
gtaacgttag tgctattaaa ctcactagca ttttttattaa tggccgttat ctacactaaa    1260
ctatactgca acttggaaaa agaggacctc tcagaaaact cacaatctag catgattaag    1320
catgtcgctt ggctaatctt caccaattgc atcttttttct gccctgtggc gttttttttca    1380
tttgcaccat tgatcactgc aatctctatc agccccgaaa taatgaagtc tgttactctg    1440
atattttttc cattgcctgc ttgcctgaat ccagtcctgt atgttttctt caacccaaag    1500
tttaagaag actggaagtt actgaagcga cgtgttacca agaaaagtgg atcagtttca    1560
gtttccatca gtagccaagg tggttgtctg aacaggatt tctactacga ctgtggcatg    1620
tactcacatt tgcagggcaa cctgactgtt tgcgactgct gcgaatcgtt tcttttaaca    1680
```

```
aagccagtat catgcaaaca cttgataaaa tcacacagct gtcctgcatt ggcagtggct   1740
tcttgccaaa gacctgaggg ctactggtcc gactgtggca cacagtcggc ccactctgat   1800
tatgcagatg aagaagattc ctttgtctca gacagttctg accaggtgca ggcctgtgga   1860
cgagcctgct tctaccagag tagaggattc cctttggtgc gctatgctta caatctacca   1920
agagttaaag actga                                                    1935
```

```
<210> SEQ ID NO 6
<211> LENGTH: 644
<212> TYPE: PRT
<213> ORGANISM: Homo sapiens
<220> FEATURE:
<223> OTHER INFORMATION: human LGR4 G-protein coupled receptor (GPCR)

<400> SEQUENCE: 6

Met Val Gln Gln Phe Pro Asn Leu Thr Gly Thr Val His Leu Glu Ser
  1               5                  10                  15

Leu Thr Leu Thr Gly Thr Lys Ile Ser Ser Ile Pro Asn Asn Leu Cys
             20                  25                  30

Gln Glu Gln Lys Met Leu Arg Thr Leu Asp Leu Ser Tyr Asn Asn Ile
         35                  40                  45

Arg Asp Leu Pro Ser Phe Asn Gly Cys His Ala Leu Glu Glu Ile Ser
     50                  55                  60

Leu Gln Arg Asn Gln Ile Tyr Gln Ile Lys Glu Gly Thr Phe Gln Gly
 65                  70                  75                  80

Leu Ile Ser Leu Arg Ile Leu Asp Leu Ser Arg Asn Leu Ile His Glu
                 85                  90                  95

Ile His Ser Arg Ala Phe Ala Thr Leu Gly Pro Ile Thr Asn Leu Asp
            100                 105                 110

Val Ser Phe Asn Glu Leu Thr Ser Phe Pro Thr Glu Gly Leu Asn Gly
        115                 120                 125

Leu Asn Gln Leu Lys Leu Val Gly Asn Phe Lys Leu Lys Glu Ala Leu
    130                 135                 140

Ala Ala Lys Asp Phe Val Asn Leu Arg Ser Leu Ser Val Pro Tyr Ala
145                 150                 155                 160

Tyr Gln Cys Cys Ala Phe Trp Gly Cys Asp Ser Tyr Ala Asn Leu Asn
                165                 170                 175

Thr Glu Asp Asn Ser Leu Gln Asp His Ser Val Ala Gln Glu Lys Gly
            180                 185                 190

Thr Ala Asp Ala Ala Asn Val Thr Ser Thr Leu Glu Asn Glu Glu His
        195                 200                 205

Ser Gln Ile Ile Ile His Cys Thr Pro Ser Thr Gly Ala Phe Lys Pro
    210                 215                 220

Cys Glu Tyr Leu Leu Gly Ser Trp Met Ile Arg Leu Thr Val Trp Phe
225                 230                 235                 240

Ile Phe Leu Val Ala Leu Phe Phe Asn Leu Leu Val Ile Leu Thr Thr
                245                 250                 255

Phe Ala Ser Cys Thr Ser Leu Pro Ser Ser Lys Leu Phe Ile Gly Leu
            260                 265                 270

Ile Ser Val Ser Asn Leu Phe Met Gly Ile Tyr Thr Gly Ile Leu Thr
        275                 280                 285

Phe Leu Asp Ala Val Ser Trp Gly Arg Phe Ala Glu Phe Gly Ile Trp
    290                 295                 300

Trp Glu Thr Gly Ser Gly Cys Lys Val Ala Gly Phe Leu Ala Val Phe
```

```
                    305                 310                 315                 320
Ser Ser Glu Ser Ala Ile Phe Leu Leu Met Leu Ala Thr Val Glu Arg
                325                 330                 335

Ser Leu Ser Ala Lys Asp Ile Met Lys Asn Gly Lys Ser Asn His Leu
            340                 345                 350

Lys Gln Phe Arg Val Ala Ala Leu Leu Ala Phe Leu Gly Ala Thr Val
        355                 360                 365

Ala Gly Cys Phe Pro Leu Phe His Arg Gly Glu Tyr Ser Ala Ser Pro
    370                 375                 380

Leu Cys Leu Pro Phe Pro Thr Gly Glu Thr Pro Ser Leu Gly Phe Thr
385                 390                 395                 400

Val Thr Leu Val Leu Leu Asn Ser Leu Ala Phe Leu Leu Met Ala Val
                405                 410                 415

Ile Tyr Thr Lys Leu Tyr Cys Asn Leu Glu Lys Glu Asp Leu Ser Glu
                420                 425                 430

Asn Ser Gln Ser Ser Met Ile Lys His Val Ala Trp Leu Ile Phe Thr
            435                 440                 445

Asn Cys Ile Phe Phe Cys Pro Val Ala Phe Phe Ser Phe Ala Pro Leu
450                 455                 460

Ile Thr Ala Ile Ser Ile Ser Pro Glu Ile Met Lys Ser Val Thr Leu
465                 470                 475                 480

Ile Phe Phe Pro Leu Pro Ala Cys Leu Asn Pro Val Leu Tyr Val Phe
                485                 490                 495

Phe Asn Pro Lys Phe Lys Glu Asp Trp Lys Leu Leu Lys Arg Arg Val
            500                 505                 510

Thr Lys Lys Ser Gly Ser Val Ser Val Ser Ile Ser Ser Gln Gly Gly
        515                 520                 525

Cys Leu Glu Gln Asp Phe Tyr Tyr Asp Cys Gly Met Tyr Ser His Leu
    530                 535                 540

Gln Gly Asn Leu Thr Val Cys Asp Cys Cys Glu Ser Phe Leu Leu Thr
545                 550                 555                 560

Lys Pro Val Ser Cys Lys His Leu Ile Lys Ser His Ser Cys Pro Ala
                565                 570                 575

Leu Ala Val Ala Ser Cys Gln Arg Pro Glu Gly Tyr Trp Ser Asp Cys
            580                 585                 590

Gly Thr Gln Ser Ala His Ser Asp Tyr Ala Asp Glu Glu Asp Ser Phe
        595                 600                 605

Val Ser Asp Ser Ser Asp Gln Val Gln Ala Cys Gly Arg Ala Cys Phe
    610                 615                 620

Tyr Gln Ser Arg Gly Phe Pro Leu Val Arg Tyr Ala Tyr Asn Leu Pro
625                 630                 635                 640

Arg Val Lys Asp

<210> SEQ ID NO 7
<211> LENGTH: 2724
<212> TYPE: DNA
<213> ORGANISM: Homo sapiens
<220> FEATURE:
<223> OTHER INFORMATION: human LGR5 G-protein coupled receptor (GPCR)

<400> SEQUENCE: 7
atggacacct cccggctcgg tgtgctcctg tccttgcctg tgctgctgca gctggcgacc      60
gggggcagct ctcccaggtc tggtgtgttg ctgaggggct gccccacaca ctgtcattgc     120
gagcccgacg gcaggatgtt gctcagggtg gactgctccg acctggggct ctcggagctg     180
```

```
ccttccaacc tcagcgtctt cacctcctac ctagacctca gtatgaacaa catcagtcag    240
ctgctcccga atccctgcc cagtctccgc ttcctggagg agttacgtct tgcgggaaac    300
gctctgacat acattcccaa gggagcattc actggccttt acagtcttaa agttcttatg    360
ctgcagaata atcagctaag acacgtaccc acagaagctc tgcagaattt gcgaagcctt    420
caatccctgc gtctggatgc taaccacatc agctatgtgc ccccaagctg tttcagtggc    480
ctgcattccc tgaggcacct gtggctggat gacaatgcgt taacagaaat ccccgtccag    540
gcttttagaa gtttatcggc attgcaagcc atgaccttgg ccctgaacaa atacaccac    600 ataccagact atgcctttgg aaacctctcc agcttggtag ttctacatct ccataacaat    660
agaatccact ccctgggaaa gaaatgcttt gatgggctcc acagcctaga gactttagat    720
ttaaattaca ataaccttga tgaattcccc actgcaatta ggacactctc caaccttaaa    780
gaactaggat tcatagcaa caatatcagg tcgatacctg agaaagcatt tgtaggcaac    840
ccttctctta ttacaataca tttctatgac aatcccatcc aatttgttgg gagatctgct    900
tttcaacatt tacctgaact aagaacactg actctgaatg gtgcctcaca aataactgaa    960
tttcctgatt taactggaac tgcaaacctg gagagtctga ctttaactgg agcacagatc    1020
tcatctcttc ctcaaaccgt ctgcaatcag ttacctaatc tccaagtgct agatctgtct    1080
tacaacctat tagaagattt acccagtttt tcagtctgcc aaaagcttca gaaaattgac    1140
ctaagacata atgaaatcta cgaaattaaa gttgacactt tccagcagtt gcttagcctc    1200
cgatcgctga atttggcttg gaacaaaatt gctattattc accccaatgc attttccact    1260
ttgccatccc taataaagct ggacctatcg tccaacctcc tgtcgtcttt tcctataact    1320
gggttacatg gtttaactca cttaaaatta acaggaaatc atgccttaca gagcttgata    1380
tcatctgaaa actttccaga actcaaggtt atagaaatgc cttatgctta ccagtgctgt    1440
gcatttggag tgtgtgagaa tgcctataag atttctaatc aatggaataa aggtgacaac    1500
agcagtatgg acgaccttca taagaaagat gctggaatgt tcaggctca agatgaacgt    1560 gaccttgaag atttcctgct tgactttgag gaagacctga agcccttca ttcagtgcag    1620 tgttcacctt ccccaggccc cttcaaaccc tgtgaacacc tgcttgatgg ctggctgatc    1680
agaattggag tgtggaccat agcagttctg gcacttactt gtaatgcttt ggtgacttca    1740
acagttttca gatcccctct gtacatttcc cccattaaac tgttaattgg ggtcatcgca    1800
gcagtgaaca tgctcacggg agtctccagt gccgtgctgg ctggtgtgga tgcgttcact    1860
tttggcagct ttgcacgaca tggtgcctgg tgggagaatg gggttggttg ccatgtcatt    1920
ggttttttgt ccattttttgc ttcagaatca tctgttttcc tgcttactct ggcagccctg    1980
gagcgtgggt tctctgtgaa atattctgca aaatttgaaa cgaaagctcc attttctagc    2040
ctgaaagtaa tcattttgct ctgtgccctg ctggccttga ccatggccgc agttcccctg    2100
ctgggtggca gcaagtatgg cgcctcccct ctctgcctgc ctttgccttt tggggagccc    2160
agcaccatgg gctacatggt cgctctcatc ttgctcaatt cccttttgctt cctcatgatg    2220 accattgcct acaccaagct ctactgcaat ttggacaagg gagacctgga gaatatttgg    2280
gactgctcta tggtaaaaca cattgccctg ttgctcttca ccaactgcat cctaaactgc    2340
cctgtggctt tcttgtcctt ctcctctttta ataaaccttta catttatcag tcctgaagta    2400 attaagtttta tccttctggt ggtagtccca cttcctgcat gtctcaatcc ccttctctac    2460
atcttgttca atcctcactt taaggaggat ctggtgagcc tgagaaagca aacctacgtc    2520
```

-continued

```
tggacaagat caaaacaccc aagcttgatg tcaattaact ctgatgatgt cgaaaaacag    2580
tcctgtgact caactcaagc cttggtaacc tttaccagct ccagcatcac ttatgacctg    2640
cctcccagtt ccgtgccatc accagcttat ccagtgactg agagctgcca tctttcctct    2700
gtggcatttg tcccatgtct ctaa                                           2724
```

<210> SEQ ID NO 8
<211> LENGTH: 907
<212> TYPE: PRT
<213> ORGANISM: Homo sapiens
<220> FEATURE:
<223> OTHER INFORMATION: human LGR5 G-protein coupled receptor (GPCR)

<400> SEQUENCE: 8

```
Met Asp Thr Ser Arg Leu Gly Val Leu Ser Leu Pro Val Leu Leu
 1               5                  10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
    290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
```

-continued

```
                    325                 330                 335
Gly Ala Gln Ile Ser Ser Leu Pro Gln Thr Val Cys Asn Gln Leu Pro
                340                 345                 350
Asn Leu Gln Val Leu Asp Leu Ser Tyr Asn Leu Leu Glu Asp Leu Pro
                355                 360                 365
Ser Phe Ser Val Cys Gln Lys Leu Gln Lys Ile Asp Leu Arg His Asn
            370                 375                 380
Glu Ile Tyr Glu Ile Lys Val Asp Thr Phe Gln Gln Leu Leu Ser Leu
385                 390                 395                 400
Arg Ser Leu Asn Leu Ala Trp Asn Lys Ile Ala Ile His Pro Asn
                405                 410                 415
Ala Phe Ser Thr Leu Pro Ser Leu Ile Lys Leu Asp Leu Ser Ser Asn
                420                 425                 430
Leu Leu Ser Ser Phe Pro Ile Thr Gly Leu His Gly Leu Thr His Leu
            435                 440                 445
Lys Leu Thr Gly Asn His Ala Leu Gln Ser Leu Ile Ser Ser Glu Asn
    450                 455                 460
Phe Pro Glu Leu Lys Val Ile Glu Met Pro Tyr Ala Tyr Gln Cys Cys
465                 470                 475                 480
Ala Phe Gly Val Cys Glu Asn Ala Tyr Lys Ile Ser Asn Gln Trp Asn
                485                 490                 495
Lys Gly Asp Asn Ser Ser Met Asp Asp Leu His Lys Lys Asp Ala Gly
            500                 505                 510
Met Phe Gln Ala Gln Asp Glu Arg Asp Leu Glu Asp Phe Leu Leu Asp
        515                 520                 525
Phe Glu Glu Asp Leu Lys Ala Leu His Ser Val Gln Cys Ser Pro Ser
    530                 535                 540
Pro Gly Pro Phe Lys Pro Cys Glu His Leu Leu Asp Gly Trp Leu Ile
545                 550                 555                 560
Arg Ile Gly Val Trp Thr Ile Ala Val Leu Ala Leu Thr Cys Asn Ala
                565                 570                 575
Leu Val Thr Ser Thr Val Phe Arg Ser Pro Leu Tyr Ile Ser Pro Ile
            580                 585                 590
Lys Leu Leu Ile Gly Val Ile Ala Ala Val Asn Met Leu Thr Gly Val
        595                 600                 605
Ser Ser Ala Val Leu Ala Gly Val Asp Ala Phe Thr Phe Gly Ser Phe
    610                 615                 620
Ala Arg His Gly Ala Trp Trp Glu Asn Gly Val Gly Cys His Val Ile
625                 630                 635                 640
Gly Phe Leu Ser Ile Phe Ala Ser Glu Ser Ser Val Phe Leu Leu Thr
                645                 650                 655
Leu Ala Ala Leu Glu Arg Gly Phe Ser Val Lys Tyr Ser Ala Lys Phe
            660                 665                 670
Glu Thr Lys Ala Pro Phe Ser Ser Leu Lys Val Ile Leu Leu Leu Cys
        675                 680                 685
Ala Leu Leu Ala Leu Thr Met Ala Ala Val Pro Leu Leu Gly Gly Ser
    690                 695                 700
Lys Tyr Gly Ala Ser Pro Leu Cys Leu Pro Leu Pro Phe Gly Glu Pro
705                 710                 715                 720
Ser Thr Met Gly Tyr Met Val Ala Leu Ile Leu Leu Asn Ser Leu Cys
                725                 730                 735
Phe Leu Met Met Thr Ile Ala Tyr Thr Lys Leu Tyr Cys Asn Leu Asp
                740                 745                 750
```

```
Lys Gly Asp Leu Glu Asn Ile Trp Asp Cys Ser Met Val Lys His Ile
            755                 760                 765
Ala Leu Leu Leu Phe Thr Asn Cys Ile Leu Asn Cys Pro Val Ala Phe
        770                 775                 780
Leu Ser Phe Ser Ser Leu Ile Asn Leu Thr Phe Ile Ser Pro Glu Val
785                 790                 795                 800
Ile Lys Phe Ile Leu Leu Val Val Pro Leu Pro Ala Cys Leu Asn
                805                 810                 815
Pro Leu Leu Tyr Ile Leu Phe Asn Pro His Phe Lys Glu Asp Leu Val
            820                 825                 830
Ser Leu Arg Lys Gln Thr Tyr Val Trp Thr Arg Ser Lys His Pro Ser
        835                 840                 845
Leu Met Ser Ile Asn Ser Asp Asp Val Glu Lys Gln Ser Cys Asp Ser
    850                 855                 860
Thr Gln Ala Leu Val Thr Phe Thr Ser Ser Ile Thr Tyr Asp Leu
865                 870                 875                 880
Pro Pro Ser Ser Val Pro Ser Pro Ala Tyr Pro Val Thr Glu Ser Cys
                885                 890                 895
His Leu Ser Ser Val Ala Phe Val Pro Cys Leu
            900                 905

<210> SEQ ID NO 9
<211> LENGTH: 2484
<212> TYPE: DNA
<213> ORGANISM: Homo sapiens
<220> FEATURE:
<223> OTHER INFORMATION: human LGR6 G-protein coupled receptor (GPCR)

<400> SEQUENCE: 9
atgcgcttgg agggagaggg ccgctcagcg agggcgggac agaatctctc ccgggctggg      60
agtgcacggc gcggtgcgcc cagggacctc agcatgaaca acctcacaga gcttcagcct     120
ggcctcttcc accacctgcg cttcttggag gagctgcgtc tctctgggaa ccatctctca     180
cacatcccag acaagcatt ctctggtctc tacagcctga aaatcctgat gctgcagaac      240
aatcagctgg gaggaatccc cgcagaggcg ctgtgggagc tgccgagcct gcagtcgcta     300
gacctgaatt ataacaagct gcaggagttc cctgtggcca tccggaccct gggcagactg     360
caggaactgg ggttccataa caacaacatc aaggccatcc agaaaaaggc cttcatgggg     420
aaccctctgc tacagacgat acactttat gataacccaa tccagtttgt gggaagatcg      480
gcattccagt acctgcctaa actccacaca ctatctctga tggtgccat ggacatccag      540
gagtttccag atctcaaagg caccaccagc ctggagatcc tgaccctgac cgcgcaggc      600
atccggctgc tcccatcggg gatgtgccaa cagctgccca ggctccgagt cctggaactg     660
tctcacaatc aaattgagga gctgccagc ctgcacaggt gtcagaaatt ggaggaaatc      720
ggcctccaac acaaccgcat ctgggaaatt ggagctgaca ccttcagcca gctgagctcc     780
ctgcaagccc tggatcttag ctggaacgca atccggtcca tccaccccga ggccttctcc     840
accctgcact ccctggtcaa gctggacctg acagacaacc agctgaccac actgccctg      900
gctggacttg ggggcttgat gcatctgaag ctcaaaggga accttgctct tcccaggcc      960
ttctccaagg acagtttccc aaaactgagg atcctggagg tgccttatgc ctaccagtgc    1020
tgtccctatg ggatgtgtgc cagcttcttc aaggcctctg ggcagtggga ggctgaagac    1080
cttcaccttg atgatgagga gtcttcaaaa aggccctgg gcctccttgc cagacaagca    1140
```

-continued

```
gagaaccact atgaccagga cctggatgag ctccagctgg agatggagga ctcaaagcca    1200
caccccagtg tccagtgtag ccctactcca ggccccttca agccctgtga gtacctcttt    1260
gaaagctggg gcatccgcct ggccgtgtgg gccatcgtgt tgctctccgt gctctgcaat    1320
ggactggtgc tgctgaccgt gttcgctggc gggcctgtcc ccctgccccc ggtcaagttt    1380
gtggtaggtg cgattgcagg cgccaacacc ttgactggca tttcctgtgg ccttctagcc    1440
tcagtcgatg ccctgacctt tggtcagttc tctgagtacg gagcccgctg ggagacgggg    1500
ctaggctgcc gggccactgg cttcctggca gtacttgggt cggaggcatc ggtgctgctg    1560
ctcactctgg ccgcagtgca gtgcagcgtc tccgtctcct gtgtccgggc ctatgggaag    1620
tccccctccc tgggcagcgt tcgagcaggg gtcctaggct gcctggcact ggcagggctg    1680
gccgccgcac tgcccctggc tcagtgggaa gaatacgggg cctccccact ctgcctgccc    1740
tacgcgccac tgagggtca gccagcagcc ctgggcttca ccgtggccct ggtgatgatg    1800
aactccttct gtttcctggt cgtggccggt gcctacatca aactgtactg tgacctgccg    1860
cggggcgact ttgaggccgt gtgggactgc gccatggtga ggcacgtggc ctggctcatc    1920
ttcgcagacg gctcctcta ctgtcccgtg gccttcctca gcttcgcctc catgctgggc    1980
ctcttccctg tcacgcccga ggccgtcaag tctgtcctgc tggtggtgct gcccctgcct    2040
gcctgcctca acccactgct gtacctgctc ttcaaccccc acttccggga tgaccttcgg    2100
cggcttcggc ccgcgcagg ggactcaggg ccctagcct atgctgcggc cggggagctg    2160
gagaagagct cctgtgattc tacccaggcc ctggtagcct tctctgatgt ggatctcatt    2220
ctggaagctt ctgaagctgg gcggcccct gggctggaga cctatggctt cccctcagtg    2280
accctcatct cctgtcagca gccaggggcc cccaggctgg agggcagcca ttgtgtagag    2340
ccagagggga accactttgg gaaccccaa ccctccatgg atggagaact gctgctgagg    2400
gcagagggat ctacgccagc aggtggaggc ttgtcagggg gtggcggctt tcagccctct    2460
ggcttggcct tgcttcacac gtat                                           2484
```

<210> SEQ ID NO 10
<211> LENGTH: 828
<212> TYPE: PRT
<213> ORGANISM: Homo sapiens
<220> FEATURE:
<223> OTHER INFORMATION: human LGR6 G-protein coupled receptor (GPCR)

<400> SEQUENCE: 10

```
Met Arg Leu Glu Gly Glu Gly Arg Ser Ala Arg Ala Gly Gln Asn Leu
  1               5                  10                  15

Ser Arg Ala Gly Ser Ala Arg Arg Gly Ala Pro Arg Asp Leu Ser Met
             20                  25                  30

Asn Asn Leu Thr Glu Leu Gln Pro Gly Leu Phe His His Leu Arg Phe
         35                  40                  45

Leu Glu Glu Leu Arg Leu Ser Gly Asn His Leu Ser His Ile Pro Gly
     50                  55                  60

Gln Ala Phe Ser Gly Leu Tyr Ser Leu Lys Ile Leu Met Leu Gln Asn
 65                  70                  75                  80

Asn Gln Leu Gly Gly Ile Pro Ala Glu Ala Leu Trp Glu Leu Pro Ser
                 85                  90                  95

Leu Gln Ser Leu Asp Leu Asn Tyr Asn Lys Leu Gln Glu Phe Pro Val
            100                 105                 110

Ala Ile Arg Thr Leu Gly Arg Leu Gln Glu Leu Gly Phe His Asn Asn
        115                 120                 125
```

```
Asn Ile Lys Ala Ile Pro Glu Lys Ala Phe Met Gly Asn Pro Leu Leu
    130                 135                 140
Gln Thr Ile His Phe Tyr Asp Asn Pro Ile Gln Phe Val Gly Arg Ser
145                 150                 155                 160
Ala Phe Gln Tyr Leu Pro Lys Leu His Thr Leu Ser Leu Asn Gly Ala
                165                 170                 175
Met Asp Ile Gln Glu Phe Pro Asp Leu Lys Gly Thr Thr Ser Leu Glu
            180                 185                 190
Ile Leu Thr Leu Thr Arg Ala Gly Ile Arg Leu Leu Pro Ser Gly Met
        195                 200                 205
Cys Gln Gln Leu Pro Arg Leu Arg Val Leu Glu Leu Ser His Asn Gln
    210                 215                 220
Ile Glu Glu Leu Pro Ser Leu His Arg Cys Gln Lys Leu Glu Glu Ile
225                 230                 235                 240
Gly Leu Gln His Asn Arg Ile Trp Glu Ile Gly Ala Asp Thr Phe Ser
                245                 250                 255
Gln Leu Ser Ser Leu Gln Ala Leu Asp Leu Ser Trp Asn Ala Ile Arg
            260                 265                 270
Ser Ile His Pro Glu Ala Phe Ser Thr Leu His Ser Leu Val Lys Leu
        275                 280                 285
Asp Leu Thr Asp Asn Gln Leu Thr Thr Leu Pro Leu Ala Gly Leu Gly
    290                 295                 300
Gly Leu Met His Leu Lys Leu Lys Gly Asn Leu Ala Leu Ser Gln Ala
305                 310                 315                 320
Phe Ser Lys Asp Ser Phe Pro Lys Leu Arg Ile Leu Glu Val Pro Tyr
                325                 330                 335
Ala Tyr Gln Cys Cys Pro Tyr Gly Met Cys Ala Ser Phe Phe Lys Ala
            340                 345                 350
Ser Gly Gln Trp Glu Ala Glu Asp Leu His Leu Asp Asp Glu Glu Ser
        355                 360                 365
Ser Lys Arg Pro Leu Gly Leu Leu Ala Arg Gln Ala Glu Asn His Tyr
    370                 375                 380
Asp Gln Asp Leu Asp Glu Leu Gln Leu Glu Met Glu Asp Ser Lys Pro
385                 390                 395                 400
His Pro Ser Val Gln Cys Ser Pro Thr Pro Gly Pro Phe Lys Pro Cys
                405                 410                 415
Glu Tyr Leu Phe Glu Ser Trp Gly Ile Arg Leu Ala Val Trp Ala Ile
            420                 425                 430
Val Leu Leu Ser Val Leu Cys Asn Gly Leu Val Leu Leu Thr Val Phe
        435                 440                 445
Ala Gly Gly Pro Val Pro Leu Pro Pro Val Lys Phe Val Val Gly Ala
    450                 455                 460
Ile Ala Gly Ala Asn Thr Leu Thr Gly Ile Ser Cys Gly Leu Leu Ala
465                 470                 475                 480
Ser Val Asp Ala Leu Thr Phe Gly Gln Phe Ser Glu Tyr Gly Ala Arg
                485                 490                 495
Trp Glu Thr Gly Leu Gly Cys Arg Ala Thr Gly Phe Leu Ala Val Leu
            500                 505                 510
Gly Ser Glu Ala Ser Val Leu Leu Leu Thr Leu Ala Ala Val Gln Cys
        515                 520                 525
Ser Val Ser Val Ser Cys Val Arg Ala Tyr Gly Lys Ser Pro Ser Leu
    530                 535                 540
```

```
Gly Ser Val Arg Ala Gly Val Leu Gly Cys Leu Ala Leu Ala Gly Leu
545                 550                 555                 560

Ala Ala Ala Leu Pro Leu Ala Ser Val Gly Glu Tyr Gly Ala Ser Pro
            565                 570                 575

Leu Cys Leu Pro Tyr Ala Pro Pro Glu Gly Gln Pro Ala Ala Leu Gly
        580                 585                 590

Phe Thr Val Ala Leu Val Met Met Asn Ser Phe Cys Phe Leu Val Val
    595                 600                 605

Ala Gly Ala Tyr Ile Lys Leu Tyr Cys Asp Leu Pro Arg Gly Asp Phe
610                 615                 620

Glu Ala Val Trp Asp Cys Ala Met Val Arg His Val Ala Trp Leu Ile
625                 630                 635                 640

Phe Ala Asp Gly Leu Leu Tyr Cys Pro Val Ala Phe Leu Ser Phe Ala
                645                 650                 655

Ser Met Leu Gly Leu Phe Pro Val Thr Pro Glu Ala Val Lys Ser Val
            660                 665                 670

Leu Leu Val Val Leu Pro Leu Ala Cys Leu Asn Pro Leu Leu Tyr
        675                 680                 685

Leu Leu Phe Asn Pro His Phe Arg Asp Asp Leu Arg Arg Leu Arg Pro
690                 695                 700

Arg Ala Gly Asp Ser Gly Pro Leu Ala Tyr Ala Ala Gly Glu Leu
705                 710                 715                 720

Glu Lys Ser Ser Cys Asp Ser Thr Gln Ala Leu Val Ala Phe Ser Asp
                725                 730                 735

Val Asp Leu Ile Leu Glu Ala Ser Glu Ala Gly Arg Pro Pro Gly Leu
            740                 745                 750

Glu Thr Tyr Gly Phe Pro Ser Val Thr Leu Ile Ser Cys Gln Gln Pro
        755                 760                 765

Gly Ala Pro Arg Leu Glu Gly Ser His Cys Val Glu Pro Glu Gly Asn
770                 775                 780

His Phe Gly Asn Pro Gln Pro Ser Met Asp Gly Glu Leu Leu Leu Arg
785                 790                 795                 800

Ala Glu Gly Ser Thr Pro Ala Gly Gly Gly Leu Ser Gly Gly Gly Gly
                805                 810                 815

Phe Gln Pro Ser Gly Leu Ala Leu Leu His Thr Tyr
            820                 825
```

<210> SEQ ID NO 11
<211> LENGTH: 903
<212> TYPE: DNA
<213> ORGANISM: Homo sapiens
<220> FEATURE:
<223> OTHER INFORMATION: human GPR40 G-protein coupled receptor (GPCR)

<400> SEQUENCE: 11

```
atggacctgc ccccgcagct ctccttcggc ctctatgtgg ccgcctttgc gctgggcttc      60
ccgctcaacg tcctggccat ccgaggcgcg acggcccacg cccggctccg tctcacccct     120
agcctggtct acgccctgaa cctgggctgc tccgacctgc tgctgacagt ctctctgccc     180
ctgaaggcgg tggaggcgct agcctccggg gcctggcctc tgccggcctc gctgtgcccc     240
gtcttcgcgg tggcccactt cttcccactc tatgccggcg ggggcttcct ggccgccctg     300
agtgcaggcc gctacctggg agcagccttc cccttgggct accaagcctt ccggaggccg     360
tgctattcct gggggtgtg cgcggccatc tgggccctcg tcctgtgtca cctggtctg      420 gtctttgggt tggaggctcc aggaggctgg ctggaccaca gcaacacctc cctgggcatc     480
```

```
aacacaccgg tcaacggctc tccggtctgc ctggaggcct gggacccggc ctctgccggc    540
ccggcccgct tcagcctctc tctcctgctc ttttttctgc ccttggccat cacagccttc    600
tgctacgtgg gctgcctccg ggcactggcc cgctccggcc tgacgcacag gcggaagctg    660
cgggccgcct gggtggccgg cggggccctc ctcacgctgc tgctctgcgt aggaccctac    720
aacgcctcca acgtggccag cttcctgtac cccaatctag gaggctcctg gcggaagctg    780
gggctcatca cgggtgcctg gagtgtggtg cttaatccgc tggtgaccgg ttacttggga    840
aggggtcctg gcctgaagac agtgtgtgcg gcaagaacgc aagggggcaa gtcccagaag    900
taa                                                                   903
```

<210> SEQ ID NO 12
<211> LENGTH: 300
<212> TYPE: PRT
<213> ORGANISM: Homo sapiens
<220> FEATURE:
<223> OTHER INFORMATION: human GPR40 G-protein coupled receptor (GPCR)

<400> SEQUENCE: 12

```
Met Asp Leu Pro Pro Gln Leu Ser Phe Gly Leu Tyr Val Ala Ala Phe
 1               5                   10                  15

Ala Leu Gly Phe Pro Leu Asn Val Leu Ala Ile Arg Gly Ala Thr Ala
                20                  25                  30

His Ala Arg Leu Arg Leu Thr Pro Ser Leu Val Tyr Ala Leu Asn Leu
            35                  40                  45

Gly Cys Ser Asp Leu Leu Leu Thr Val Ser Leu Pro Leu Lys Ala Val
        50                  55                  60

Glu Ala Leu Ala Ser Gly Ala Trp Pro Leu Pro Ala Ser Leu Cys Pro
65                  70                  75                  80

Val Phe Ala Val Ala His Phe Phe Pro Leu Tyr Ala Gly Gly Gly Phe
                85                  90                  95

Leu Ala Ala Leu Ser Ala Gly Arg Tyr Leu Gly Ala Ala Phe Pro Leu
            100                 105                 110

Gly Tyr Gln Ala Phe Arg Arg Pro Cys Tyr Ser Trp Gly Val Cys Ala
        115                 120                 125

Ala Ile Trp Ala Leu Val Leu Cys His Leu Gly Leu Val Phe Gly Leu
130                 135                 140

Glu Ala Pro Gly Gly Trp Leu Asp His Ser Asn Thr Ser Leu Gly Ile
145                 150                 155                 160

Asn Thr Pro Val Asn Gly Ser Pro Val Cys Leu Glu Ala Trp Asp Pro
                165                 170                 175

Ala Ser Ala Gly Pro Ala Arg Phe Ser Leu Ser Leu Leu Leu Phe Phe
            180                 185                 190

Leu Pro Leu Ala Ile Thr Ala Phe Cys Tyr Val Gly Cys Leu Arg Ala
        195                 200                 205

Leu Ala Arg Ser Gly Leu Thr His Arg Arg Lys Leu Arg Ala Ala Trp
    210                 215                 220

Val Ala Gly Gly Ala Leu Leu Thr Leu Leu Leu Cys Val Gly Pro Tyr
225                 230                 235                 240

Asn Ala Ser Asn Val Ala Ser Phe Leu Tyr Pro Asn Leu Gly Gly Ser
                245                 250                 255

Trp Arg Lys Leu Gly Leu Ile Thr Gly Ala Trp Ser Val Val Leu Asn
            260                 265                 270

Pro Leu Val Thr Gly Tyr Leu Gly Arg Gly Pro Gly Leu Lys Thr Val
```

-continued

```
                275                 280                 285
Cys Ala Ala Arg Thr Gln Gly Gly Lys Ser Gln Lys
        290                 295                 300
```

<210> SEQ ID NO 13
<211> LENGTH: 993
<212> TYPE: DNA
<213> ORGANISM: Homo sapiens
<220> FEATURE:
<223> OTHER INFORMATION: human GPR43 G-protein coupled receptor (GPCR)

<400> SEQUENCE: 13

```
atgctgccgg actggaagag ctccttgatc ctcatggctt acatcatcat cttcctcact    60
ggcctccctg ccaacctcct ggccctgcgg gcctttgtgg gcggatccg ccagccccag   120
cctgcacctg tgcacatcct cctgctgagc ctgacgctgg ccgacctcct cctgctgctg   180
ctgctgccct tcaagatcat cgaggctgcg tcgaacttcc gctggtacct gcccaaggtc   240
gtctgcgccc tcacgagttt tggcttctac agcagcatct actgcagcac gtggctcctg   300
gcgggcatca gcatcgagcg ctacctggga gtggctttcc ccgtgcagta caagctctcc   360
cgccggcctc tgtatggagt gattgcagct ctggtggcct gggttatgtc ctttggtcac   420
tgcaccatcg tgatcatcgt tcaatacttg aacacgactg agcaggtcag aagtggcaat   480
gaaattacct gctacgagaa cttcaccgat aaccagttgg acgtggtgct gcccgtgcgg   540
ctggagctgt gcctggtgct cttcttcatc cccatggcag tcaccatctt ctgctactgg   600
cgttttgtgt ggatcatgct ctcccagccc cttgtggggg cccagaggcg cgccgagcc   660
gtggggctgg ctgtggtgac gctgctcaat ttcctggtgt gcttcggacc ttacaacgtg   720
tcccacctgg tggggtatca ccagagaaaa agccctggt ggcggtcaat agccgtggtg   780
ttcagttcac tcaacgccag tctggacccc ctgctcttct atttctcttc ttcagtggtg   840
cgcagggcat tgggagagg gctgcaggtg ctgcggaatc agggctcctc cctgttggga   900
cgcagaggca agacacagc agaggggaca atgaggaca ggggtgtggg tcaaggagaa   960
gggatgccaa gttcggactt cactacagag tag                                993
```

<210> SEQ ID NO 14
<211> LENGTH: 330
<212> TYPE: PRT
<213> ORGANISM: Homo sapiens
<220> FEATURE:
<223> OTHER INFORMATION: human GPR43 G-protein coupled receptor (GPCR)

<400> SEQUENCE: 14

```
Met Leu Pro Asp Trp Lys Ser Ser Leu Ile Leu Met Ala Tyr Ile Ile
  1               5                  10                  15

Ile Phe Leu Thr Gly Leu Pro Ala Asn Leu Leu Ala Leu Arg Ala Phe
             20                  25                  30

Val Gly Arg Ile Arg Gln Pro Gln Pro Ala Pro Val His Ile Leu Leu
         35                  40                  45

Leu Ser Leu Thr Leu Ala Asp Leu Leu Leu Leu Leu Leu Pro Phe
     50                  55                  60

Lys Ile Ile Glu Ala Ala Ser Asn Phe Arg Trp Tyr Leu Pro Lys Val
 65                  70                  75                  80

Val Cys Ala Leu Thr Ser Phe Gly Phe Tyr Ser Ser Ile Tyr Cys Ser
                 85                  90                  95

Thr Trp Leu Leu Ala Gly Ile Ser Ile Glu Arg Tyr Leu Gly Val Ala
            100                 105                 110
```

```
Phe Pro Val Gln Tyr Lys Leu Ser Arg Arg Pro Leu Tyr Gly Val Ile
            115                 120                 125

Ala Ala Leu Val Ala Trp Val Met Ser Phe Gly His Cys Thr Ile Val
    130                 135                 140

Ile Ile Val Gln Tyr Leu Asn Thr Thr Glu Gln Val Arg Ser Gly Asn
145                 150                 155                 160

Glu Ile Thr Cys Tyr Glu Asn Phe Thr Asp Asn Gln Leu Asp Val Val
                165                 170                 175

Leu Pro Val Arg Leu Glu Leu Cys Leu Val Leu Phe Phe Ile Pro Met
            180                 185                 190

Ala Val Thr Ile Phe Cys Tyr Trp Arg Phe Val Trp Ile Met Leu Ser
        195                 200                 205

Gln Pro Leu Val Gly Ala Gln Arg Arg Arg Arg Ala Val Gly Leu Ala
    210                 215                 220

Val Val Thr Leu Leu Asn Phe Leu Val Cys Phe Gly Pro Tyr Asn Val
225                 230                 235                 240

Ser His Leu Val Gly Tyr His Gln Arg Lys Ser Pro Trp Trp Arg Ser
                245                 250                 255

Ile Ala Val Val Phe Ser Ser Leu Asn Ala Ser Leu Asp Pro Leu Leu
            260                 265                 270

Phe Tyr Phe Ser Ser Ser Val Val Arg Arg Ala Phe Gly Arg Gly Leu
        275                 280                 285

Gln Val Leu Arg Asn Gln Gly Ser Ser Leu Leu Gly Arg Arg Gly Lys
    290                 295                 300

Asp Thr Ala Glu Gly Thr Asn Glu Asp Arg Gly Val Gly Gln Gly Glu
305                 310                 315                 320

Gly Met Pro Ser Ser Asp Phe Thr Thr Glu
                325                 330

<210> SEQ ID NO 15
<211> LENGTH: 1038
<212> TYPE: DNA
<213> ORGANISM: Homo sapiens
<220> FEATURE:
<223> OTHER INFORMATION: human TGR18 G-protein coupled receptor (GPCR)

<400> SEQUENCE: 15
atgatggcag aaccatttac tgaaattggt ggatatgctg caggcttggc atggaatgca      60
acttgcaaaa actggctggc agcagaggct gccctggaaa agtactacct ttccattttt     120
tatgggattg agttcgttgt gggagtcctt ggaaatacca ttgttgttta cggctacatc     180
ttctctctga agaactggaa cagcagtaat atttatctct ttaacctctc tgtctctgac     240
ttagcttttc tgtgcaccct ccccatgctg ataaggagtt atgccaatgg aaactggata     300
tatggagacg tgctctgcat aagcaaccga tatgtgcttc atgccaacct ctataccagc     360
attctctttc tcactttat cagcatagat cgatacttga taattaagta tcctttccga      420
gaacaccttc tgcaaaagaa agagtttgct attttaatct ccttggccat ttgggtttta     480
gtaaccttag agttactacc catacttccc cttataaatc ctgttataac tgacaatggc     540
accacctgta tgattttgc aagttctgga gaccccaact acaacctcat ttacagcatg     600
tgtctaacac tgttggggtt ccttattcct cttttttgtga tgtgtttctt ttattacaag     660
attgctctct tcctaaagca gaggaatagg caggttgcta ctgctctgcc ccttgaaaag     720
cctctcaact tggtcatcat ggcagtggta atcttctctg tgcttttttac accctatcac     780
```

-continued

```
gtcatgcgga atgtgaggat cgcttcacgc ctggggagtt ggaagcagta tcagtgcact      840
caggtcgtca tcaactcctt ttacattgtg acacggcctt tggcctttct gaacagtgtc      900
atcaaccctg tcttctattt tcttttggga gatcacttca gggacatgct gatgaatcaa      960
ctgagacaca acttcaaatc ccttacatcc tttagcagat gggctcatga actcctactt     1020
tcattcagag aaaagtga                                                    1038
```

<210> SEQ ID NO 16
<211> LENGTH: 345
<212> TYPE: PRT
<213> ORGANISM: Homo sapiens
<220> FEATURE:
<223> OTHER INFORMATION: human TGR18 G-protein coupled receptor (GPCR)

<400> SEQUENCE: 16

```
Met Met Ala Glu Pro Phe Thr Glu Ile Gly Gly Tyr Ala Ala Gly Leu
 1               5                  10                  15

Ala Trp Asn Ala Thr Cys Lys Asn Trp Leu Ala Ala Glu Ala Ala Leu
            20                  25                  30

Glu Lys Tyr Tyr Leu Ser Ile Phe Tyr Gly Ile Glu Phe Val Val Gly
        35                  40                  45

Val Leu Gly Asn Thr Ile Val Val Tyr Gly Tyr Ile Phe Ser Leu Lys
    50                  55                  60

Asn Trp Asn Ser Ser Asn Ile Tyr Leu Phe Asn Leu Ser Val Ser Asp
65                  70                  75                  80

Leu Ala Phe Leu Cys Thr Leu Pro Met Leu Ile Arg Ser Tyr Ala Asn
                85                  90                  95

Gly Asn Trp Ile Tyr Gly Asp Val Leu Cys Ile Ser Asn Arg Tyr Val
            100                 105                 110

Leu His Ala Asn Leu Tyr Thr Ser Ile Leu Phe Leu Thr Phe Ile Ser
        115                 120                 125

Ile Asp Arg Tyr Leu Ile Ile Lys Tyr Pro Phe Arg Glu His Leu Leu
    130                 135                 140

Gln Lys Lys Glu Phe Ala Ile Leu Ile Ser Leu Ala Ile Trp Val Leu
145                 150                 155                 160

Val Thr Leu Glu Leu Leu Pro Ile Leu Pro Leu Ile Asn Pro Val Ile
                165                 170                 175

Thr Asp Asn Gly Thr Thr Cys Asn Asp Phe Ala Ser Ser Gly Asp Pro
            180                 185                 190

Asn Tyr Asn Leu Ile Tyr Ser Met Cys Leu Thr Leu Leu Gly Phe Leu
        195                 200                 205

Ile Pro Leu Phe Val Met Cys Phe Phe Tyr Tyr Lys Ile Ala Leu Phe
    210                 215                 220

Leu Lys Gln Arg Asn Arg Gln Val Ala Thr Ala Leu Pro Leu Glu Lys
225                 230                 235                 240

Pro Leu Asn Leu Val Ile Met Ala Val Ile Phe Ser Val Leu Phe
                245                 250                 255

Thr Pro Tyr His Val Met Arg Asn Val Arg Ile Ala Ser Arg Leu Gly
            260                 265                 270

Ser Trp Lys Gln Tyr Gln Cys Thr Gln Val Val Ile Asn Ser Phe Tyr
        275                 280                 285

Ile Val Thr Arg Pro Leu Ala Phe Leu Asn Ser Val Ile Asn Pro Val
    290                 295                 300

Phe Tyr Phe Leu Leu Gly Asp His Phe Arg Asp Met Leu Met Asn Gln
305                 310                 315                 320
```

```
Leu Arg His Asn Phe Lys Ser Leu Thr Ser Phe Ser Arg Trp Ala His
            325                 330                 335

Glu Leu Leu Leu Ser Phe Arg Glu Lys
            340                 345

<210> SEQ ID NO 17
<211> LENGTH: 1014
<212> TYPE: DNA
<213> ORGANISM: Homo sapiens
<220> FEATURE:
<223> OTHER INFORMATION: human TGR164 G-protein coupled receptor (GPCR)

<400> SEQUENCE: 17
atgaatgagc cactagacta tttagcaaat gcttctgatt tccccgatta tgcagctgct      60
tttggaaatt gcactgatga aaacatccca ctcaagatgc actacctccc tgttatttat     120
ggcattatct cctcgtggg  atttccaggc aatgcagtag tgatatccac ttacattttc     180
aaaatgagac cttggaagag cagcaccatc attatgctga acctggcctg cacagatctg     240
ctgtatctga ccagcctccc cttcctgatt cactactatg ccagtggcga aaactggatc     300
tttggagatt tcatgtgtaa gtttatccgc ttcagcttcc atttcaacct gtatagcagc     360
atcctcttcc tcacctgttt cagcatcttc cgctactgtg tgatcattca cccaatgagc     420
tgcttttcca ttcacaaaac tcgatgtgca gttgtagcct gtgctgtggt gtggatcatt     480
tcactggtag ctgtcattcc gatgaccttc ttgatcacat caaccaacag gaccaacaga     540
tcagcctgtc tcgacctcac cagttcggat gaactcaata ctattaagtg gtacaacctg     600
attttgactg caactacttt ctgcctcccc ttggtgatag tgacactttg ctataccacg     660
attatccaca ctctgaccca tggactgcaa actgacagct gccttaagca gaaagcacga     720
aggctaacca ttctgctact ccttgcattt tacgtatgtt ttttacccct tccatatcttg     780 agggtcattc ggatcgaatc tcgcctgctt tcaatcagtt gttccattga gaatcagatc     840
catgaagctt acatcgtttc tagaccatta gctgctctga acacctttgg taacctgtta     900
ctatatgtgg tggtcagcga caactttcag caggctgtct gctcaacagt gagatgcaaa     960
gtaagcggga accttgagca agcaaagaaa attagttact caaacaaccc ttga          1014

<210> SEQ ID NO 18
<211> LENGTH: 337
<212> TYPE: PRT
<213> ORGANISM: Homo sapiens
<220> FEATURE:
<223> OTHER INFORMATION: human TGR164 G-protein coupled receptor (GPCR)

<400> SEQUENCE: 18

Met Asn Glu Pro Leu Asp Tyr Leu Ala Asn Ala Ser Asp Phe Pro Asp
  1               5                  10                  15

Tyr Ala Ala Ala Phe Gly Asn Cys Thr Asp Glu Asn Ile Pro Leu Lys
                 20                  25                  30

Met His Tyr Leu Pro Val Ile Tyr Gly Ile Ile Phe Leu Val Gly Phe
             35                  40                  45

Pro Gly Asn Ala Val Val Ile Ser Thr Tyr Ile Phe Lys Met Arg Pro
     50                  55                  60

Trp Lys Ser Ser Thr Ile Ile Met Leu Asn Leu Ala Cys Thr Asp Leu
 65                  70                  75                  80

Leu Tyr Leu Thr Ser Leu Pro Phe Leu Ile His Tyr Tyr Ala Ser Gly
                 85                  90                  95
```

```
Glu Asn Trp Ile Phe Gly Asp Phe Met Cys Lys Phe Ile Arg Phe Ser
                100                 105                 110

Phe His Phe Asn Leu Tyr Ser Ser Ile Leu Phe Leu Thr Cys Phe Ser
            115                 120                 125

Ile Phe Arg Tyr Cys Val Ile Ile His Pro Met Ser Cys Phe Ser Ile
        130                 135                 140

His Lys Thr Arg Cys Ala Val Ala Cys Ala Val Val Trp Ile Ile
145                 150                 155                 160

Ser Leu Val Ala Val Ile Pro Met Thr Phe Leu Ile Thr Ser Thr Asn
                165                 170                 175

Arg Thr Asn Arg Ser Ala Cys Leu Asp Leu Thr Ser Ser Asp Glu Leu
            180                 185                 190

Asn Thr Ile Lys Trp Tyr Asn Leu Ile Leu Thr Ala Thr Thr Phe Cys
        195                 200                 205

Leu Pro Leu Val Ile Val Thr Leu Cys Tyr Thr Thr Ile Ile His Thr
    210                 215                 220

Leu Thr His Gly Leu Gln Thr Asp Ser Cys Leu Lys Gln Lys Ala Arg
225                 230                 235                 240

Arg Leu Thr Ile Leu Leu Leu Ala Phe Tyr Val Cys Phe Leu Pro
                245                 250                 255

Phe His Ile Leu Arg Val Ile Arg Ile Glu Ser Arg Leu Leu Ser Ile
            260                 265                 270

Ser Cys Ser Ile Glu Asn Gln Ile His Glu Ala Tyr Ile Val Ser Arg
        275                 280                 285

Pro Leu Ala Ala Leu Asn Thr Phe Gly Asn Leu Leu Leu Tyr Val Val
    290                 295                 300

Val Ser Asp Asn Phe Gln Gln Ala Val Cys Ser Thr Val Arg Cys Lys
305                 310                 315                 320

Val Ser Gly Asn Leu Glu Gln Ala Lys Lys Ile Ser Tyr Ser Asn Asn
                325                 330                 335

Pro

<210> SEQ ID NO 19
<211> LENGTH: 200
<212> TYPE: PRT
<213> ORGANISM: Artificial Sequence
<220> FEATURE:
<223> OTHER INFORMATION: Description of Artificial Sequence:poly-Gly
      flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 19

Gly Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly Gly
        35                  40                  45

Gly Gly Gly Gly Gly Gly Gly Gly Gly Gly Gly Gly Gly Gly Gly
    50                  55                  60

Gly Gly Gly Gly Gly Gly Gly Gly Gly Gly Gly Gly Gly Gly Gly Gly
65                  70                  75                  80

Gly Gly Gly Gly Gly Gly Gly Gly Gly Gly Gly Gly Gly Gly Gly
```

-continued

```
                    85                  90                  95
Gly Gly Gly Gly Gly Gly Gly Gly Gly Gly Gly Gly Gly Gly Gly
                100                 105                 110
Gly Gly Gly Gly Gly Gly Gly Gly Gly Gly Gly Gly Gly Gly Gly
                115                 120                 125
Gly Gly Gly Gly Gly Gly Gly Gly Gly Gly Gly Gly Gly Gly Gly
            130                 135                 140
Gly Gly Gly Gly Gly Gly Gly Gly Gly Gly Gly Gly Gly Gly Gly
145                 150                 155                 160
Gly Gly Gly Gly Gly Gly Gly Gly Gly Gly Gly Gly Gly Gly Gly
                165                 170                 175
Gly Gly Gly Gly Gly Gly Gly Gly Gly Gly Gly Gly Gly Gly Gly
            180                 185                 190
Gly Gly Gly Gly Gly Gly Gly Gly
        195                 200
```

US 7,056,685 B1

RECEPTOR LIGANDS AND METHODS OF MODULATING RECEPTORS

CROSS REFERENCE TO RELATED APPLICATIONS

This application claims the benefit of U.S. Provisional Application 60/424,093, filed Nov. 5, 2002, which application is herein incorporated by reference.

FIELD OF THE INVENTION

The invention relates to the identification of specific ligands that bind previously identified G-protein coupled receptors (GPCRs) and methods for identifying and using modulators of the receptor-ligand interactions for various therapeutic indications.

BACKGROUND OF THE INVENTION

G-protein coupled receptors are cell surface receptors that indirectly transduce extracellular signals to downstream effectors, e.g., intracellular signaling proteins, enzymes, or channels. Changes in the activity of these effectors then mediate subsequent cellular events. The interaction between the receptor and the downstream effector is mediated by a G-protein, a heterotrimeric protein that binds GTP. Examples of mammalian G proteins include Gi, Go, Gq, Gs, and Gt.

G-protein coupled receptors ("GPCRs") typically have seven transmembrane regions, along with an extracellular domain and a cytoplasmic tail at the C-terminus. These receptors form a large superfamily of related receptor molecules that play a key role in many signaling processes, such as sensory and hormonal signal transduction. The further identification of GPCRs and the natural ligands of the receptors is important for understanding the normal process of signal transduction and as well as its involvement in pathologic processes. For example, GPCRs can be used for disease diagnosis as well as for drug discovery. GPCR ligands may be used for the treatment of GPCR-related disorders and for the identification of additional modulators of GPCR activity. Further identification of GPCRs and ligands that bind to GPCRs is therefore of great interest.

SUMMARY OF THE INVENTION

The present invention relates to the identification and characterization of ligands for particular G protein-coupled receptors (GPCRs) and methods for identifying and using modulators of the receptor-ligand interactions. Specifically, the inventors have shown that a natural ligand for TGR2 is β-alanine, a natural ligand for GPR77 is acylation stimulating protein (ASP), and a natural ligand for LGR4, LGR5, or LGR6 is a stanniocalcin. Furthermore, the inventors have discovered that short chain fatty acids, typically of 2–3 carbons in length, activate GPR43 and medium and long chain fatty acids that are 6 carbons or greater in length activate GPR40. Lastly, the invention is also based on the discovery that succinic acid is a natural ligand for TGR18 and that α-ketoglutaric acid is a natural ligand for TGR164. Modulators of the receptor-ligand interaction may be used, for example, for the treatment of a disease or condition associated with a TGR2, GPR77, LGR4, LGR5, LGR6, GPR40, GPR43, TGR18, or TGR164.

Thus, the current invention provides a method of identifying a modulator of a TGR2 polypeptide that has G-protein coupled receptor activity and (A) comprises at least 70% amino acid sequence identity to SEQ ID NO:2, (B) comprises at least 50 contiguous amino acids of SEQ ID NO:2, or (C) comprises the amino acid sequence of SEQ ID NO:2; wherein the method comprises: contacting a compound with the TGR2 polypeptide; and determining the level of binding of β-alanine to the TGR2 polypeptide in comparison to the level of binding in the absence of the compound. In some embodiments, the TGR2 polypeptide consists of at least 50, often at least 40, 30, or 20, contiguous amino acids of SEQ ID NO:2. Often, the TGR2 is recombinant. The step of determining the level of binding can comprise a binding assay such as a competitive binding assay or detecting an alteration in a β-alanine-induced TGR2 activity such as inositol phosphate accumulation.

Modulators of TGR2 receptor-ligand interactions can be used, for example, in a method of treating a patient with a TGR2-associated disorder, the method comprising administering a therapeutically effective amount of a compound identified as set forth above. The TGR2-associated disorder may be, but is not limited to, a pain disorder, a disorder in the immune system, or an inflammatory disorder.

In another aspect, the invention provides a method of identifying a modulator of a GPR77 polypeptide that has G-protein coupled receptor activity and (A) comprises at least 70% amino acid sequence identity to SEQ ID NO:4, (B) comprises at least 50 contiguous amino acids of SEQ ID NO:4, or (C) comprises the amino acid sequence of SEQ ID NO:4; wherein the method comprises: contacting a compound with the GPR77 polypeptide; and determining the level of binding of acylation stimulating protein (ASP) to the GPR77 polypeptide in comparison to the level of binding in the absence of the compound. In some embodiments, the GPR77 polypeptide consists of at least 50, often at least 40, 30, or 20, contiguous amino acids of SEQ ID NO:4. Often, the GPR77 is recombinant.

The step of determining the level of binding may comprise detecting the ability of the compound to modulate ASP binding in a competitive binding assay. The step of determining the level of binding may also comprise detecting an alteration in an ASP-induced GPR77 activity. In some embodiments, the method may further comprise a step of detecting an alteration in ASP-induced triglyceride synthesis.

The invention also provides a method of treating a patient with a GPR77-associated disorder, the method comprising administering a therapeutically effective amount of a compound identified using the method set forth above. The GPR77-associated disorder may be, but is not limited to diabetes, obesity, or atherosclerosis.

In another aspect, the invention provides a method of identifying a modulator of an LGR4, LGR5, or LGR6 polypeptide that has G-protein coupled receptor activity and (A) comprises at least 70% amino acid sequence identity to SEQ ID NO:6, SEQ ID NO:8, or SEQ ID NO:10, (B) comprises at least 50 contiguous amino acids of SEQ ID NO:6, SEQ ID NO:8, or SEQ ID NO:10, or (C) comprises the amino acid sequence of SEQ ID NO:6, SEQ ID NO:8, or SEQ ID NO:10; wherein the method comprises: contacting a compound with the polypeptide; and determining the level of binding of a stanniocalcin to the polypeptide in comparison to the level of binding in the absence of the compound. In some embodiments, the LGR polypeptide consists of at least 50, often at least 40, 30, or 20, contiguous amino acids of SEQ ID NO:6, SEQ ID NO:8, or SEQ ID NO:10. Often, the LGR4, LGR5, or LGR6 is recombinant. The step of determining the level of binding may comprise detecting the ability of the compound to alter stanniocalcin binding in a competitive binding assay. Alternatively, the step of determining the level of binding may comprise detecting an alteration in a stanniocalcin-induced activity of LGR4, LGR5, or LGR6. In some embodiments, the method may further comprise detecting an alteration in stanniocalcin-induced changes in calcium or phosphate levels in a cell.

In another embodiment, the invention provides a method of treating a patient with an LGR4, LGR5, or LGR6-associated disorder, the method comprising administering a therapeutically effective amount of a compound identified as set forth above. The disorder may be, but is not limited to, a disorder of calcium or phosphate metabolism; a bone disorder; a kidney disorder; or a growth or reproductive disorder.

In another aspect, the invention provides a method of identifying a modulator of a GPR40 polypeptide that has G-protein coupled receptor activity and (A) comprises at least 70% amino acid sequence identity to SEQ ID NO:12, (B) comprises at least 50 contiguous amino acids of SEQ ID NO:12, or (C) comprises the amino acid sequence of SEQ ID NO:12; wherein the method comprises: contacting a compound and a medium or long chain fatty acid with the polypeptide; and determining the level of activity of the polypeptide, in comparison to the level of activity in the absence of the compound. In some embodiments, the GPR40 polypeptide consists of at least 50, often at least 40, 30, or 20, contiguous amino acids of SEQ ID NO:12. Often, the fatty acid is a long chain polyunsaturated fatty acid. Often, the GPR40 is recombinant. In some embodiments, the step of determining the level of activity comprises determining the level of binding of the modulator, or the natural ligand, to the GPR40. In other embodiments, the method may comprise detecting an alteration in fatty acid-induced Gq activity.

In another aspect, the invention provides a method of identifying a modulator of a GPR43 polypeptide that has G-protein coupled receptor activity and (A) comprises at least 70% amino acid sequence identity to SEQ ID NO:14, (B) comprises at least 50 contiguous amino acids of SEQ ID NO:14, or (C) comprises the amino acid sequence of SEQ ID NO:14; wherein the method comprises: contacting a compound with the polypeptide; and determining the level of activation of the polypeptide by a short chain fatty acid, preferably of 2–3 carbons in length, in comparison to the level of activation in the absence of the compound. In some embodiments, the GPR43 polypeptide consists of at least 50, often at least 40, 30 or 20, contiguous amino acids of SEQ ID NO:14. Often, the fatty acid is a long chain polyunsaturated fatty acid and the GPR43 is recombinant. In some embodiments, the step of determining the level of activity may comprise determining the level of binding of the modulator, or the natural ligand, to the GPR43. In other embodiments, the method may comprise detecting an alteration in fatty acid-induced Gq activity.

In another embodiment, the invention provides a method of treating a patient with a GPR40 or GPR43-associated disorder, the method comprising administering a therapeutically effective amount of a compound identified as set forth above. The disorder may be, but is not limited to, a disorder relating to fat metabolism, such as obesity, diabetes, atherosclerosis, coronary artery disease, and stroke.

In another aspect, the invention provides a method of identifying a modulator of a TGR18 polypeptide that has G-protein coupled receptor activity and (A) comprises at least 70% amino acid sequence identity to SEQ ID NO:16, (B) comprises at least 50 contiguous amino acids of SEQ ID NO:16, or (C) comprises the amino acid sequence of SEQ ID NO:16; wherein the method comprises: contacting a compound with the polypeptide; and determining the level of activation of the polypeptide by succinic acid in comparison to the level of activation in the absence of the compound. In some embodiments, the TGR18 polypeptide consists of at least 50, often at least 40, 30 or 20, contiguous amino acids of SEQ ID NO:16. Often, the TGR18 is recombinant, e.g., encoded by SEQ ID NO:15. In some embodiments, the step of determining the level of activity may comprise determining the level of binding of the modulator, or the natural ligand, to the TGR18. In other embodiments, the method may comprise detecting an alteration in succinic acid-induced GPCR activity, e.g., a change in GPCR-mediated gene activation, mobilization of intracellular calcium, or an increase in inositol phosphate.

In another aspect, the invention provides a method of identifying a modulator of a TGR164 polypeptide that has G-protein coupled receptor activity and (A) comprises at least 70% amino acid sequence identity to SEQ ID NO:18, (B) comprises at least 50 contiguous amino acids of SEQ ID NO:18, or (C) comprises the amino acid sequence of SEQ ID NO:18; wherein the method comprises: contacting a compound with the polypeptide; and determining the level of activation of the polypeptide by α-ketoglutaric acid in comparison to the level of activation in the absence of the compound. In some embodiments, the TGR164 polypeptide consists of at least 50, often at least 40, 30 or 20, contiguous amino acids of SEQ ID NO:18. Often, the TGR164 is recombinant, e.g., encoded by SEQ ID NO:17. In some embodiments, the step of determining the level of activity may comprise determining the level of binding of the modulator, or the natural ligand, to the TGR164. In other embodiments, the method may comprise detecting an alteration in α-ketoglutaric acid-induced GPCR activity, e.g., a change in GPCR-mediated gene activation, mobilization of intracellular calcium, or an increase in inositol phosphate.

In another embodiment, the invention provides a method of treating a patient with a TGR18 or TGR164-associated disorder, the method comprising administering a therapeutically effective amount of a compound identified as set forth above. The disorder may be, but is not limited to, a kidney-associated disorder, e.g., renal failure, nephritis, glomerulonephritis, hypertension, and other diseases in which the kidney is dysfunctional.

BRIEF DESCRIPTION OF THE DRAWINGS

FIG. 3 provides exemplary data showing that medium and long chain saturated fatty acids activate GPR40.

DETAILED DESCRIPTION OF THE INVENTION AND PREFERRED EMBODIMENTS

Introduction

Figure 1:
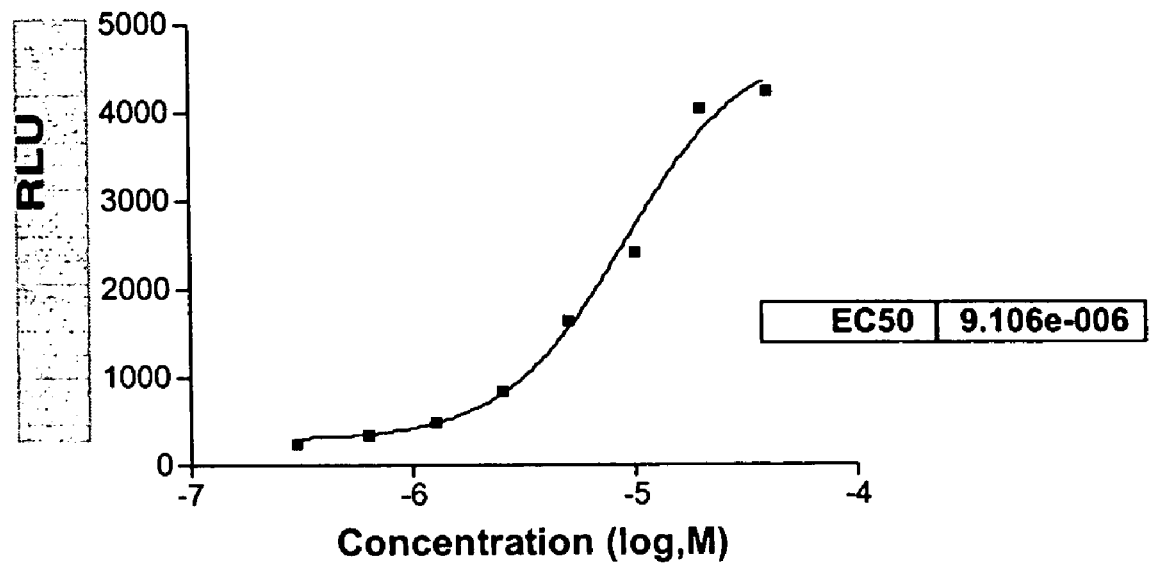
FIG. 1 shows the results of a Aequorin assay using CHO cells transiently transfected with TGR2.

The current invention is based on the discovery of natural ligands for various GPCRs. The inventors have determined that β-alanine is a natural ligand for TGR2; acylation stimulating protein (ASP) is a natural ligand to GPR77; stanniocalcins are natural ligands for LGR4, LGR5, and LGR6; fatty acids that are 6 carbons or greater in length are natural ligands for GPR40, fatty acids of 2–3 carbons in length are natural ligands for GPR43; succinic acid is a natural ligand for TGR18; and α-ketoglutaric acid is a ligand for TGR164. Accordingly, these ligands, or analogs, conservative modifications, or variants thereof, may be used to modulate GPCR activity and for the treatment of diseases or conditions related to GPCR activity. Further, the ligands may be used to identify compounds that modulate ligand binding and activation of the cognate GPCR. Such modulators may be used to treat, for example, TGR2, GPR77, LGR4, LGR5, LGR6, GPR40, GPR43, TGR18, and TGR164-related disorders.

β-alanine is a naturally occurring amino acid that is a precursor of co-enzyme A. It is typically present in synaptic particles and binds to receptors for inhibitor neurotransmitters, e.g., glycine and GABA. Further, it may be released after NMDA receptor stimulation or under cell damaging conditions. Thus, it plays an important role in the nervous system and in the body's response to injury.

ASP is a potent lipogenic factor in mammals that simulates triacylglycerol synthesis. It is identical to the desarginated form of complement C3a, i.e., C3adesArg, but does not bind the C3a receptor (see, e.g., Murray et al., *Biochem J* 342:41–48, 1999; Baldo, et al., *J. Clin. Invest.* 92:1543–1547, 1993). It is believed to play an important role in fat metabolism and diseases such as obesity, diabetes, atherosclerosis and other disorders in lipid metabolism.

Stanniocalcins are involved in mineral metabolism, e.g., calcium and phosphate regulation in mammals as well as other animals, e.g., fish. Two human sequences are known (see, e.g., Chang et al., *Mol. Cell. Endocrinol.* 112:241–247, 1995; WO 95/24411; U.S. Pat. No. 6,008,322; and U.S. Application Publication No. 20020042372). Typically, stanniocalcins can regulate calcium and phosphate transport across mammalian intestinal epithelia. Stanniocalcins are believed to play a role in bone disorders or other disorders related to calcium and phosphate metabolism, as well as growth and reproduction.

The GPCRs GPR41 and GPR42 bind to endogenous fatty acid ligands of 3–5 carbons in length (see, WO 01/61359). The current inventors have discovered that medium and long chain fatty acids, in particular fatty acids having a carbon chain length of six or greater are natural ligands for GPR40, and further, that fatty acids of 2–3 carbons are natural ligands for GPR43.

TGR18 has 38% amino acid identity to P2Y receptors; however, P2Y ligands, e.g., extracellular adenosine nucleotides, do not activate TGR18. Similarly, TGR164 shares 50% amino acid identity with TGR18 and also belongs to the P2Y family of GPCRs. The current inventors have discovered that succinic acid and analogs, e.g., succinic anhydride, maleic acid, oxalacetic acid, methylmalonic acid and itaconic acid are ligands for TGR18; and that α-ketoglutaric acid and analogs, e.g., itaconic acid, are ligands for TGR164.

The present invention thus provides nucleic acids encoding G protein coupled receptors TGR2, GPR77, LGR4, LGR5, LGR6, GPR40, GPR43, TGR18, and TGR164; and natural ligands of these GPCRs. The GPCR nucleic acid and protein sequences provide means for assaying for and identifying modulators of ligand binding and ligand-mediated GPCR signal transduction, e.g., activators, inhibitors, stimulators, enhancers, agonists, and antagonists. Such modulators are useful for pharmacological modulation of signaling pathways, e.g., in cells and tissues that express TGR2, GPR77, LGR4, LGR5, LGR6, GPR40, GPR41, TGR18, or TGR164.

Exemplary TGR2 nucleic acid and protein sequences are provided herein and have been described (see, e.g., WO 01/66750; WO 01/36471; WO 01/83748; WO 01/70814; WO 01/57085; WO 01/48188; EP1178053; WO 01/98330; and WO 01/83555).

Exemplary GPR77 nucleic acid and protein sequences are provided herein and have been described (see, e.g., WO 01/49847; WO 01/62797; WO 01/57085; WO 01/36471; EP1094076; WO 01/48189; WO 01/55338; WO 01/57190; and WO 00/14229).

Exemplary GPR40 nucleic acid and protein sequences are provided herein and have been described (see, e.g., WO 00/22129; and WO 02057783).

Exemplary GPR43 nucleic acid and protein sequences are provided herein and have been described (see, e.g., U.S. Pat. No. 5,910,430; WO 00/22129; WO 99/15656; and WO 98/40483).

Exemplary TGR18 nucleic acid and protein sequences are provided herein and have been described (see, e.g., U.S. Pat. Nos. 5,871,963 and 6,063,582; WO 00/31258; WO 97/24929; WO 00/22131; WO 01/98351; WO 00/61628; and WO 01/79449).

Exemplary TGR164 nucleic acid and protein sequences are provided herein and have been described (see, e.g., WO 01/36471; WO 01/87937; WO 01/49847; WO 01/87980; WO 02/14511; GB2365012; WO 02/46414; EP1219638; WO 01/36473; and WO 0157190).

The GPCRs described herein exhibit patterns of tissue-specific expression. Such tissue specific expression indicates that modulators identified using the methods of the invention can be used to specifically modulate GPCR activity in particular cell types. For example, human TGR2 is expressed in the immune system and in neuronal tissue, e.g., pain sensory neurons. Thus, TGR2 modulators, e.g., β-alanine or other modulators that modulate the level of β-alanine binding to the receptor or β-alanine-induced TGR2 activity, may be used for the treatment of immune or inflammatory disorders, or for the treatment of pain, e.g., chronic or acute pain, including chronic pain syndromes. Pain disorders include, but are not limited, to neuropathic pain resulting from injury to specific nerves; pain associated with cancer, such as pain resulting from bone metastases in cancer, pain associated with chronic or acute inflammatory diseases, and pain associated with chronic ganglionic viral infections, e.g., Herpes infection.

Similarly, GPR77 is expressed in the brain, e.g., the hypothalamus and cortex, adipose and other tissues that are involved in fat metabolism, e.g., liver. Modulators of ASP binding to GPR77 or ASP-induced GPR77 activity can be used, for example, for the treatment of diseases or conditions that involve hypothalamus dysfunction or disorders of fat metabolism, e.g., obesity. LGR4, LGR5, and LGR6 are expressed in various tissues, including reproductive organs. Modulators of stanniocalcin binding or stanniocalcin-induced LGR4, LGR5, or LGR6 activity can be used, for example, for the treatment of diseases or conditions that involve mineral metabolism, e.g., calcium and phosphate metabolism, such as osteoporosis, as well as growth and reproductive disorders.

TGR18 and TGR164 are expressed predominantly in the kidney. Modulators of TGR18 and TGR164 may therefore be used, for example, for the treatment of kidney diseases or diseases related to kidney function. Kidney diseases or diseases related to kidney function include, but are not limited to glomerulonephritis, scarring glomerular disease, renal diseases having an inflammatory component, renal diseases having a glomerular extracellular matrix accumulation component, proteinuria, microaneurysm formation, hypertension, and other diseases that involve renal failure.

Modulators that compete with the binding and/or activity of the particular fatty acid endogenous ligands for GPR 40 and GPR 43 can be used to treat various diseases associated with disorders of fat metabolism including, but not limited to, coronary artery disease, atherosclerosis, thrombosis, obesity, diabetes, stroke, and other vascular diseases.

The GPCR ligands identified herein and modulators of ligand binding and GPCR activity can also be used to further study signal transduction. Thus, the invention provides assays for signal transduction modulation, where the GPCRs act as direct or indirect reporter molecules for the effect of modulators on ligand-mediated signal transduction. GPCRs can be used in assays in vitro, ex vivo, and in vivo, e.g., to measure changes in transcriptional activation of GPCRs; ligand binding; phosphorylation and dephosphorylation; GPCR binding to G-proteins; G-protein activation; regulatory molecule binding; voltage, membrane potential, and conductance changes; ion flux; changes in intracellular second messengers such as cAMP, diacylglycerol, and inositol triphosphate; and changes in intracellular calcium levels.

Methods of assaying for modulators of ligand binding and signal transduction include in vitro ligand binding assays using the GPCRs, portions thereof such as the extracellular domain, or chimeric proteins comprising one or more domains of a GPCR, oocyte GPCR expression or tissue culture cell GPCR expression, either naturally occurring or recombinant; membrane expression of a GPCR, either naturally occurring or recombinant; tissue expression of a GPCR; expression of a GPCR in a transgenic animal, etc.

Related GPCR genes, e.g., from other species should share at least about 70%, 80%, 90%, or greater, amino acid identity over a amino acid region at least about 25 amino acids in length, optionally 50 to 100 amino acids in length.

Specific regions of the GPCR nucleotide and amino acid sequences may be used to identify polymorphic variants, interspecies homologs, and alleles of GPCRs. This identification can be made in vitro, e.g., under stringent hybridization conditions or PCR (using primers that hybridize to SEQ ID NOs:1, 3, 5, 7, 9, 11, 13, 15, or 17), and sequencing, or by using the sequence information in a computer system for comparison with other nucleotide sequences. Typically, identification of polymorphic variants and alleles of a GPCR is made by comparing an amino acid sequence of about 25 amino acids or more, e.g., 50–100 amino acids. Amino acid identity of approximately at least 70% or above, optionally 75%, 80%, 85% or 90–95% or above typically demonstrates that a protein is a polymorphic variant, interspecies homolog, or allele of a GPCR. Sequence comparison is performed using the BLAST and BLAST 2.0 sequence comparison algorithms with default parameters, discussed below. Antibodies that bind specifically to a GPCR or a conserved region thereof can also be used to identify alleles, interspecies homologs, and polymorphic variants. The polymorphic variants, alleles and interspecies homologs are expected to retain the seven transmembrane structure of a G-protein coupled receptor.

Definitions

"GPCR," "TGR", "TGR2", "GPR77", "LGR4", "LGR5", "LGR6", "GPR40", "GPR43", "TGR18", or "TGR164" all refer to G-protein coupled receptors, the genes for most of which have been mapped to particular chromosomes and which are expressed in particular cell types. These GPCRs have seven transmembrane regions and have "G-protein coupled receptor activity," e.g., they bind to G-proteins in response to extracellular stimuli and promote production of second messengers such as diacylglycerol (DAG), $IP_3$, cAMP, and $Ca^{2+}$ via stimulation of downstream effectors such as phospholipase C and adenylate cyclase (for a description of the structure and function of GPCRs, see, e.g., Fong, supra, and Baldwin, supra).

Topologically, GPCRs have an N-terminal "extracellular domain," a "transmembrane domain" comprising seven transmembrane regions and corresponding cytoplasmic and extracellular loops, and a C-terminal "cytoplasmic domain" (see, e.g., Buck & Axel, *Cell* 65:175–187 (1991)). These domains can be structurally identified using methods known to those of skill in the art, such as sequence analysis programs that identify hydrophobic and hydrophilic domains (see, e.g., Kyte & Doolittle, *J. Mol. Biol.* 157: 105–132 (1982)). Such domains are useful for making chimeric proteins and for in vitro assays of the invention.

The terms "GPCR" and "TGR2", "GPR77", "LGR4", "LGR5", "LGR6", "GPR40", "GPR43", "TGR18", or "TGR164" therefore refer to nucleic acid and polypeptide polymorphic variants, alleles, mutants, and interspecies homologs and GPCR domains thereof that: (1) have an amino acid sequence that has greater than about 65% amino acid sequence identity, 70%, 75%, 80%, 85%, 90%, preferably 91%, 92%, 93%, 94%, 95%, 96%, 97%, 98% or 99% or greater amino acid sequence identity, preferably over a window of at least about 25, 50, 100, 200, 500, 1000, or more amino acids, to a sequence of SEQ ID NO:2, 4, 6, 8, 10, 12, 14, 16 or 18; (2) bind to antibodies raised against an immunogen comprising an amino acid sequence of SEQ ID NO:2, 4, 6, 8, 10, 12, 14, 16 or 18 and conservatively modified variants thereof; (3) have at least 15 contiguous amino acids, more often, at least 20, 30, 40, 50, 100, 200, or 300, contiguous amino acids of SEQ ED NO:2, 4, 6, 8, 10, 12, 14, 16 or 18; (4) specifically hybridize (with a size of at least about 100, preferably at least about 500 or 1000 nucleotides) under stringent hybridization conditions to a sequence of SEQ ID NO:1, 3, 5, 7, 9, 11, 13, 15 or 17 and conservatively modified variants thereof; (5) have a nucleic acid sequence that has greater than about 95%, preferably greater than about 96%, 97%, 98%, 99%, or higher nucleotide sequence identity, preferably over a region of at least about 50, 100, 200, 500, 1000, or more nucleotides, to SEQ ID NO:1, 3, 5, 7, 9, 11, 13, 15, or 17; or (6) are amplified by primers that specifically hybridize under stringent conditions to SEQ ID NO:1, 3, 5, 7, 9, 11, 13, 15, or 17. This term also refers to a domain of a GPCR, as described above, or a fusion protein comprising a domain of a GPCR linked to a heterologous protein. A GPCR polynucleotide or polypeptide sequence of the invention is typically from a mammal including, but not limited to, human, mouse, rat, hamster, cow, pig, horse, sheep, or any mammal. A "TGR2, GPR77, LGR4, LGR5, LGR6, GPR40, GPR43, TGR18, or TGR164 polynucleotide" and a "TGR2, GPR77, LGR4, LGR5, LGR6, GPR40, GPR43, TGR18, or TGR164 polypeptide," are both either naturally occurring or recombinant.

A "full length" TGR2, GPR77, LGR4, LGR5, LGR6, GPR40, GPR43, TGR18, or TGR164" protein or nucleic acid refers to a polypeptide or polynucleotide sequence, or a variant thereof, that contains all of the elements normally contained in one or more naturally occurring, wild type TGR2, GPR77, LGR4, LGR5, LGR6, GPR40, GPR43, TGR18, or TGR164 polynucleotide or polypeptide sequences. It will be recognized, however, that derivatives, homologs, and fragments of TGR2, GPR77, LGR4, LGR5, LGR6, GPR40, GPR43, TGR18, or TGR164 can be readily used in the present invention.

In some embodiments, the GPCR used in the methods of the invention is a fragment or domain that essentially consists of, at least 15, often at least 20, 30, 40, or 50, contiguous amino acids of SEQ ID NO:2, 4, 6, 8, 10, 12, 14, 16, or 18.

"Extracellular domain" refers to the domain of a GPCR that protrudes from the cellular membrane and often binds to an extracellular ligand. This domain is often useful for in vitro ligand binding assays, both soluble and solid phase.

"Transmembrane domain," comprises seven transmembrane regions plus the corresponding cytoplasmic and extracellular loops. Certain regions of the transmembrane domain can also be involved in ligand binding.

"Cytoplasmic domain" refers to the domain of a GPCR that protrudes into the cytoplasm after the seventh transmembrane region and continues to the C-terminus of the polypeptide.

The term "β-alanine" refers to a naturally occurring amino acid that is a precursor of co-enzyme A synthesis. A "β-alanine" as used herein includes amino acid analogs and amino acid mimetics that bind to TGR2 and function in a manner similar to the naturally occurring β-alanine. β-alanine is typically present in synaptic particles and binds to receptors for inhibitor neurotransmitters, e.g., glycine and GABA. The molecules are also present in plasma and cerebrospinal fluid (CSF) at μM concentrations.

"Acylation stimulating protein" or "ASP" is identical to the desarginated form of complement C3a, i.e., C3adesArg (see, e.g., Murray et al., *Biochem J.* 342:41–48, 1999; Baldo, et al., *J. Clin. Invest.* 92:1543–1547; 1993). "ASP" sequences are known (e.g., U.S. Pat. No. 5,714,466). As used herein, "ASP" also refers to homologs, variants or mutants that bind to GPR77, but typically not to C3a, and preferably, that stimulate triacylglyceride synthesis as described, for example, in U.S. Pat. No. 5,714,466. Typically, an "ASP" binds to GPR77 and has an amino acid sequence that has greater than about 65% amino acid sequence identity, often 70%, 75%, 80%, 85%, 90%, preferably 91%, 92%, 93%, 94%, 95%, 96%, 97%, 98% or 99% or greater amino acid sequence identity to an ASP as set forth in U.S. Pat. No. 5,714,466; or binds to antibodies raised against an immunogen comprising an ASP as set forth in U.S. Pat. No. 5,714,466.

As used herein, "stanniocalcin" refers to a polypeptide, and allelic variants, homologs, mutants and fragments thereof, that binds to LGR4, LGR5, or LGR6; and has an amino acid sequence that has greater than about 65% amino acid sequence identity, often 70%, 75%, 80%, 85%, 90%, preferably 91%, 92%, 93%, 94%, 95%, 96%, 97%, 98% or 99% or greater amino acid sequence identity to the human stanniocalcin sequences shown in FIG. 1 in U.S. Pat. No. 6,008,322; or binds to antibodies raised against an immunogen comprising a human stannniocalcin amino acid sequence shown in FIG. 1 of U.S. Pat. No. 6,008,322.

A "medium or long chain fatty acid" as used herein refers to a fatty acid having a chain length of at least six carbons. Often, a "medium or long chain fatty acid" used in the invention has a chain length greater than six carbons, for example eight, ten, twelve, fourteen, sixteen, eighteen, twenty, or twenty two carbons in length.

A "short chain fatty acid" generally refers to a fatty acid having a chain length of five carbons or less. A "short chain fatty acid" ligand for GPR43 is typically 2–3 carbons in length.

The term "fatty acid" as used herein encompasses both saturated and polyunsaturated fatty acids and isomeric forms, and also includes short, medium, and long chain fatty acids. Examples of fatty acids are set forth in Tables I, II, and III, infra.

TABLE I $CH_3-(CH_2)_f-(CH=CH)_g(CH_2)_hCO_2H$

| Carbons | f | g | h | Acid Name |
|---|---|---|---|---|
| 16 | 5 | 1 | 7 | Palmitoleic |
| 18 | 7 | 1 | 7 | Oleic |
| 18 | 10 | 1 | 4 | Petroselenic |
| 18 | 5 | 1 | 9 | Vaccenic |
| 18 | 3 | 3 | 7 | Punicic |
| 18 | 1 | 4 | 7 | Parinaric |
| 20 | 9 | 1 | 7 | Gadoleic |
| 22 | 9 | 1 | 9 | Cetoleic |

TABLE II $CH_3-(CH_2)_n-(CH=CH-CH_2)_m-(CH_2)_p-CO_2H$

| Carbons | n | m | p | Acid Name |
|---|---|---|---|---|
| 18 | 4 | 2 | 6 | Linoleic |
| 18 | 1 | 3 | 6 | Linolenic |
| 20 | 4 | 4 | 2 | Arachidonic |

TABLE III $CH_3-(CH_2)_w-CO_2H$

| Carbons | w | Acid Name |
|---|---|---|
| 12 | 10 | Lauric |
| 14 | 12 | Myristic |
| 16 | 14 | Palmitic |
| 18 | 16 | Stearic |
| 20 | 18 | Eicosanoic |
| 22 | 20 | Docosanoic |

It will be appreciated that the unsaturated fatty acids occur in isomeric forms due to the presence of the one or more unsaturated positions. The fatty acids of the present invention are intended to include both the individual double bond isomers as well as mixtures thereof. For example, although, docosatetraenoic acid and docosapentaenoic acid have the same number of carbons, they are different isomeric forms.

A "fibrate" is a member of a class of lipid lowering drugs that are fibric acid derivatives (e.g., gemfibrozil, clofibrate, fenofibrate). The fibric acid derivatives are lipid regulating drugs that promote the catabolism of triglyceride-rich lipoproteins, secondary to the activation of lipoprotein lipase, and promote the reduction of apoC-III synthesis. Fibrates are well known in the art (see, e.g., U.S. Pat. No. 4,058,552).

Examples of the fibrate compounds include bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, etc.

A "TGR18 ligand" as used herein refers to a compound that activates TGR18, such as any alpha,omega-dicarboxylic acid alkane, or precursor thereto or salt thereof, wherein the alkane is a methylene, ethylene or ethenylene group, and wherein the methylene, ethylene and ethenylene groups can be substituted or incorporated into an aromatic or non-aromatic ring. A "TGR18 ligand" is oriented such that it binds to TGR18. Examples of TGR18 ligands include, but are not limited to, succinic acid, succinyl anhydride, maleic acid, oxalacetic acid, methylmalonic acid and itaconic acid. Binding of a TGR18 ligand is typically determined by measuring GPCR activity.

A "TGR164 ligand" as used herein refers to a compounds that activates TGR164, such as any alpha,omega-dicarboxylic acid alkane, or precursor thereto or salt thereof, wherein the alkane is an ethylene or propylene group, and wherein the ethylene and propylene groups can be substituted with suitable substituents, and the ethylene group can be incorporated into a non-aromatic ring. In the TGR164 ligands described herein, the alpha position is substituted with a pi-system such that the pi-system does not hydrogen bond to the carboxylic acid at the omega position, and such that the two carboxylic acids are oriented so as to bind to TGR164. Examples of compounds that activate TGR164 include, but are not limited to, alpha-ketoglutaric acid and itaconic acid. Binding of a TGR164 ligand is typically determined by measuring GPCR activity.

"GPCR activity" refers to the ability of a GPCR to transduce a signal. Such activity can be measured, e.g., in a heterologous cell, by coupling a GPCR (or a chimeric GPCR) to a G-protein and a downstream effector such as PLC or adenylate cyclase, and measuring increases in intracellular calcium (see, e.g., Offermans & Simon, *J. Biol. Chem.* 270:15175–15180 (1995)). Receptor activity can be effectively measured by recording ligand-induced changes in $[Ca^{2+}]_i$ using fluorescent $Ca^{2+}$-indicator dyes and fluorometric imaging. A "natural ligand-induced activity" as used herein, refers to activation of the GPCR by a natural ligand of the GPCR. Activity can be assessed using any number of endpoints to measure the GPCR activity. For example, activity of a GPCR as disclosed herein, such as a TGR2, GPR40, GPR43, TGR18, or TGR164, may be assessed using an assay such as calcium mobilization, e.g., an Aequorin assay, or inositol phosphate accumulation.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as *E. coli*, or eukaryotic cells such as yeast, insect, amphibian, or mammalian cells such as CHO, HeLa, and the like.

"Biological sample" as used herein is a sample of biological tissue or fluid that contains GPCR nucleic acids or polypeptides. Such samples include, but are not limited to, tissue isolated from humans, mice, and rats. Biological samples may also include sections of tissues such as frozen sections taken for histologic purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as chimpanzees or humans. Preferred tissues typically depend on the known expression profile of the GPCR, and include e.g., normal colon, spleen, kidney, liver, hypothalamus, adipose, or other tissues.

The phrase "functional effects" in the context of assays for testing compounds that modulate GPCR-mediated signal transduction includes the determination of any parameter that is indirectly or directly under the influence of a GPCR, e.g., a functional, physical, or chemical effect. It includes ligand binding, changes in ion flux, membrane potential, current flow, transcription, G-protein binding, gene amplification, expression in cancer cells, GPCR phosphorylation or dephosphorylation, signal transduction, receptor-ligand interactions, second messenger concentrations (e.g., cAMP, cGMP, $IP_3$, DAG, or intracellular $Ca^{2+}$), in vitro, in vivo, and ex vivo and also includes other physiologic effects such as increases or decreases of neurotransmitter or hormone release; or increases in the synthesis of particular compounds, e.g., triglycerides.

By "determining the functional effect" is meant assaying for a compound that increases or decreases a parameter that is indirectly or directly under the influence of a GPCR, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, transcriptional activation of GPCRs; ligand binding assays; voltage, membrane potential and conductance changes; ion flux assays; changes in intracellular second messengers such as cAMP and inositol triphosphate ($IP_3$); changes in intracellular calcium levels; neurotransmitter release, and the like.

"Inhibitors," "activators," and "modulators" of GPCRs are used interchangeably to refer to inhibitory, activating, or modulating molecules identified using in vitro and in vivo assays for signal transduction, e.g., ligands, agonists, antagonists, and their homologs and mimetics. Such modulating molecules, also referred to herein as compounds, include polypeptides, antibodies, amino acids, nucleotides, lipids, carbohydrates, or any organic or inorganic molecule. Inhibitors are compounds that, e.g., bind to, partially or totally block stimulation, decrease, prevent, delay activation, inactivate, desensitize, or down regulate signal transduction, e.g., antagonists. Activators are compounds that, e.g., bind to, stimulate, increase, open, activate, facilitate, enhance activation, sensitize or up regulate signal transduction, e.g., agonists. Modulators include compounds that, e.g., alter the interaction of a polypeptide with: extracellular proteins that bind activators or inhibitors; G-proteins; G-protein alpha, beta, and gamma subunits; and kinases. Modulators also include genetically modified versions of GPCRs, e.g., with altered activity, as well as naturally occurring and synthetic ligands, antagonists, agonists, antibodies, small chemical molecules and the like. Such assays for inhibitors and activators include, e.g., expressing GPCRs in vitro, in cells or cell membranes, applying putative modulator compounds, and then determining the functional effects on signal transduction, as described above.

Samples or assays comprising GPCRs that are treated with a potential activator, inhibitor, or modulator are compared to control samples without the inhibitor, activator, or modulator to examine the extent of inhibition. Activation of a GPCR is achieved when the GPCR activity value relative to the control (untreated with activators) is 110%, more preferably 150%, more preferably 200–500% (i.e., two to five fold higher relative to the control), more preferably 1000–3000% higher. For determing inhibitor activity, control samples (untreated with inhibitors) are assigned a relative GPCR activity value of 100%. Inhibition of a GPCR is achieved when the GPCR activity value relative to the control is about 80%, preferably 50%, more preferably 25–0%.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated GPCR nucleic acid is separated from open reading frames that flank the GPCR gene and encode proteins other than the GPCR. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Biologically active" GPCR refers to a GPCR having signal transduction activity and G protein coupled receptor activity, as described above.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V);

6) Phenylalanine (F), Tyrosine (Y), Tryptophan (W);

7) Serine (S), Threonine (T); and

8) Cysteine (C), Methionine (M)

(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3rd ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radiolabel into the peptide, and used to detect antibodies specifically reactive with the peptide).

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the complement of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1994–1999).

A preferred example of algorithms that are suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec–2 min., an annealing phase lasting 30 sec.–2 min., and an extension phase of about 72° C. for 1–2 min.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and hetero- meric Fab fragments that specifically bind to selected antigens (see, e.g., McCafferty et al., *Nature* 348:552–554 (1990); Marks et al., *Biotechnology* 10:779–783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-GPCR" antibody is an antibody or antibody fragment that specifically binds a polypeptide encoded by a GPCR gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a particular GPCR can be selected to obtain only those polyclonal antibodies that are specifically immunoreactive with the GPCR, and not with other proteins, except for polymorphic variants, orthologs, and alleles of the GPCR. This selection may be achieved by subtracting out antibodies that cross-react with GPCR molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background. Antibodies that react only with a particular GPCR ortholog, e.g., from specific species such as rat, mouse, or human, can also be made as described above, by subtracting out antibodies that bind to the same GPCR from another species.

The phrase "selectively associates with" refers to the ability of a nucleic acid to "selectively hybridize" with another as defined above, or the ability of an antibody to "selectively (or specifically) bind" to a protein, as defined above.

Isolation of Nucleic Acids Encoding GPCRs

A. General Recombinant DNA Methods

This invention relies on routine techniques in the field of recombinant genetics. Basic texts disclosing the general methods of use in this invention include Sambrook & Russell, *Molecular Cloning, A Laboratory Manual* (3rd Ed, 2001); Kriegler, *Gene Transfer and Expression: A Labora-* tory Manual (1990); and Current Protocols in Molecular Biology (Ausubel et al., eds., 1994–1999). Methods that are used to produce GPCRs for use in the invention may also be employed to produce protein ligands, e.g., stanniocalcins, ASP, or polypeptides that modulate ligand binding to the receptor, for use in the invention.

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

B. Cloning Methods for the Isolation of Nucleotide Sequences Encoding GPCRs

In general, the nucleic acid sequences encoding GPCRs and related nucleic acid sequence homologs are cloned from cDNA and genomic DNA libraries by hybridization with a probe, or isolated using amplification techniques with oligonucleotide primers, and verified by sequencing. For example, GPCR sequences are typically isolated from mammalian nucleic acid (genomic or cDNA) libraries by hybridizing with a nucleic acid probe, the sequence of which can be derived from SEQ ID NO:1, 3, 5, 7, 9, 11, 13, 15, or 17. Suitable tissues from which GPCR RNA and cDNA can be isolated include, e.g., neural tissue, e.g., peripheral neural tissue and brain; immune cells and tissues, e.g., spleen, lymphocytes, bone marrow, and the like; adipose tissue; bone tissue; and other tissues.

Amplification techniques using primers can also be used to amplify and isolate GPCR nucleic acids from DNA or RNA. Suitable primers can be designed using criteria well known in the art (see, e.g., Dieffenbach & Dveksler, *PCR Primer: A Laboratory Manual* (1995)). These primers can be used, e.g., to amplify either the full length sequence or a probe of one to several hundred nucleotides, which is then used to screen a mammalian library for full-length GPCRs.

Nucleic acids encoding GPCRs can also be isolated from expression libraries using antibodies as probes. Such polyclonal or monoclonal antibodies can be raised using the sequence of SEQ ID NO:2, 4, 6, 8, 10, 12, 14, 16, or 18.

GPCR polymorphic variants, alleles, and interspecies homologs that are substantially identical to a GPCR can be isolated using GPCR nucleic acid probes, and oligonucleotides under stringent hybridization conditions, by screening libraries. Alternatively, expression libraries can be used to clone GPCRs and GPCR polymorphic variants, alleles, and interspecies homologs, by detecting expressed homologs immunologically with antisera or purified antibodies made against GPCRs, which also recognize and selectively bind to the GPCR homolog. Methods of constructing cDNA and genomic libraries are well known in the art (see, e.g., Sambrook & Russell, supra; and Ausubel et al., supra).

An alternative method of isolating GPCR nucleic acids and their homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of GPCRs directly from mRNA, from cDNA, from genomic libraries or cDNA libraries. Degenerate oligonucleotides can be designed to amplify GPCR homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of GPCR-encoding mRNA in physiological samples, for nucleic acid sequencing, or for other purposes. Genes amplified by the PCR reaction can be purified from agarose gels and cloned into an appropriate vector.

Gene expression can also be analyzed by techniques known in the art, e.g., reverse transcription and amplification of mRNA, isolation of total RNA or poly $A^+$ RNA, northern blotting, dot blotting, in situ hybridization, RNase protection, probing DNA microchip arrays, and the like. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

Synthetic oligonucleotides can be used to construct recombinant GPCR genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the GPCR nucleic acid. The specific subsequence is then ligated into an expression vector.

The nucleic acid encoding a GPCR is typically cloned into intermediate vectors before transformation into prokaryotic or eukaryotic cells for replication and/or expression. These intermediate vectors are typically prokaryote vectors, e.g., plasmids, or shuttle vectors.

Optionally, nucleic acids encoding chimeric proteins comprising GPCRs or domains thereof can be made according to standard techniques. For example, a domain such as ligand binding domain, an extracellular domain, a transmembrane domain (e.g., one comprising seven transmembrane regions and corresponding extracellular and cytosolic loops), the transmembrane domain and a cytoplasmic domain, an active site, a subunit association region, etc., can be covalently linked to a heterologous protein. For example, an extracellular domain can be linked to a heterologous GPCR transmembrane domain, or a heterologous GPCR extracellular domain can be linked to a transmembrane domain. Other heterologous proteins of choice include, e.g., green fluorescent protein, luciferase, or β-gal.

C. Expression in Prokaryotes and Eukaryotes

To obtain high level expression of a cloned gene or nucleic acid, such as cDNAs encoding GPCRs, or a protein ligand, one typically subclones a nucleic acid sequence encoding the protein of interest into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook & Russell and Ausubel et al. Bacterial expression systems for expressing the protein are available in, e.g., *E. coli, Bacillus* sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the GPCR encoding nucleic acid in host cells. A typical expression cassette thus contains a promoter operably linked to the nucleic acid sequence encoding a GPCR and signals required for efficient polyadenylation of the transcript, ribosome binding sites, and translation termination. The nucleic acid sequence encoding a GPCR may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a GPCR-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of GPCR protein, which are then purified using standard techniques (see, e.g., Colley et al., *J. Biol. Chem.* 264:17619–17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Russell & Sambrook, supra). It is only necessary that the particular genetic engineering procedure used be capable of successfully introducing at least one gene into the host cell capable of expressing a GPCR.

After the expression vector is introduced into the cells, the transfected cells are cultured under conditions favoring expression of a GPCR, which is recovered from the culture using standard techniques identified below.

Transgenic animals, including knockout transgenic animals, that include additional copies of a GPCR and/or altered or mutated GPCR transgenes can also be generated. A "transgenic animal" refers to any animal (e.g. mouse, rat, pig, bird, or an amphibian), preferably a non-human mammal, in which one or more cells contain heterologous nucleic acid introduced using transgenic techniques well known in the art. The nucleic acid is introduced into the cell, directly or indirectly, by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA.

In other embodiments, transgenic animals are produced in which expression of a GPCR is silenced. Gene knockout by homologous recombination is a method that is commonly used to generate transgenic animals. Transgenic mice can be derived using methodology known to those of skill in the art, see, e.g., Hogan et al., *Manipulating the Mouse Embryo: A*

*Laboratory Manual*, (1988); *Teratocarcinomas and Embryonic Stem Cells: A Practical Approach*, Robertson, ed., (1987); and Capecchi et al., *Science* 244:1288 (1989).

Purification of GPCRs

Either naturally occurring or recombinant GPCRs can be purified for use in functional assays. Optionally, recombinant GPCRs are purified. Naturally occurring GPCRs are purified, e.g., from any suitable tissue or cell expressing naturally occurring GPCRs. Recombinant GPCRs are purified from any suitable bacterial or eukaryotic expression system, e.g., CHO cells or insect cells.

A GPCR may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Russell & Sambrook, supra).

A number of procedures can be employed when a recombinant GPCR is being purified. For example, proteins having established molecular adhesion properties can be reversibly fused to a GPCR. With the appropriate ligand, a GPCR can be selectively adsorbed to a purification column and then freed from the column in a relatively pure form. The fused protein is then removed by enzymatic activity. Finally, a GPCR could be purified using immunoaffinity columns.

Recombinant proteins are expressed by transformed bacteria or eukaryotic cells such as CHO cells or insect cells in large amounts, typically after promoter induction; but expression can be constitutive. Promoter induction with IPTG is one example of an inducible promoter system. Cells are grown according to standard procedures in the art. Fresh or frozen cells are used for isolation of protein using techniques known in the art (see, e.g., Russell & Sambrook, supra; and Ausubel et al., supra).

Immunological Detection of GPCRs

In addition to the detection of GPCR genes and gene expression using nucleic acid hybridization technology, one can also use antibodies to detect GPCRs that are used in the invention. A general overview of the applicable technology can be found in Harlow & Lane, *Antibodies: A Laboratory Manual* (1988) and Harlow & Lane, *Using Antibodies* (1999). Again, these methods are also applicable to the preparation and use of antibodies for other polypeptides used in this invention, e.g., ASP or stanniocalcin.

Methods of producing polyclonal and monoclonal antibodies that react specifically with GPCRs are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)). Such antibodies can be used for therapeutic and diagnostic applications, e.g., in the treatment and/or detection of any of the GPCR-associated diseases or conditions described herein.

A number of GPCRs comprising immunogens may be used to produce antibodies specifically reactive with GPCRs. For example, a recombinant GPCR or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used as an immunogen. Naturally occurring protein may also be used either in pure or impure fomm. The product is then injected into an animal capable of producing antibodies. Either monoclonal or polyclonal antibodies may be generated, for subsequent use in immunoassays to measure the protein.

Typically, polyclonal antisera with a titer of $10^4$ or greater are selected and tested for their cross reactivity against non-GPCR proteins or even other related proteins from other organisms, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better.

Once GPCR specific antibodies are available, GPCRs can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

GPCRs can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the GPCR or antigenic subsequence thereof).

Immunoassays also often use a labeling agent to specifically bind to and label the complex formed by the antibody and antigen. The labeling agent may itself be one of the moieties comprising the antibody/antigen complex. Thus, the labeling agent may be a labeled GPCR polypeptide or a labeled anti-GPCR antibody. Alternatively, the labeling agent may be a third moiety, such as a secondary antibody, that specifically binds to the antibody/GPCR complex (a secondary antibody is typically specific to antibodies of the species from which the first antibody is derived). Other proteins capable of specifically binding immunoglobulin constant regions, such as protein A or protein G may also be used as the labeling agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Commonly used assays include noncompetitive assays, e.g., sandwich assays, and competitive assays. In competitive assays, the amount of GPCR present in the sample is measured indirectly by measuring the amount of a known, added (exogenous) GPCR displaced (competed away) from an anti-GPCR antibody by the unknown GPCR present in a sample. Commonly used assay formats include Western blots (immunoblots), which are used to detect and quantify the presence of protein in a sample. Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize GPCRs, or secondary antibodies that recognize anti-GPCR.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Cross-Reactivity Determinations

Immunoassays in the competitive binding format can also be used for cross-reactivity determinations. For example, a protein at least partially encoded by SEQ ID NO:1, 3, 5, 7, 9, 11, 13, 15, or 17 can be immobilized to a solid support. Proteins (e.g., GPCR proteins and homologs) are added to the assay that compete for binding of the antisera to the immobilized antigen. The ability of the added proteins to compete for binding of the antisera to the immobilized protein is compared to the ability of GPCRs encoded by SEQ ID NO:1, 3, 5, 7, 9, 11, 13, 15, or 17 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a GPCR, to the immunogen protein (i.e., the GPCR of SEQ ID NO:2, 4, 6, 8, 10, 12, 14, 16, or 18). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:1, 3, 5, 7, 9, 11, 13, 15, or 17 that is required to inhibit 50% of binding, then the second protein is said to specifically bind to the polyclonal antibodies generated to a GPCR immunogen.

Assays for Modulators of GPCRs

A. Assays for GPCR Activity

GPCRs and their alleles and polymorphic variants are G-protein coupled receptors that participate in signal transduction and are associated with cellular function in a variety of cells, e.g., neurons, immune system cells, kidney, liver, colon, adipose, and other cells. The activity of GPCR polypeptides can be assessed using a variety of in vitro and in vivo assays to determine functional, chemical, and physical effects, e.g., measuring ligand binding, (e.g., radioactive ligand binding), second messengers (e.g., cAMP, cGMP, IP$_3$, DAG, or Ca$^{2+}$), ion flux, phosphorylation levels, transcription levels, neurotransmitter levels, and the like. Such assays can be used to test for inhibitors and activators of a GPCR. In particular, the assays can be used to test for compounds that modulate natural ligand-induced GPCR activity, for example, by modulating the binding of the natural ligand to the receptor and/or by modulating the ability of the natural ligand to activate the receptor. Typically in such assays, the test compound is contacted with the GPCR in the presence of the natural ligand. The natural ligand may be added to the assay before, after, or concurrently with the test compound. The results of the assay, for example, the level of binding, calcium mobilization, etc. is then compared to the level in a control assay that comprises the GPCR and natural ligand in the absence of the test compound.

Screening assays of the invention are used to identify modulators that can be used as therapeutic agents, e.g., antibodies to GPCRs and antagonists of GPCR activity.

The effects of test compounds upon the function of the GPCR polypeptides can be measured by examining any of the parameters described above. Any suitable physiological change that affects GPCR activity can be used to assess the influence of a test compound on the GPCRs and natural ligand-mediated GPCR activity. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, $IP_3$ or cAMP.

For a general review of GPCR signal transduction and methods of assaying signal transduction, see, e.g., *Methods in Enzymology*, vols. 237 and 238 (1994) and volume 96 (1983); Bourne et al., *Nature* 10:349:117–27 (1991); Bourne et al., *Nature* 348:125–32 (1990); Pitcher et al., *Annu. Rev. Biochem.* 67:653–92 (1998).

The GPCR of the assay will be selected from a polypeptide having a sequence of SEQ ID NO:2, 4, 6, 8, 10, 12, 14, 16, or 18, or conservatively modified variants thereof. Alternatively, the GPCR of the assay will be derived from a eukaryote and include an amino acid subsequence having amino acid sequence identity to SEQ ID NO:2, 4, 6, 8, 10, 12 14, 16 or 18. Generally, the amino acid sequence identity will be at least 70%, optionally at least 80%, optionally at least 90–95%. Optionally, the polypeptide of the assays will comprise or consist of a domain of a GPCR, such as an extracellular domain, transmembrane domain, cytoplasmic domain, ligand binding domain, subunit association domain, active site, and the like. Either a GPCR or a domain thereof can be covalently linked to a heterologous protein to create a chimeric protein used in the assays described herein.

Modulators of GPCR activity are tested using GPCR polypeptides as described above, either recombinant or naturally occurring. The protein can be isolated, expressed in a cell, expressed in a membrane derived from a cell, expressed in tissue or in an animal, either recombinant or naturally occurring. For example, neurons, cells of the immune system, adipocytes, kidney cells, transformed cells, or membranes can be used. Modulation is tested using one of the in vitro or in vivo assays described herein. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of the protein of interest can be used in vitro in soluble or solid state reactions to assay for ligand binding.

Ligand binding to a GPCR, a domain, or chimeric protein can be tested in a number of formats. For example, binding can be performed in solution, in a bilayer membrane, attached to a solid phase, in a lipid monolayer, or in vesicles. Typically, in an assay of the invention, the binding of the natural ligand to its receptor is measured in the presence of a candidate modulator. Alternatively, the binding of the candidate modulator may be measured in the presence of the natural ligand. Often, competitive assay that measure the ability of a compound to compete with binding of the natural ligand to the receptor are used. Binding may be measured by assessing GPCR activity or by other assays: binding can be tested by measuring e.g., changes in spectroscopic characteristics (e.g., fluorescence, absorbance, refractive index), hydrodynamic (e.g., shape) changes, or changes in chromatographic or solubility properties.

Receptor-G-protein interactions can also be used to assay for modulators. For example, in the absence of GTP, binding of an activator such as the natural ligand will lead to the formation of a tight complex of a G protein (all three subunits) with the receptor. This complex can be detected in a variety of ways, as noted above. Such an assay can be modified to search for inhibitors. For example, the ligand can be added to the receptor and G protein in the absence of GTP to form a tight complex. Inhibitors may be identified by looking at dissociation of the receptor-G protein complex. In the presence of GTP, release of the alpha subunit of the G protein from the other two G protein subunits serves as a criterion of activation.

An activated or inhibited G-protein will in turn alter the properties of downstream effectors such as proteins, enzymes, and channels. The classic examples are the activation of cGMP phosphodiesterase by transducin in the visual system, adenylate cyclase by the stimulatory G-protein, phospholipase C by $G_q$ and other cognate G proteins, and modulation of diverse channels by Gi and other G proteins. Downstream consequences such as generation of diacyl glycerol and $IP_3$ by phospholipase C, and in turn, for calcium mobilization e.g., by $IP_3$ (further discussed below) can also be examined. Thus, modulators can be evaluated for the ability to stimulate or inhibit ligand-mediated downstream effects. For example, β-alanine specifically activates TGR2 in inositol phosphate accumulation and calcium mobilization, e.g., aequorin, assays. Similarly, GPR40 and GPR43 are activated in aequorin assays when bound by the fatty acid ligands disclosed herein; and TGR18 and TGR164 are activated by short chain carboxylic acids in calcium mobilization assays and inositol phosphate assays. Candidate modulators may be assessed for the ability to inhibit inositol phosphate accumulation and/or calcium mobilization induced by the natural ligand, e.g., β-alanine (TGR2), a 2–3 carbon chain fatty acid (GPR43), a medium or long chain fatty acid (GPR40), succinic acid (TGR18), or a-ketoglutaric acid (TGR164).

In other examples, the ability of a modulator to activate a GPR expressed in adipocytes, e.g., GPR43, in comparison to the ability of a natural ligand fatty acid, may be determined using assays such as lipolysis (see, e.g., WO01/61359).

Activated GPCRs become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors.

Modulators may therefore also be identified using assays involving β-arrestin recruitment. β-arrestin serves as a regulatory protein that is distributed throughout the cytoplasm in unactivated cells. Ligand binding to an appropriate GPCR is associated with redistribution of β-arrestin from the cytoplasm to the cell surface, where it associates with the GPCR. Thus, receptor activation and the effect of candidate modulators on ligand-induced receptor activation, can be assessed by monitoring β-arrestin recruitment to the cell surface. This is frequently performed by transfecting a labeled β-arrestin fusion protein (e.g., β-arrestin -green fluorescent protein (GFP)) into cells and monitoring its distribution using confocal microscopy (see, e.g., Groarke et al., *J. Biol. Chem.* 274(33):23263–69 (1999)).

Receptor internalization assays may also be used to assess receptor function. Upon ligand binding, the G-protein coupled receptor—ligand complex is internalized from the plasma membrane by a clathrin-coated vesicular endocytic process; internalization motifs on the receptors bind to adaptor protein complexes and mediate the recruitment of the activated receptors into clathrin-coated pits and vesicles. Because only activated receptors are internalized, it is possible to detect ligand-receptor binding by determining the amount of internalized receptor. In one assay format, cells are transiently transfected with radiolabeled receptor and incubated for an appropriate period of time to allow for ligand binding and receptor internalization. Thereafter, surface-bound radioactivity is removed by washing with an acid solution, the cells are solubilized, and the amount of internalized radioactivity is calculated as a percentage of ligand binding. See, e.g., Vrecl et al., *Mol. Endocrinol.* 12:1818–29 (1988) and Conway et al., *J. Cell Physiol.* 189(3):341–55 (2001). In addition, receptor internalization approaches have allowed real-time optical measurements of GPCR interactions with other cellular components in living cells (see, e.g., Barak et al., *Mol. Pharmacol.* 51(2)177–84 (1997)). Modulators may be identified by comparing receptor internalization levels in control cells and cells contacted with candidate compounds. For example, candidate modulators are assayed by examining their effects on receptor internalization upon binding of the natural ligand, β-alanine, ASP, stanniocalcin, a medium or long chain fatty acid, or a 2–3 carbon chain fatty acid, succinic acid, or α-ketoglutaric acid to its cognate receptor, i.e., TGR2; GPR77; or LGR4, LGR5, LGR6, GPR40, GPR43, TGR18, or TGR164; respectively.

Another technology that can be used to evaluate GPCR-protein interactions in living cells involves bioluminescence resonance energy transfer (BRET). A detailed discussion regarding BRET can be found in Kroeger et al., *J. Biol. Chem.*, 276(16):12736–43 (2001).

Receptor-stimulated guanosine 5'-O-(γ-Thio)-Triphosphate ([$^{35}$S]GTP-γS) binding to G-proteins may also be used as an assay for evaluating modulators of GPCRs. [$^{35}$S] GTPγS is a radiolabeled GTP analog that has a high affinity for all types of G-proteins, is available with a high specific activity and, although unstable in the unbound form, is not hydrolyzed when bound to the G-protein. Thus, it is possible to quantitatively assess ligand-bound receptor by comparing stimulated versus unstimulated [$^{35}$S]GTPγS binding utilizing, for example, a liquid scintillation counter. Inhibitors of the receptor-ligand interactions would result in decreased [$^{35}$S]GTPγs binding. Descriptions of [$^{35}$S]GTPγS binding assays are provided in Traynor and Nahorski, *Mol. Pharmacol.* 47(4):848–54 (1995) and Bohn et al., *Nature* 408: 720–23 (2000).

The ability of modulators to affect ligand-induced ion flux may also be determined. Ion flux may be assessed by determining changes in polarization (i.e., electrical potential) of the cell or membrane expressing a GPCR. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include: radiolabeled ion flux assays and fluorescence assays using voltage-sensitive dyes (see, e.g., Vestergarrd-Bogind et al., *J. Membrane Biol.* 88:67–75 (1988); Gonzales & Tsien, *Chem. Biol.* 4:269–277 (1997); Daniel et al., *J. Pharmacol. Meth.* 25:185–193 (1991); Holevinsky et al., *J. Membrane Biology* 137:59–70 (1994)). Generally, the compounds to be tested are present in the range from 1 pM to 100 mM.

Preferred assays for G-protein coupled receptors include cells that are loaded with ion or voltage sensitive dyes to report receptor activity. Assays for determining activity of such receptors can also use known agonists and antagonists for other G-protein coupled receptors and the natural ligands disclosed herein as negative or positive controls to assess activity of tested compounds. In assays for identifying modulatory compounds (e.g., agonists, antagonists), changes in the level of ions in the cytoplasm or membrane voltage are monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as Gα15 and Gα16 can be used in the assay of choice (Wilkie et al., *Proc. Nat'l Acad. Sci. USA* 88:10049–10053 (1991)). Such promiscuous G-proteins allow coupling of a wide range of receptors to signal transduction pathways in heterologous cells.

As noted above, receptor activation by ligand binding typically initiates subsequent intracellular events, e.g., increases in second messengers such as $IP_3$, which releases intracellular stores of calcium ions. Activation of some G-protein coupled receptors stimulates the formation of inositol triphosphate ($IP_3$) through phospholipase C-mediated hydrolysis of phosphatidylinositol (Berridge & Irvine, *Nature* 312:315–21 (1984)). $IP_3$ in turn stimulates the release of intracellular calcium ion stores. Thus, a change in cytoplasmic calcium ion levels, or a change in second messenger levels such as $IP_3$ can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated by ligand binding, result in a change in the level of intracellular cyclic nucleotides, e.g., cAMP or cGMP, by activating or inhibiting downstream effectors such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Natl. Acad. Sci. U.S.A.* 88:9868–9872 (1991) and Dhallan et al., *Nature* 347:184–187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In one embodiment, changes in intracellular cAMP or cGMP can be measured using immunoassays. The method described in Offermanns & Simon, *J. Biol. Chem.* 270: 15175–15180 (1995) may be used to determine the level of cAMP. Also, the method described in Felley-Bosco et al., *Am. J. Resp. Cell and Mol. Biol.* 11:159–164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with $^3$H-myoinositol for 48 or more hrs. The labeled cells are treated with a test compound for one hour. The treated cells are lysed and extracted in chloroform-methanol-water after which the inositol phosphates are separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on ligand-induced signal transduction. A host cell containing the protein of interest is contacted with a test compound in the presence of the natural ligand for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter genes may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961–964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

Samples that are treated with a potential GPCR inhibitor or activator are compared to control samples comprising the natural ligand without the test compound to examine the extent of modulation. Control samples (untreated with activators or inhibitors) are assigned a relative GPCR activity value of 100. Inhibition of a GPCR is achieved when the GPCR activity value relative to the control is about 90%, optionally 50%, optionally 25–0%. Activation of a GPCR is achieved when the GPCR activity value relative to the control is 110%, optionally 150%, 200–500%, or 1000–2000%.

B. Modulators

The compounds tested as modulators of GPCRs can be any small chemical compound, or a biological entity, e.g., a macromolecule such as a protein, sugar, nucleic acid or lipid. Alternatively, modulators can be genetically altered versions of a GPCR. Typically, test compounds will be small chemical molecules and peptides. Essentially any chemical compound can be used as a potential modulator or ligand in the assays of the invention, although most often compounds can be dissolved in aqueous or organic (especially DMSO-based) solutions. The assays are designed to screen large chemical libraries by automating the assay steps. The assays are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Russell & Sambrook, all supra), peptide nucleic acid libraries (see, e.g., U.S. Pat. No. 5,539, 083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

C. Solid State and Soluble High Throughput Assays

In one embodiment the invention provides soluble assays using molecules such as a domain, e.g., a ligand binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; a GPCR; or a cell or tissue expressing a GPCR, either naturally occurring or recombinant. In another embodiment, the invention provides solid phase based in vitro assays in a high throughput format, where the domain, chimeric molecule, GPCR, or cell or tissue expressing a GPCR is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100–1500 different compounds. It is possible to assay several different plates per day; assay screens for up to about 6,000–20,000 different compounds is possible using the integrated systems of the invention.

The molecule of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the signal transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and are appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:19). Such flexible linkers are known to persons of skill in the art. For example, poly (ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

D. Computer-Based Assays

Yet another assay for compounds that modulate GPCR activity involves computer assisted drug design, in which a computer system is used to generate a three-dimensional structure of GPCR based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify the regions that have the ability to bind, e.g., ligands. These regions are then used to identify various compounds that modulate ligand-receptor binding.

The three-dimensional structural model of the protein is generated by entering protein amino acid sequences of at least 10 amino acid residues or corresponding nucleic acid sequences encoding a GPCR polypeptide into the computer system. The amino acid sequence of the polypeptide or the nucleic acid encoding the polypeptide is selected from the group consisting of SEQ ID NO: 2, 4, 6, 8, 10, 12, 14, 16, or 18; or SEQ ID NO: 1, 3, 5, 7, 9, 11, 13, 15, or 17, respectively, and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the GPCR protein to identify ligands that bind to GPCR. Binding affinity between the protein and ligands is determined using energy terms to determine which ligands have an enhanced probability of binding to the protein.

Computer systems are also used to screen for mutations, polymorphic variants, alleles and interspecies homologs of GPCR genes. Such mutations can be associated with disease states or genetic traits. As described above, GeneChip™ and related technology can also be used to screen for mutations, polymorphic variants, alleles and interspecies homologs. Once the variants are identified, diagnostic assays can be used to identify patients having such mutated genes. Identification of the mutated GPCR genes involves receiving input of a first nucleic acid or amino acid sequence encoding an GPCR, selected from the group consisting of SEQ ID NO:1, 3, 5, 7, 9, 11, 13, 15, or 17; or SEQ ID NO:2, 4, 6, 8, 10, 12, 14, 16, or 18, respectively, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in GPCR genes, and mutations associated with disease states and genetic traits.

E. Expression Assays

Certain screening methods involve screening for a compound that modulate the expression of the GPCRs described herein, or the levels of natural ligands, e.g., ASP and stanniocalcins. Such methods generally involve conducting cell-based assays in which test compounds are contacted with one or more cells expressing the GPCR or ligand and then detecting an increase or decrease in expression (either transcript or translation product). Such assays are typically performed with cells that express the endogenous GPCR or ligand.

Expression can be detected in a number of different ways. As described herein, the expression levels of the protein in a cell can be determined by probing the mRNA expressed in a cell with a probe that specifically hybridizes with a transcript (or complementary nucleic acid derived therefrom) of the GPCR or protein ligand. Probing can be conducted by lysing the cells and conducting Northern blots or without lysing the cells using in situ-hybridization techniques (see above). Alternatively, protein can be detected using immunological methods in which a cell lysate is probed with antibodies that specifically bind to the protein.

Other cell-based assays are reporter assays conducted with cells that do not express the protein. Certain of these assays are conducted with a heterologous nucleic acid construct that includes a promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, CAT (chloramphenicol acetyl transferase), luciferase, β-galactosidase and alkaline phosphatase.

In these assays, cells harboring the reporter construct are contacted with a test compound. A test compound that either modulates the activity of the promoter by binding to it or triggers a cascade that produces a molecule that modulates the promoter causes expression of the detectable reporter. Certain other reporter assays are conducted with cells that harbor a heterologous construct that includes a transcriptional control element that activates expression of the GPCR or ligand and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

Kits

GPCRs and their homologs are a useful tool for identifying cells such as immune cells, adipose, or neural cells, for forensics and paternity determinations, for diagnosing diseases, and for examining signal transduction. GPCR-specific reagents that specifically bind to a GPCR protein, e.g., the ligand, or GPCR antibodies are used to examine signal transduction regulation.

The present invention also provides for kits for screening for modulators of ligand-GPCR interactions. Such kits can be prepared from readily available materials and reagents. For example, such kits can comprise any one or more of the following materials: a GPCR, reaction tubes, and instructions for testing GPCR activity. Optionally, the kit contains biologically active GPCR. A wide variety of kits and components can be prepared according to the present invention, depending upon the intended user of the kit and the particular needs of the user.

Disease Treatment and Diagnosis

TGRs are involved in the regulation of many important physiological functions and are often therapeutic targets for various diseases or conditions. Mammalian TGRs are typically classified in three categories, class A, receptors related to rhodopsin and the adrenergic receptors, class B, receptors related to the calcitonin and parathyroid hormone receptors, and class C, receptors related to the metabotropic receptors. The rhodopsin/adrenergic receptor class is the largest class and includes various amine receptor, e.g., acetylcholine (muscarinic) receptors, adrenergic receptors, dopamine receptors, histamine receptors, serotonin receptors, and octopamine receptors; peptide receptors, e.g., angiotensin, bombesin, bradykinin, endothelin, interleukin-8, chemokine, melanocortin, neuropeptide Y, neurotensin, opioid, somatostatin, tachykinin, thrombin, vasopressin, galanin, proteinase-activated, orexin, and chemokine/chemotatic factor receptors; protein hormone receptors, e.g., FSH, lutropin-choriogonadotropic hormone, and thyrotropin receptors; rhodopsin receptors; olfactory receptors; prostanoid receptors; nucleotide-like receptors, including adenosine and purinoceptors; *cannabis* receptors; platelet activating factor receptor; gonadotropin-releasing hormone receptor; melatonin receptor, lysosphingolipid and LPA (EDG) receptors, as well as various orphan receptors. Class B includes calcitonin, corticotropin releasing factor, gastric inhibitory peptide glucagon, growth hormone-releasing hormone, parathyroid hormone, PACAP, secretin, vasoactive intestinal polypeptide, and brain-specific angiogenesis inhibitor receptors, among others. Class C receptors include metabotropic glutamate receptors and GABA-B subtype receptors as well as putative pheromone receptors.

Class A GPCRs function in a variety of physiological processes such as vasodilation, bronchodilation, neurotransmitter signaling, stimulation of endocrine secretions, gut peristalsis, development, mitogenesis, cell proliferation, cell migration, immune system function, and oncogenesis. Accordingly, class A GPCRs can be used, for example, as probes to identify cells or tissues that exhibit dysregulation of these processes, and moreover, as screening targets to identify modulators of these processes.

Class B GPCRs also function in a wide range of physiological processes such as regulation of calcium homeostasis, modulation of activity of cells in the immune system, various excitatory and inhibitory actions in the central nervous system, control of smooth muscle relaxation, control of smooth muscle, secretion in stomach, intestinal epithelium, pancreas, and gall bladder. Accordingly, class B GPCRs can be used, for example, as probes to identify cells or tissues that exhibit dyregulation of these process, and to identify modulators of these physiological processes.

Class C GPCRs, metabotropic glutamate receptors, are also important regulators of physiological processes such as neurotransmission. Glutamate is the major neurotransmitter in the CNS and plays an important role in neuronal plasticity, cognition, memory, learning, and some neurological disorders such as epilepsy, stroke, and neurodegeneration. B-type receptors for the neurotransmitter GABA (gamma-aminobutyric acid) inhibit neuronal activity through G-protein-coupled second-messenger systems, which regulate the release of neurotransmitters and the activity of ion channels and adenylyl cyclase. Thus, GABA B-type receptors play a role in controlling neuronal function and are also involved in such processes as neuronal plasticity, cognition, memory, and learning. Accordingly, class C GPCRs can be used, for example, as probes to identify cells or tissues, particularly, neuronal cells or tissues, that exhibit dysregulation of these processes, and to identify modulators of these physiological processes for the treatment of neurological disorders.

In certain embodiments, the presently-described GPCRs can be used in the diagnosis and treatment of certain diseases or conditions, i.e., TGR-associated disorders. For example, modulators of the activity of GPCRs (e.g., TGR2, GPR77, LGR4, LGR5, LGR6, GPR40, GPR43, TGR18, or TGR164) that are expressed in a particular cell type (e.g., a peripheral neuron, immune cell, brain tissue, adipocytes, kidney cells), can be used to modulate cellular function and pathways that involve that cell type (e.g., responsiveness to extracellular signals, such as pain, or inflammatory signals; or metabolic pathways, such as lipid metabolism). Thus, modulators may be used to treat conditions or diseases with TGR2, GPR77, LGR4, LGR5, LGR6, GPR40, GPR43, TGR18, or TGR164. For example, modulators of GPR40 or GPR43 activity may be used to treat diseases associated with lipid metabolism, for example, cardiovascular disease, stroke, diabetes, obesity, etc.

Further, dysfunction in the GPCRs described herein or in the levels of the ligands that bind to the GPCRs can produce a disease, condition, or symptom associated with a lack of function of the particular cell type in which the GPCR is expressed. In certain embodiments, the presently-described GPCRs can be used in the diagnosis and treatment of certain diseases or conditions, i.e., TGR-associated disorders. For example, the activity of GPCRs that are expressed or preferentially expressed in a particular cell type (e.g., neurons), can be used to modulate cellular function (e.g., responsiveness to extracellular signals), thereby specifically modulating the function of the cells of that type in a patient. Further, mutations in the cell specific GPCRs will likely produce a disease, condition, or symptom associated with a lack of function of the particular cell type.

Similarly, mutations or dysregulation of TGRs expressed in lymphocytes or hematopoietic cell-associated TGRs, i.e., TGRs preferentially expressed in peripheral blood lymphocytes (PBLs), bone marrow, thymus, or hematopoietic cell lineages including cells involved in the immune system, can lead to malignancies, anemia, and other disorders of immune function such as autoimmune diseases (see, e.g., *Harrison's Principles of Internal Medicine*, supra). Disorders in the function, or level, of kidney-associated GPCRs will likely result in any of a number of nephrotic conditions or diseases, such as renal failure, nephritis, nephrotic syndrome, asymptomatic urinary abnormalities, renal tubule defects, hypertension, nephrolithiasis, or any other syndrome or disease associated with the kidneys (see, e.g., *Harrison's Principles of Internal Medicine,* 12th Edition, Wilson, et al., eds., McGraw-Hill, Inc.).

Mutation or dysregulation of adipocyte or liver GPCRs can lead to disorders relating to glucose metabolism, weight control and hyperlipidemia; and can also be used to detect, or diagnose a propensity for, conditions such as obesity. Similarly, spleen-associated GPCRs may be involved in any spleen-associated disorder or condition, e.g., splenic enlargement, immune disorders, blood disorders, and others (see, e.g., *Harrison's Principles of Internal Medicine*, supra). Altered function, or level, of GPCRs expressed in the colon can result in any of a number of colon-associated conditions or diseases, e.g., inflammatory bowel disease such as Crohn's disease and ulcerative colitis, and other alterations in bowel habit, rectal bleeding, pain, and other symptoms (see, e.g., *Harrison's Principles of Internal Medicine*, supra). Skeletal muscle-associated GPCRs may play a role in varioius myopathies including those that cause muscle pain; acute, subacute, or chronic muscle weakness; and other diseases of the skeletal muscle system (see, e.g., *Harrison's Principles of Internal Medicine*, supra). GPCRs expressed in the heart may play a role heart failure, ischemic heart disease, and various cardiomyopathies (see, e.g., *Harrison's Principles of Internal Medicine*, supra).

GPCRs expressed in the brain or neural tissue can play a role in any number of disorders including neurological disease and neurodegenerative diseases as well as disorders in sensory perception, e.g., pain perception (see, e.g., *Harrison's Principles of Internal Medicine*, supra). Disorders involving the brain include, but are not limited to, disorders involving neurons; disorders involving glia, such as astrocytes, oligodendrocytes, ependymal cells, and microglia; cerebrovascular diseases, such as those related to hypoxia, ischemia, and infarction; demyelinating diseases, such as multiple sclerosis; degenerative diseases, such as Alzheimer disease, Pick disease, Parkinson disease, and Huntington disease; and degenerative diseases affecting motor neurons, including amyotrophic lateral sclerosis; and various tumors involving neural tissue.

Mutation or altered activity of GPCRs preferentially expressed in the hypothalamus, will likely result in any number of conditions associated with the hypothalamus and the pituitary gland, which is often controlled by chemical mediators secreted by the hypothalamus. For example, dysfunction of hypothalamus-specific GPCRs can alter secretion of one or more hypothalamic factors such as growth hormone-releasing hormone, somatostatin, gonadotropin-releasing hormone, thyrotropin-releasing hormone, and corticotropin-releasing hormone. Thus, hypothalamic-associated diseases include hypothyroidism, hypogonadism, growth disorders, and hyperprolactinemia, as well as diabetes insipidus and disturbances of thirst, sleep, temperature regulation, appetite, blood pressure or any other syndrome or disease associated with the hypothalamus (see, e.g., *Harrison's Principles of Internal Medicine,* 12th Edition, Wilson, et al., eds., McGraw-Hill, GPCRs that are expressed in reproductive tissues, e.g., ovaries, uterus, testis, may play a role in various disorders of the reproductive system (see, e.g., *Harrison's Principles of Internal Medicine*, supra). These include, for example, disorders involving the uterus and endometrium such as endometriosis; endometrial polyps; and various uterine tumor. Disorders of the ovary include amenorrhea, ovarian failure, and chronic anovulation. Disorders of the testis include infertility and disorders relating to testosterone production.

GPCRs that are expressed in the adrenal glands may play a role in diseases related to adrenal function (see, e.g., *Harrison's Principles of Internal Medicine*, supra). These include diseases of excess adrenal function, such as Cushing's syndrome, aldosteronism, and adrenal virilism; as well as those disease of insufficient adrenal function, e.g., Addison's disease, secondary and acute adrenocortical insufficiency, and hypoaldosteronism.

GPCRs that are expressed predominantly in the kidney may play a role in various diseases of the kidney (see, e.g., *Harrison's Principles of Internal Medicine*, supra) or diseases related to kidney function including hypertension, renal inflammatory disease, e.g., glomerulonephritis, polycystic disease, and renal failure.

Accordingly, the methods of the invention can be used to diagnose any of the herein-described disorders or conditions in a patient, e.g., by examining the sequence, level, or activity of any of the present GPCRs in a patient, wherein an alteration, e.g., a decrease, in the level of expression or activity in a GPCR, or the detection of a deleterious mutation in a GPCR, indicates the presence or the likelihood of the disease or condition. Further, modulation of the present GPCRs (e.g., by administering modulators of the GPCR) can be used to treat or prevent any of the conditions or diseases.

For example, TGR2 can be involved in inflammatory disorders and disorders of the immune response. Furthermore, it can be involved in nociceptive responses. Thus TGR2 modulators, e.g., β-alanine, β-alanine analogs, other compounds that have the ability to compete with β-alanine for binding to TGR2, or compounds that otherwise modulate β-alanine binding or β-alanine-induced activity, may also be used for the treatment of immune, inflammatory or nociceptive (pain) disorders. Pain disorders include, but are not limited to, neuropathic pain resulting from injury to specific nerves; pain associated with cancer, such as pain resulting from bone metastases in cancer; pain associated with inflammatory responses or inflammatory diseases, e.g., various types of arthritis and other diseases including those listed below; and pain associated with chronic infections, such as ganglionic viral infections, e.g., Herpes infection. Acute and or/chronic pain due to injury, e.g., burns, may also be treated. Immune and inflammatory disorders include a variety of disorders, e.g., chronic or acute inflammatory syndromes, such as rheumatoid arthritis, rheumatoid spondylitis, osteoarthritis, gouty arthritis and other arthritic conditions; other autoimmune diseases, e.g., lupus erythematosus; pulmonary fibrosis; ileitis; colitis; Crohn's disease; pancreatitis, inflammatory responses or sepsis associated with infection, e.g., viral or bacterial infection; dermal inflammatory responses, e.g., psoriasis, dermatoses, scleroderma, blistering disease; nephritis; neurogenic inflammation, e.g., meningitis, septic shock, Down's syndrome, postischemic brain injury, HIV encephalopathy, Parkinson's disease, Alzheimer's disease, amyotrophic lateral sclerosis and multiple sclerosis; idiopathic inflammatory myopathies; inflammation of the blood vessels; reperfusion injury; thyroiditis; Type I diabetes; allergies; graft vs. host reaction, allograft rejections; and a variety of proliferative disorders of immune cells (see, e.g., Harrison's, supra) including, e.g., anemia, thrombocytopenia, leukopenia as well as immune malignancies such as leukemias and lymphomas.

GPR77 can be involved in disorders involving triglyceride metabolism and/or glucose metabolism. Additionally, it may also be involved in disorders of the brain, e.g., disorders of the hypothalamus or cortex. Thus, modulators of GPR77, e.g., compounds that have the ability to compete with ASP for binding to GPR77, or compounds that otherwise modulate ASP binding or ASP-induced activity, may be used to treat such disorders. These disorders include, but are not limited to, disorders of fat metabolism, obesity, diabetes, atherosclerosis, and other diseases related to triglyceride metabolism. Other disorders, such as neurological disorders and hormonal disorders, e.g., those stemming from hypothalamic dysfunction, may also be treated with compounds that modulate ASP binding to GPR77.

LGR4, LGR5, and LGR6 can be involved in disorders relating to calcium uptake, growth, reproduction, wound healing, atherogenesis, angiogenesis, neuronal differentiation, and various neurological disorders. Accordingly, modulators of these receptors, e.g., stanniocalcins or other compounds that have the ability to compete with a stanniocalcin for binding to the GPCR, or compounds that otherwise modulate stanniocalcin binding to its receptor or stanniocalcin-induced activity may be used to treat such conditions. These conditions include, but are not limited to disorders of bone growth and regeneration, e.g., osteoporosis, bone fractures, bone loss associated with periodontitis; kidney disorders; disorders of mineral metabolism; atherogenesis; angiogenesis; wound healing, conditions or diseases that relate to growth, such as delayed or excessive growth; conditions or diseases that relate to reproduction, such as infertility; neurological disorders including ischemic brain injury; and other neurological diseases such as those that involve inflammation.

Modulators of GPR40 and GPR43 may also be used for the treatment of conditions relating to fat metabolism, for example, dyslipidemia, coronary artery disease, atherosclerosis, obesity, thrombosis, angina, chronic renal failure, peripheral vascular disease, stroke, type II diabetes and metabolic syndrome (syndrome X). Further, GPR40 is expressed in the brain, in particular, in the substantia nigra and spinal cord. Thus, modulators of GPR40 that are identified as disclosed herein may be used for the treatment of other neurological diseases, as well as diseases such as ischemic brain injury, stroke.

Modulators of TGR18 and TGR164 may be used for the treatment of conditions relating to kidney dysfunction including including Bartter's syndrome, Gitelman syndrome, nephrolithiasis, renal amyloidosis, hypertension; primary aldosteronism; Addison's disease; renal failure; glomerulonephritis; chronic glomerulonephritis: tubulointerstitial nephritis; cystic disorders of the kidney and dysplastic malformations such as polycystic disease, renal dysplasias, and cortical or medullary cysts; inherited polycystic renal diseases (PRD), such as recessive and autosomal dominant PRD; medullary cystic disease; medullary sponge kidney and tubular dysplasia; Alport's syndrome; non-renal cancers which affect renal physiology, such as bronchogenic tumors of the lungs or tumors of the basal region of the brain; multiple myeloma; adenocarcinomas of the kidney; metastatic renal carcinoma; in addition, nephrotoxic disorders include any functional or morphologic change in the kidney produced by any pharmaceutical, chemical, or biological agent that is ingested, injected, inhaled, or absorbed. Some broad categories of common nephrotoxic agents are heavy metals, all classes of antibiotics, analgesics, solvents, oxalosis-inducing agents, anticancer drugs, herbicides and pesticides, botanicals and biologicals, and antiepileptics.

Administration and Pharmaceutical Compositions

Modulators of the GPCR-ligand interaction can be administered to a mammalian subject for modulation of signal transduction in vivo, e.g., for the treatment of any of the diseases or conditions described supra. As described in detail below, the modulators are administered in any suitable manner, optionally with pharmaceutically acceptable carriers.

The identified modulators can be administered to a patient at therapeutically effective doses to prevent, treat, or control diseases and disorders mediated, in whole or in part, by a GPCR-ligand interaction of the present invention. The compositions are administered to a patient in an amount sufficient to elicit an effective protective or therapeutic response in the patient. An amount adequate to accomplish this is defined as "therapeutically effective dose." The dose will be determined by the efficacy of the particular GPCR modulators employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally.

For oral administration, the pharmaceutical compositions can take the form of, for example, tablets or capsules prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

EXAMPLES

The following examples are provided by way of illustration only and not by way of limitation. Those of skill in the art will readily recognize a variety of noncritical parameters that could be changed or modified to yield essentially similar results.

Example 1

Identification of β-alanine as a Ligand for TGR2

A library of natural ligands was screened for the ability to activate TGR2. β-alanine was a positive hit at 10 μM in an Aequorin assay (see, e.g., An, et al., Proc. Natl. Acad. Sci USA 98:7576, 2001) that measures TGR2-mediated increase in intracellular calcium concentration. Addition of β-alanine at 10 μM did not activate 40 other orphan GPCRs that were tested, which suggested that β-alanine is specific for TGR2. β-alanine also activated TGR2 in an inositol phosphate accumulation assay, and also specifically activated the mouse ortholog mMrgD in an Aequorin assay. Dose-dependence analysis gave an $EC_{50}$ of 9.1 μM for β-alanine in an Aequorin assay using CHO cells transiently transfected with TGR2 (FIG. 1).

Tissue-specific expression using quantitative PCR demonstrated that TGR2 is expressed in human immune cells and tissues, e.g., T lymphocytes and thymus.

Example 2

Identification of ASP as a Natural Ligand for GPR77

GPR77 has been shown to bind to complement factors C5a and C3a. Using a competitive binding assay, ASP was also shown to bind to GPR77.

GPR77 was transiently transfected into cells. A competition assay using a membrane binding format showed that ASP competed with C5a and C3a for binding to GPR77.

Example 3

Identification of Stanniocalcins as Natural Ligands for LGR4, LGR5, and LGR6

Stanniocalcins were identified as natural ligands for LGR4, LGR5, and LGR6.

Example 4

Identification of Natural Ligands for GPR43

Figure 2:
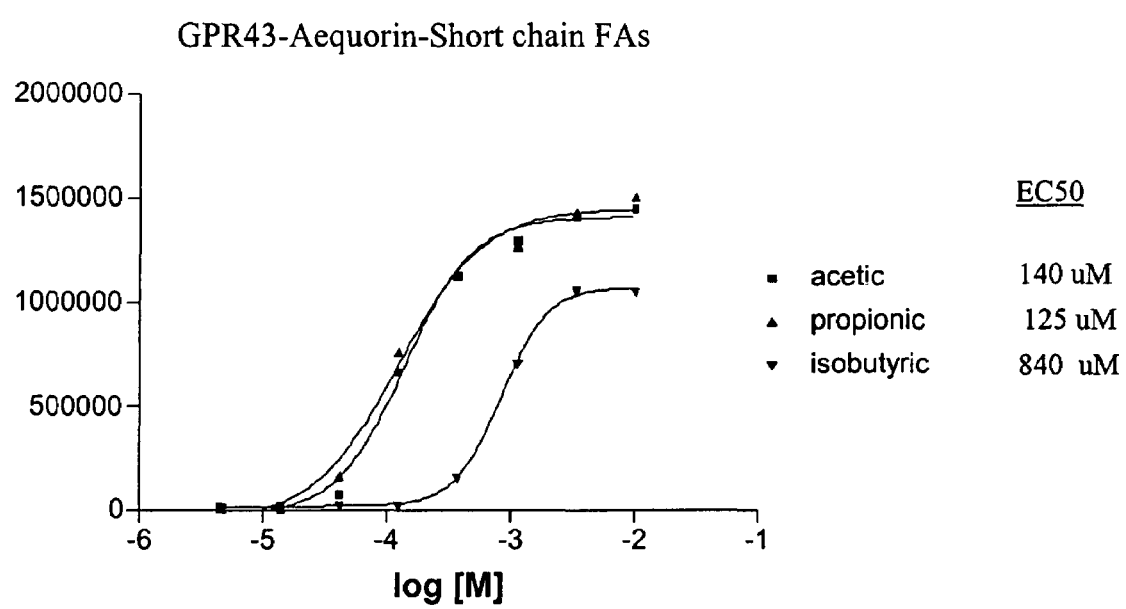
FIG. 2 provides exemplary data showing that short chain fatty acids activate GPR43.

A battery of fatty acids were tested for the ability to activate GPR43. Short chain fatty acids of 2–3 carbons in length activated GPR43. In particular, GR43 is activated by acetate and propionate at about 140 μM (FIG. 2). The medium chain fatty acids pentanoate, hexanoate, heptanoate, octanoate, and nonanoate do not activate GPR43 in this experiment.

Example 5

Identification of Natural Ligands for GPR40

Figure 4:
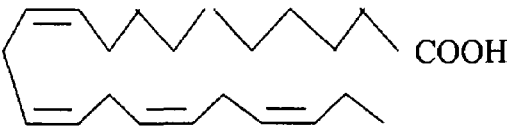
FIG. 4 provides exemplary data showing that polyunsaturated fatty acids activate GPR40.
Figure 4:
Figure 4:
Figure 4:
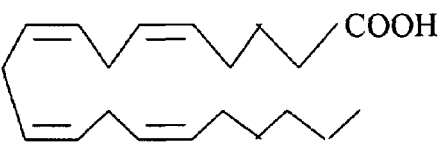
Figure 4:
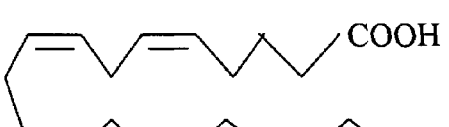
Figure 5:
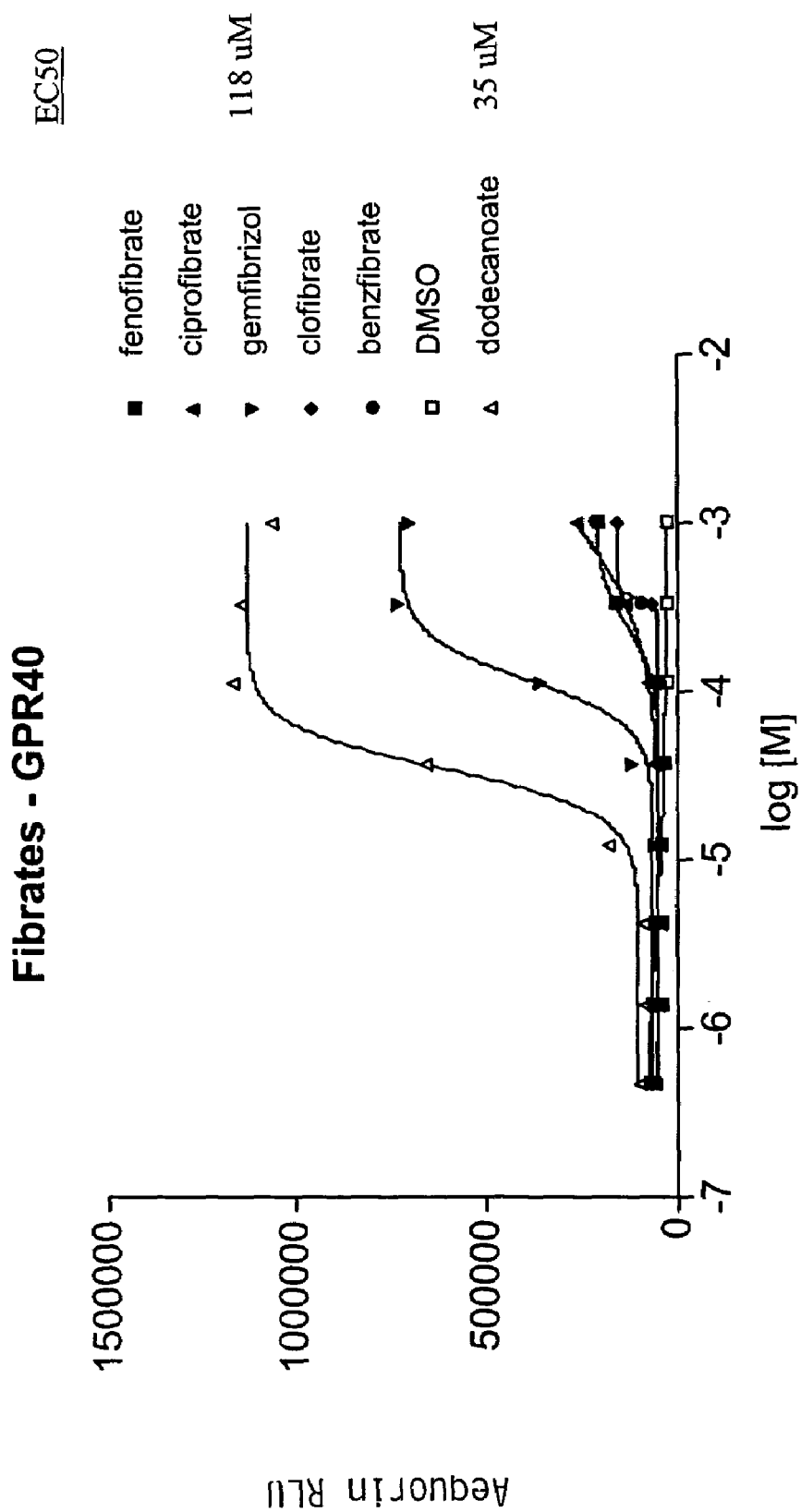
FIG. 5 provides exemplary data showing that hypolipidemic drugs and fibrates activate GPR40.

Fatty acids and other molecules were also tested for the ability to activate GPR40. The results showed that medium and long chain (6C's or longer) saturated fatty acids activate GPR40 (FIG. 3). Furthermore, polyunsaturated fatty acids activate GPR40 (FIG. 4). Additional analyses demonstrated that hypolipidemic drugs and fibrates, a class of lipid-lowerering agents also activate GPR40 (FIG. 4).

Example 6

Identification of Natural Ligands of TGR18

Succinic acid was identified as a natural ligand of TGR18. The ligand was purified from kidney as follows. During purification, activity was monitored using an Aequorin assay of CHO cells transiently transfected with TGR18.

Purification of TGR18 ligand

Porcine kidney (6 kg) tissue was homogenized and extracted in ethanol/water/acetic acid, 50/46/4, v/v/v. After centrifugation, the supernatant was filtered and lyophilized to remove ethanol and acetic acid. The lyophilized material was resuspended in 10 mM $K_2HPO_4$ pH8.0, loaded onto an XK50/20 Q sepharose anion-exchange column, and eluted with buffer A(10 mM $K_2HPO_4$ pH 8.0) followed by a linear gradient of buffer A to buffer B (50 mM $K_2HPO_4$ pH 8.0, 0.25M NaCl). Active fractions were pooled and fractionated on a Hiload 26/60 Superdex 30 size-exclusion column in Hank's buffered saline (HBSS). The active fractions were pooled, and loaded onto a Superdex peptide HR 10/30 size-exclusion column pre-equilibrated with 0.1% $TFA/H_2O$ and eluted isocratically with the same buffer. The active fractions were pooled, concentrated, injected on a ODS-AQ 4.6×250 mm column, and eluted isocratically with 0.1% $TFA/H_2O$. The active fractions were lyophilized and dissolved in $D_2O$ for NMR and Mass spectrometry analysis.

NMR and Mass Spectrometry

The final purified TGR18 ligand preparation was dissolved in $D_2O$ and the $^1H/^{13}C$ NMR spectra were recorded on a Bruker DRX700 spectrometer. A single $^1H$ signal was observed at 2.66 ppm. Two signals were observed at 31.8 ppm and 179.9 ppm in the decoupled $^{13}C$ spectrum. In the coupled $^{13}C$ spectrum, the signal at 31.8 ppm shows a triplet of triplets splitting pattern, implying two adjacent $CH_2$ groups with magnetic equivalence. The carboxyl groups were suggested to attach to the $CH_2$ groups based on the typical chemical shift at 179.9 ppm. The final structure was confirmed by comparison of NMR data from the TGR18 ligand preparation and succinic acid.

Positive ion electrospray ionization mass spectrometry was applied to analyze the final purified TGR18 ligand preparation. The mass spectrum was obtained on a HP 1100MSD spectrometer which was operated under unit mass resolution conditions across the mass range of interest. Full-scan mass spectrum covering m/z of 50–500 was acquired. The observation of the molecular ion ([M+1]+, 119.2) confirms succinic acid as the TGR18 ligand.

Aequorin Assay

Figure 6A:
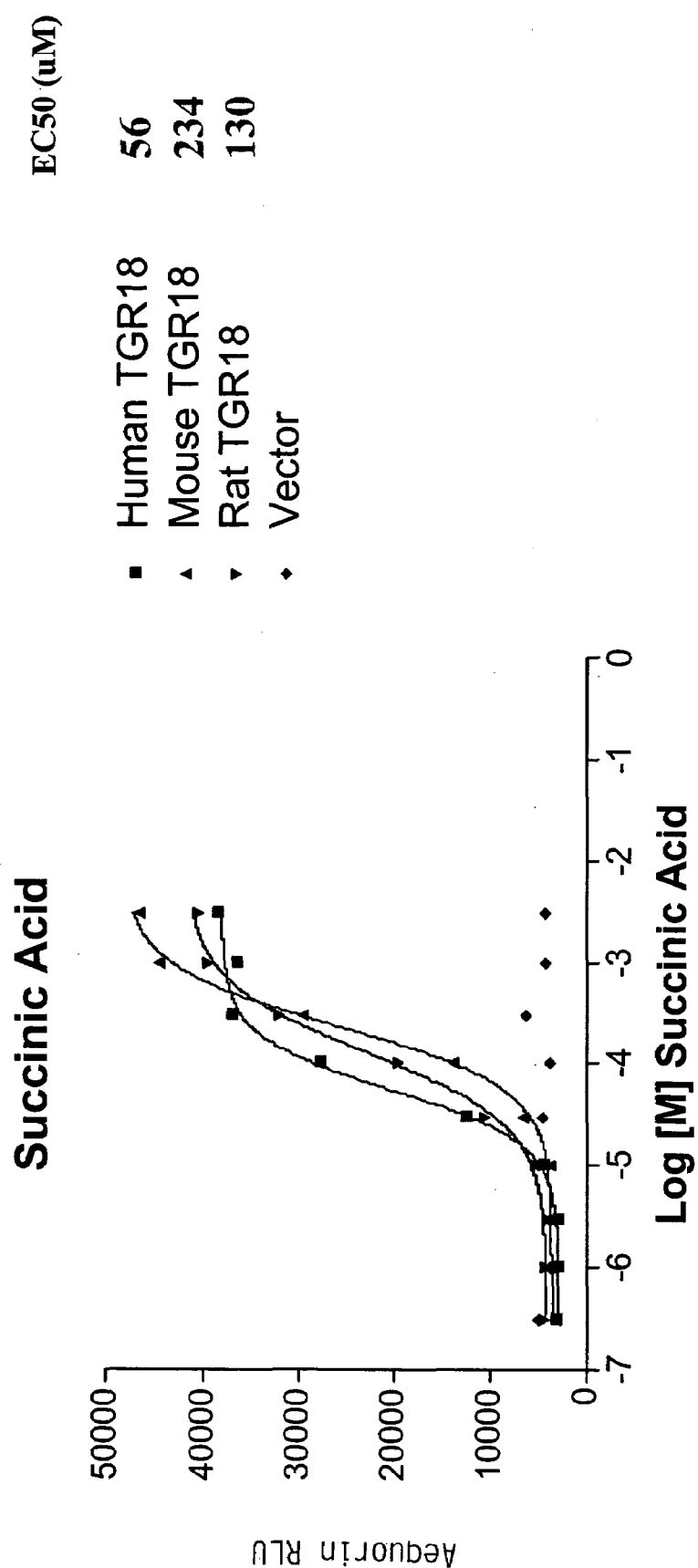
FIGS. 6A, 6B, and 6C provide exemplary data showing that succinic acid and related compounds activate TGR18.

In order to examine the ability of a compound to activate TGR18, CHO cells were transiently transfected with 10 µg of the GPCR and 10 µg Aequorin reporter gene in a 150 mm dish. As a negative control, the same amount of empty vector and the Aequorin reporter were cotransfected into CHO cells. After 24 hours, cells were harvested and resuspended in Aequorin buffer (Hank's buffered saline with 20 mM Hepes, pH7.6 and 0.1% BSA) containing 1 µg/ml coelenterazine f and incubated at room temperature for a further 2 hours. The Aequorin luminescence was recorded on Microlumat after injecting 100 µl of cells into 100 µl of ligand prepared in Aequorin buffer. The results showed that succinic acid and related compounds activated TGR18. Human, mouse, and rat TGR18 were all activated by succinic acid (FIG. 6A). In a specificity test, succinic acid at 100 µM does not activate thirty other GPCRs tested.

Fluorometric Imaging Plate Reader (FLIPR) Assay

Figure 6B:
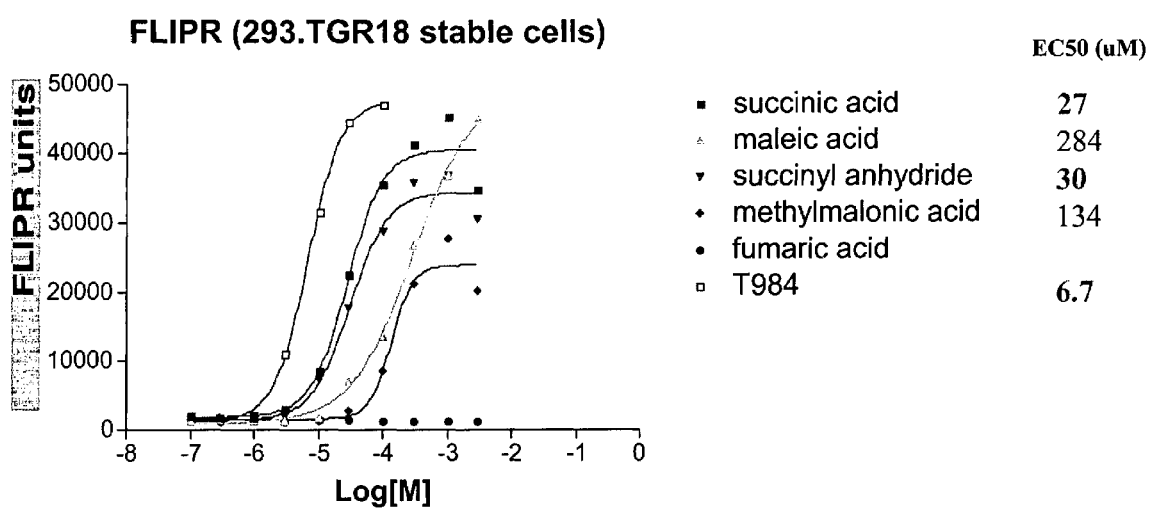
Figure 6C:
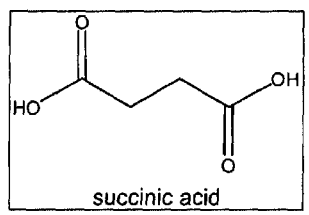
Figure 6C:
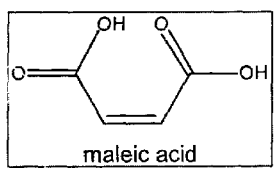
Figure 6C:
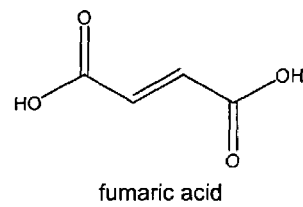
Figure 6C:
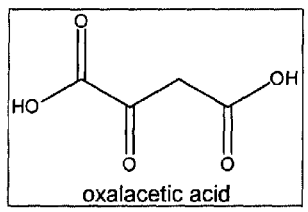
Figure 6C:
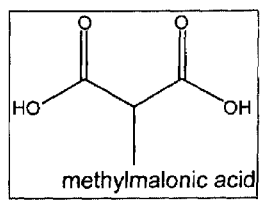
Figure 6C:
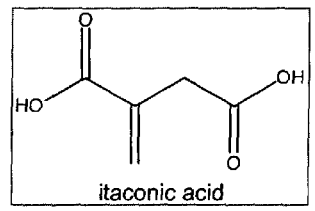
Figure 6C:
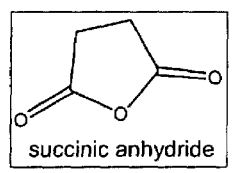
Figure 6C:
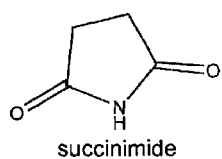
Figure 6C:
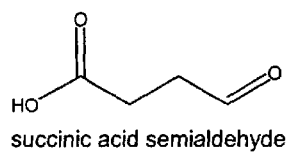

Mobilization of intracellular calcium in response to various ligands was also evaluated using a FLIPR assay. In this assay, 293 cells stably expressing TGR18 were seeded into 384-well plates and incubated at 37° C. overnight. The growth medium was then aspirated and replaced with 50 µl loading medium (FLIPR no-wash kit, Molecular Devices) and incubated at 37° C. for 1 hour. The cells were placed in a fluorometric imaging plate reader (FLIPR), and changes in cellular fluorescence were recorded after the addition of 25 µl of various ligands diluted in FLIPR buffer (FLIPR no-wash kit, Molecular Devices). The results showed that succinic acid activated TGR18 at an $EC_{50}$ of about 27 µM in the experiment presented in FIG. 6B. Analogs of succinic acid that activated TGR18 include succinic acid, maleic acid, oxalacetic acid, methylmalonic acid and itaconic acid (FIG. 6C).

Inositol Phosphate Accumulation Assay

The ability of various ligands to increase inositol phosphate was also assessed. For this analysis, 293 cells stably expression TGR18 were incubated in inositol-free DMEM/ 10% dialyzed FCS/1 µCi/ml $^3H$-inositol for 16 hours. Following incubation 10 mM LiCi was added to the cells for 15 minutes. Cells were then stimulated with various ligands for 45 minutes and extracted with ice-cold 20 mM formic acid. H3-inositol phosphate was collected on Dowex ion-exchange column (formate form) and radioactivity recorded by Topcount scintillation counter. The results showed that succinic acid increased inositol phosphate levels, whereas other dicarboxylic acids, e.g., fumaric acid, did not.

Luciferase Reporter Assay

The ability of a ligand to induce TGR18-mediated activation of a CRE-luciferase reporter was also evaluated. For this assay, 293 cells were transiently transfected with CRE-luciferase reporter, tk-renila luciferase reporter and TGR18 plasmid. Succinic acid was then added to the cell culture supernatants and incubated for a further 6 hours. The luminescence were recorded on CLIPR after cell lysis as illustrated in Dual-luciferase assay kit (Promega). The results show that succinic acid induced TGR18-induced luciferase reporter activity.

Example 7

Identification of the Natural Ligand for TGR164

Figure 7A:
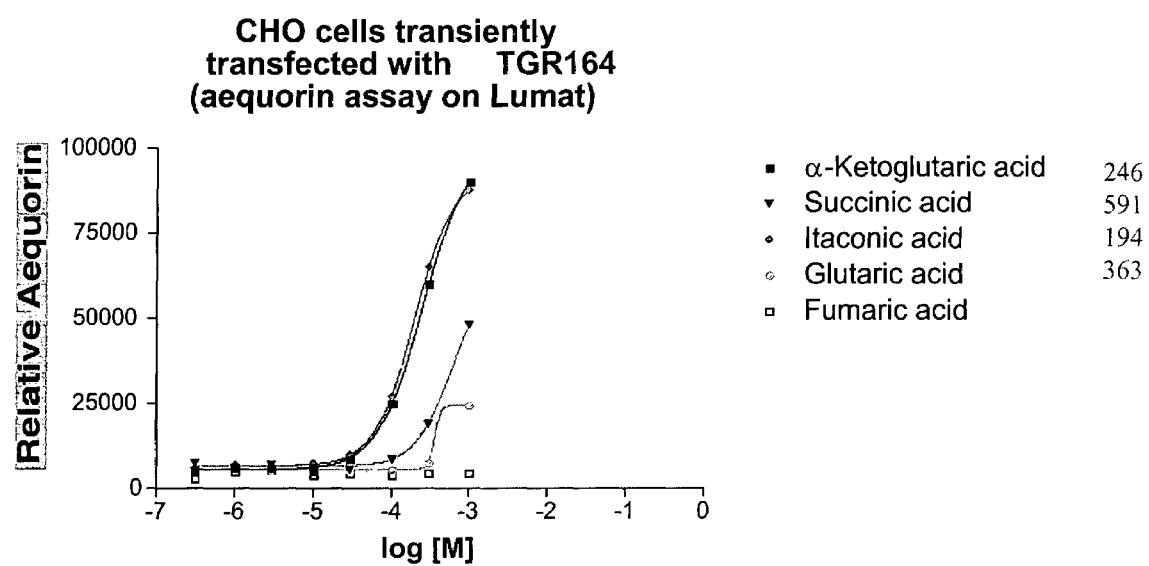
FIGS. 7A and 7B provide exemplary data showing that α-ketoglutaric acid and related compounds activate TGR164.
Figure 7B:
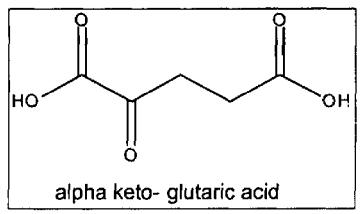
Figure 7B:
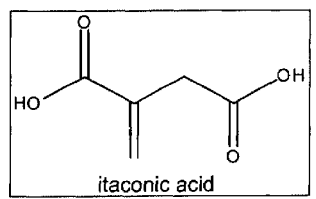
Figure 7B:
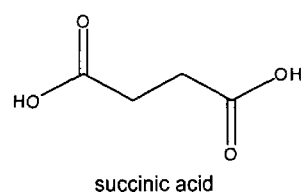
Figure 7B:
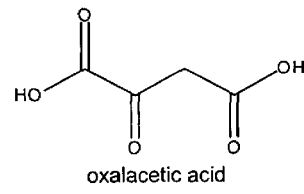
Figure 7B:
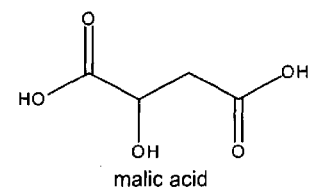
Figure 7B:
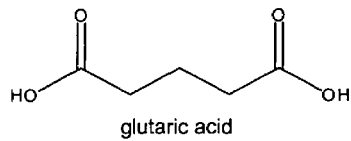

A screening of about 50 carboxylic acids using Aequorin assays, which were performed using the methodology described in Example 6, identified α-ketoglutaric acid as a TGR164 ligand Aequorin assays also showed that itaconic acid (FIGS. 7A and 7B) activated TGR164. Inositol phosphate accumulation, performed as described in Example 6, was also observed in response to α-ketoglutaric acid and itaconic acid-induced activation of TGR164.

Analysis of TGR164 activation in multiple cell lines using Aequorin assays as described in Example 6 showed that α-ketoglutaric acid activates TGR164 in various cell lines.

All publications, accession numbers, patents, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE OF GPCR NUCLEIC ACID AND PROTEIN SEQUENCES

SEQ ID NO:1 Human TGR2 Nucleic Acid
ATGAACCAGACTTTGAATAGCAGTGGGACCGTGGAGTCAGCCCTAAACTATTCCAGAGGGAGCAC

AGTGCACACGGCCTACCTGGTGCTGAGCTCCCTGGCCATGTTCACCTGCCTGTGCGGGATGGCAG

GCAACAGCATGGTGATCTGGCTGCTGGGCTTTCGAATGCACAGGAACCCCTTCTGCATCTATATC

CTCAACCTGGCGGCAGCCGACCTCCTCTTCCTCTTCAGCATGGCTTCCACGCTCAGCCTGGAAAC

CCAGCCCCTGGTCAATACCACTGACAAGGTCCACGAGCTGATGAAGAGACTGATGTACTTTGCCT

ACACAGTGGGCCTGAGCCTGCTGACGGCCATCAGCACCCAGCGCTGTCTCTCTGTCCTCTTCCCT

ATCTGGTTCAAGTGTCACCGGCCCAGGCACCTGTCAGCCTGGGTGTGTGGCCTGCTGTGGACACT

CTGTCTCCTGATGAACGGGTTGACCTCTTCCTTCTGCAGCAAGTTCTTGAAATTCAATGAAGATC

GGTGCTTCAGGGTGGACATGGTCCAGGCCGCCCTCATCATGGGGGTCTTAACCCCAGTGATGACT

CTGTCCAGCCTGACCCTCTTTGTCTGGGTGCGGAGGAGCTCCCAGCAGTGGCGGCGGCAGCCCAC

ACGGCTGTTCGTGGTGGTCCTGGCCTCTGTCCTGGTGTTCCTCATCTGTTCCCTGCCTCTGAGCA

TCTACTGGTTTGTGCTCTACTGGTTGAGCCTGCCGCCCGAGATGCAGGTCCTGTGCTTCAGCTTG

TCACGCCTCTCCTCGTCCGTAAGCAGCAGCGCCAACCCCGTCATCTACTTCCTGGTGGGCAGCCG

GAGGAGCCACAGGCTGCCCACCAGGTCCCTGGGGACTGTGCTCCAACAGGCGCTTCGCGAGGAGC

CCGAGCTGGAAGGTGGGGAGACGCCCACCGTGGGCACCAATGAGATGGGGGCT

SEQ ID NO:2 Human TGR2 Protein sequence
MNQTLNSSGTVESALNYSRGSTVHAYLVLSSLAMFTCLCGMAGNSMVIWLLGFRMHRNPFCIYI

LNLAAADLLFLFSMASTLSLETQPLVNTTDKVHELMKRLMYFAYTVGLSLLTAISTQRCLSVLFP

IWFKCHRPRHLSAWVCGLLWTLCLLMNGLTSSFCSKFLKFNEDRCFRVDMVQAALIMGVLTPVMT

LSSLTLFVWVRRSSQQWRRQPTRLFVVVLASVLVFLICSLPLSIYWFVLYWLSLPPEMQVLCFSL

SRLSSSVSSSANPVIYFLVGSRRSHRLPTRSLGTVLQQALREEPELEGGETPTVGTNEMGA

SEQ ID NO:3 Human GPR77 nucleic acid sequence
1      atggggaacgattctgtcagctacgagtatggggattacagcgacctctcggaccgccct 61     gtggactgcctggatggcgcctgcctggccatcgacccgctgcgcgtggccccgctccca 121    ctgtatgccgccatcttcctggtgggggtgccgggcaatgccatggtggcctgggtggct 181    gggaaggtggcccgccggagggtgggtgccacctggttgctccacctggccgtggcggat 241    ttgctgtgctgtttgtctctgcccatcctggcagtgcccattgcccgtggaggccactgg 301    ccgtatggtgcagtgggctgtcgggcgctgccctccatcatcctgctgaccatgtatgcc 361    agcgtcctgctcctggcagctctcagtgccgacctctgcttcctggctctcgggcctgcc 421    tggtggtctacggttcagcgggcgtgcggggtgcaggtggcctgtggggcagcctggaca 481    ctggccttgctgctcaccgtgccctcgccatctaccgccggctgcaccaggagcacttc 541    ccagcccggctgcagtgtgtggtggactacggcggctcctccagcaccgagaatgcggtg -continued

TABLE OF GPCR NUCLEIC ACID AND PROTEIN SEQUENCES

```
601  actgccatccggtttcttttttggcttcctggggcccctggtggccgtggccagctgccac
661  agtgccctcctgtgctgggcagcccgacgctgccggccgctgggcacagccattgtggtg
721  gggttttttgtctgctgggcaccctaccacctgctggggctggtgctcactgtggcggcc
781  ccgaactccgcactcctggccagggccctgcgggctgaaccctcatcgtgggccttgcc
841  ctcgctcacagctgcctcaatcccatgctcttcctgtattttgggagggctcaactccgc
901  cggtcactgccagctgcctgtcactgggccctgagggagtcccagggccaggacgaaagt
961  gtggacagcaagaaatccaccagccatgacctggtctcggagatggaggtgtag
```

SEQ ID NO:4 Human GPR77protein sequence
MGNDSVSYEYGDYSDLSDRPVDCLDGACLAIDPLRVAPLPLYAAIFLVGVPGNAMVAWVAGKVAR

RRVGATWLLHLAVADLLCCLSLPILAVPIARGGHWPYGAVGCRALPSIILLTMYASVLLLAALSA

DLCFLALGPAWWSTVQRACGVQVACGAAWTLALLLTVPSAIYRRLHQEHFPARLQCVVDYGGSSS

TENAVTAIRFLFGFLGPLVAVASCHSALLCWAARRCRPLGTAIVVGFFVCWAPYHLLGLVLTVAA

PNSALLARALRAEPLIVGLALAHSCLNPMLFLYFGRAQLRRSLPAACHWALRESQGQDESVDSKK

STSHDLVSEMEV

SEQ ID NO:5 Human LGR4 nucleic acid sequence
```
atggtg cagcagttcc ccaatcttac aggaactgtc cacctggaaa gtctgacttt gacaggtaca agataagca gcatacctaa taatttgtgt caagaacaaa agatgcttag gactttggac ttgtcttaca ataatataag agaccttcca gtttttaatg ttgccatgc tctggaagaa atttctttac agcgtaatca aatctaccaa ataaaggaag cacctttca aggcctgata tctctaagga ttctagatct gagtagaaac ctgatacatg aaattcacag tagagctttt gccacacttg gccaataac taacctagat gtaagtttca atgaattaac ttcctttcct acggaaggcc tgaatgggct aaatcaactg aaacttgtgg caacttcaa gctgaaagaa gccttagcag caaaagactt tgttaacctc aggtcttat cagtaccata tgcttatcag tgctgtgcat tttggggttg tgactcttat gcaaatttaa acacagaaga taacagcctc caggaccaca gtgtggcaca ggagaaaggt actgctgatg cagcaaatgt cacaagcact cttgaaaatg aagaacatag tcaaataatt atccattgta caccttcaac aggtgctttt aagccctgtg aatatttact gggaagctgg atgattcgtc ttactgtgtg gttcattttc ttggttgcat tattttttcaa cctgcttgtt attttaacaa catttgcatc ttgtacatca ctgccttcgt ccaaattgtt tataggcttg atttctgtgt ctaacttatt catgggaatc tatactggca tcctaacttt tcttgatgct gtgtcctggg gcagattcgc tgaatttggc atttggtggg aaactggcag tggctgcaaa gtagctgggt tccttgcagt tttctcctca gaaagtgcca tattttatt aatgctagca actgtcgaaa gaagcttatc tgcaaaagat ataatgaaaa atgggaagag caatcatctc aaacagttcc gggttgctgc ccttttggct ttcctaggtg ctacagtagc aggctgtttt cccctttttcc atagagggga atattctgca tcacccctttt gtttgccatt tcctacaggt gaaacgccat cattaggatt cactgtaacg ttagtgctat taactcact agcattttta ttaatggccg ttatctacac taaactatac tgcaacttgg aaaagagga cctctccagaa aactcacaat ctagcatgat taagcatgtc gcttggctaa tcttcaccaa ttgcatcttt ttctgccctg tggcgttttt ttcatttgca ccattgatca ctgcaatctc tatcagcccc gaaataatga agctctgttac
```

TABLE OF GPCR NUCLEIC ACID AND PROTEIN SEQUENCES

```
tctgatattt tttccattgc ctgcttgcct gaatccagtc ctgtatgttt tcttcaaccc aaagtttaaa gaagactgga agttactgaa gcgacgtgtt accaagaaaa gtggatcagt ttcagtttcc atcagtagcc aaggtggttg tctggaacag gatttctact acgactgtgg catgtactca catttgcagg gcaacctgac tgtttgcgac tgctgcgaat cgtttctttt aacaaagcca gtatcatgca aacacttgat aaaatcacac agctgtcctg cattggcagt ggcttcttgc caaagacctg agggctactg tccgactgt ggcacacagt cggcccactc tgattatgca gatgaagaag attcctttgt ctcagacagt tctgaccagg tgcaggcctg tggacgagcc tgcttctacc agagtagagg attcccttg gtgcgctatg cttacaatct accaagagtt aaagactga
```

SEQ ID NO:6 Human LGR4 protein sequence
MVQQFPNLTGTVHLESLTLTGTKISSIPNNLCQEQKMLRTLDLSYNNIRDLPSFNGCHALEEISL

QRNQIYQIKEGTFQGLISLRILDLSRNLIHEIHSRAFATLGPITNLDVSFNELTSFPTEGLNGLN

QLKLVGNFKLKEALAAKDFVNLRSLSVPYAYQCCAFWGCDSYANLNTEDNSLQDHSVAQEKGTAD

AANVTSTLENEEHSQIIIHCTPSTGAFKPCEYLLGSWMIRLTVWFIFLVALFFNLLVILTTFASC

TSLPSSKLFIGLISVSNLFMGIYTGILTFLDAVSWGRFAEFGIWWETGSGCKVAGFLAVFSSESA

IFLLMLATVERSLSAKDIMKNGKSNHLKQFRVAALLAFLGATVAGCFPLFHRGEYSASPLCLPFP

TGETPSLGFTVTLVLLNSLAFLLMAVIYTKLYCNLEKEDLSENSQSSMIKHVAWLIFTNCIFFCP

VAFFSFAPLITAISISPEIMKSVTLIFFPLPACLNPVLYVFFNPKFKEDWKLLKRRVTKKSGSVS

VSISSQGGCLEQDFYYDCGMYSHLQGNLTVCDCCESFLLTKPVSCKHLIKSHSCPALAVASCQRP

EGYWSDCGTQSAHSDYADEEDSFVSDSSDQVQACGRACFYQSRGFPLVRYAYNLPRVKD

SEQ ID NO:7 Human LGR5 nucleic acid sequence
```
   1 atggacacctcccggctcggtgtgctcctgtccttgcctgtgctgctgcagctggcgacc
  61 gggggcagctctcccaggtctggtgtgttgctgagggctgccccacacactgtcattgc
 121 gagcccgacggcaggatgttgctcagggtggactgctccgacctggggctctcggagctg
 181 ccttccaacctcagcgtcttcacctcctacctagacctcagtatgaacaacatcagtcag
 241 ctgctcccgaatcccctgcccagtctccgcttcctggaggagttacgtcttgcgggaaac
 301 gctctgacatacattcccaagggagcattcactggccttacagtcttaaagttcttatg
 361 ctgcagaataatcagctaagacacgtacccacagaagctctgcagaatttgcgaagcctt
 421 caatccctgcgtctggatgctaaccacatcagctatgtgccccaagctgtttcagtggc
 481 ctgcattccctgaggcacctgtggctggatgacaatgcgttaacagaaatccccgtccag
 541 gcttttagaagtttatcggcattgcaagccatgaccttggccctgaacaaaatacaccac
 601 ataccagactatgcctttggaaacctctccagcttggtagttctacatctccataacaat
 661 agaatccactccctgggaaagaaatgctttgatgggctccacagcctagagactttagat
 721 ttaaattacaataaccttgatgaattccccactgcaattaggacactctccaaccttaaa
 781 gaactaggatttcatagcaacaatatcaggtcgatacctgagaaagcatttgtaggcaac
 841 ccttctcttattacaatacatttctatgacaatcccatccaatttgttgggagatctgct
 901 tttcaacatttacctgaactaagaacactgactctgaatggtgcctcacaaataactgaa
 961 tttcctgatttaactggaactgcaaacctggagagtctgactttaactggagcacagatc
1021 tcatctcttcctcaaaccgtctgcaatcagttacctaatctccaagtgctagatctgtct
1081 tacaacctattagaagatttacccagttttttcagtctgccaaaagcttcagaaaattgac
```

-continued

TABLE OF GPCR NUCLEIC ACID AND PROTEIN SEQUENCES

```
1141 ctaagacataatgaaatctacgaaattaaagttgacactttccagcagttgcttagcctc
1201 gcatcgctgaatttggcttggaacaaaattgctattattcaccccaatgcattttccact
1261 ttgccatccctaataaagctggacctatcgtccaacctcctgtcgtcttttcctataact
1321 gggttacatggtttaactcacttaaaattaacaggaaatcatgccttacagagcttgata
1381 tcatctgaaaactttccagaactcaaggttatagaaatgccttatgcttaccagtgctgt
1441 gcatttggagtgtgtgagaatgcctataagatttctaatcaatggaataaaggtgacaac
1501 agcagtatgacgaccttcataagaaagatgctggaatgtttcaggctcaagatgaacgt
1561 gaccttgaagatttcctgcttgactttgaggaagacctgaaaccctt cattcagtgcag
1621 tgttcaccttccccaggccccttcaaaccctgtgaacacctgcttgatggctggctgatc
1681 agaattggagtgtggaccatagcagttctggcacttacttgtaatgctttggtgacttca
1741 acagttttcagatccctctgtacatttcccccattaaactgttaattggggtcatcgca
1801 gcagtgaacatgctcacgggagtctccagtgccgtgctggctggtgtggatgcgttcact
1861 tttggcagctttgcacgacatggtgcctggtgggagaatgggggttggttgccatgtcatt
1921 ggttttttgtccattttgcttcagaatcatctgttttcctgcttactctggcagccctg
1981 gagcgtgggttctctgtgaaatattctgcaaaatttgaaacgaaagctccatttctagc
2041 ctgaaagtaatcattttgctctgtgccctgctggccttgaccatggccgcagttcccctg
2101 ctgggtggcagcaagtatggcgcctccctctctgcctgcctttgccttttggggagccc
2161 agcaccatgggctacatggtcgctctcatcttgctcaattcccttgcttcctcatgatg
2221 accattgcctacaccaagctctactgcaatttggacaagggagacctggagaatatttgg
2281 gactgctctatggtaaaacacattgccctgttgctcttcaccaactgcatcctaaactgc
2341 cctgtggctttcttgtccttctcctcttaataaaccttacatttatcagtcctgaagta
2401 attaagtttatccttctggtggtagtcccacttcctgcatgtctcaatcccttctctac
2461 atcttgttcaatcctcactttaaggaggatctggtgagcctgagaaagcaaacctacgtc
2521 tggacaagatcaaaacacccaagcttgatgtcaattaactctgatgatgtcgaaaaacag
2581 tcctgtgactcaactcaagccttggtaaccttaccagctccagcatcacttatgacctg
2641 cctcccagttccgtgccatcaccagcttatccagtgactgagagctgccatctttcctct
2701 gtggcatttgtcccatgtctctaa
```

SEQ ID NO:8 Human LGR5 protein sequence
MDTSRLGVLLSLPVLLQLATGGSSPRSGVLLRGCPTHCHCEPDG

RMLLRVDCSDLGLSELPSNLSVFTSYLDLSMNNISQLLPNPLPSLRFLEELRLAGNAL

TYIPKGAFTGLYSLKVLMLQNNQLRHVPTEALQNLRSLQSLRLDANHISYVPPSCFSG

LHSLRHLWLDDNALTEIPVQAFRSLSALQAMTLALNKIHHIPDYAFGNLSSLVVLHLH

NNRIHSLGKKCFDGLHSLETLDLNYNNLDEFPTAIRTLSNLKELGFHSNNIRSIPEKA

FVGNPSLITIHFYDNPIQFVGRSAFQHLPELRTLTLNGASQITEFPDLTGTANLESLT

LTGAQISSLPQTVCNQLPNLQVLDLSYNLLEDLPSFSVCQKLQKIDLRHNEIYEIKVD

TFQQLLSLRSLNLAWNKIAIIHPNAFSTLPSLIKLDLSSNLLSSFPITGLHGLTHLKL

TGNHALQSLISSENFPELKVIEMPYAYQCCAFGVCENAYKISNQWNKGDNSSMDDLHK

KDAGMFQAQDERDLEDFLLDFEEDLKALHSVQCSPSPGPFKPCEHLLDGWLIRIGVWT

IAVLALTCNALVTSTVFRSPLYISPIKLLIGVIAALVNMLTGVSSAVLAGVDAFTFGSF

-continued

TABLE OF GPCR NUCLEIC ACID AND PROTEIN SEQUENCES

ARHGAWWENGVGCHVIGFLSIFASESSVFLLTLAALERGFSVKYSAKFETKAPFSSLK

VIILLCALLALTMAAVPLLGGSKYGASPLCLPLPFGEPSTMGYMVALILLNSLCFLMM

TIAYTKLYCNLDKGDLENIWDCSMVKHIALLLFTNCILNCPVAFLSFSSLINLTFISP

EVIKFILLVVVPLPACLNPLLYILFNPHFKEDLVSLRKQTYVWTRSKHPSLMSINSDD

VEKQSCDSTQALVTFTSSSITYDLPPSSVPSPAYPVTESCHLSSVAFVPCL

SEQ ID NO:9 Human LGR6 nucleic acid sequence
```
   1 atgcgcttggagggagagggccgctcagcgagggcgggacagaatctctcccgggctggg
  61 agtgcacggcgcggtgcgcccagggacctcagcatgaacaacctcacagagcttcagcct
 121 ggcctcttccaccacctgcgcttcttggaggagctgcgtctctctgggaaccatctctca
 181 cacatcccaggacaagcattctctggtctctacagcctgaaaatcctgatgctgcagaac
 241 aatcagctggaggaatccccgcagaggcgctgtgggagctgccgagcctgcagtcgcta
 301 gacctgaattataacaagctgcaggagttccctgtggccatccggaccctgggcagactg
 361 caggaactggggttccataacaacaacatcaaggccatcccagaaaaggccttcatgggg
 421 aaccctctgctacagacgatacactttatgataacccaatccagtttgtgggaagatcg
 481 gcattccagtacctgcctaaactccacacactatctctgaatggtgccatggacatccag
 541 gagtttccagatctcaaaggcaccaccagcctggagatcctgaccctgacccgcgcaggc
 601 atccggctgctcccatcggggatgtgccaacagctgcccaggctccgagtcctggaactg
 661 tctcacaatcaaattgaggagctgcccagcctgcacaggtgtcagaaattggaggaaatc
 721 ggcctccaacacaaccgcatctgggaaattggagctgacaccttcagccagctgagctcc
 781 ctgcaagccctggatcttagctggaacgccatccggtccatccaccccgaggccttctcc
 841 accctgcactccctggtcaagctggacctgacagacaaccagctgaccacactgcccctg
 901 gctggacttggggcttgatgcatctgaagctcaaagggaaccttgctctctcccaggcc
 961 ttctccaaggacagtttcccaaaactgaggatcctggaggtgccttatgcctaccagtgc
1021 tgtccctatgggatgtgtgccagcttcttcaaggcctctgggcagtgggaggctgaagac
1081 cttcaccttgatgatgaggagtcttcaaaaaggcccctgggcctccttgccagacaagca
1141 gagaaccactatgaccaggacctggatgagctccagctggagatggaggactcaaagcca
1201 caccccagtgtccagtgtagccctactccaggccccttcaagccctgtgagtacctcttt
1261 gaaagctggggcatccgcctggccgtgtgggccatcgtgttgctctccgtgctctgcaat
1321 ggactggtgctgctgaccgtgttcgctggcgggcctgtcccctgccccggtcaagttt
1381 gtggtaggtgcgattgcaggcgccaacaccttgactggcatttcctgtggccttctagcc
1441 tcagtcgatgccctgacctttggtcagttctctgagtacggagcccgctgggagacgggg
1501 ctaggctgccgggccactggcttcctggcagtacttgggtcggaggcatcggtgctgctg
1561 ctcactctggccgcagtgcagtgcagcgtctccgtctcctgtgtccgggcctatgggaag
1621 tccccctccctgggcagcgttcgagcagggtcctaggctgcctggcactggcagggctg
1681 gccgccgcactgcccctggcctcagtgggagaatacggggcctcccactctgcctgccc
1741 tacgcgccacctgagggtcagccagcagccctgggcttcaccgtggccctggtgatgatg
1801 aactccttctgtttcctggtcgtggccggtgcctacatcaaactgtactgtgacctgccg
1861 cggggcgactttgaggccgtgtgggactgcgccatggtgaggcacgtggcctggctcatc
1921 ttcgcagacgggctcctctactgtcccgtggccttcctcagcttcgcctccatgctgggc
```

TABLE OF GPCR NUCLEIC ACID AND PROTEIN SEQUENCES 1981 ctcttccctgtcacgcccgaggccgtcaagtctgtcctgctggtggtgctgcccctgcct 2041 gcctgcctcaacccactgctgtacctgctcttcaaccccacttccgggatgaccttcgg 2101 cggcttcggccccgcgcaggggactcagggcccctagcctatgctgcggccggggagctg 2161 gagaagagctcctgtgattctacccaggccctggtagccttctctgatgtggatctcatt 2221 ctggaagcttctgaagctgggcggccccctgggctggagacctatggcttcccctcagt 2281 accctcatctcctgtcagcagccaggggcccccaggctggagggcagccattgtgtagag 2341 ccagaggggaaccactttgggaaccccaaccctccatggatggagaactgctgctgagg 2401 gcagagggatctacgccagcaggtggaggcttgtcaggggtggcggcttt cagccctct 2461 ggcttggccttgcttcacacgtat SEQ ID NO:10 Human LGR6 protein sequence
MRLEGEGRSARAGQNLSRAGSARRGAPRDLSMNLTELQPGLFH

HLRFLEELRLSGNLSHIPGQAFSGLYSLKILMLQNNQLGGIPAEALWELPSLQSLDL

NYNKLQEFPVAIRTLGRLQELGFHNNNIKAIPEKAFMGNPLLQTIHFYDNPIQFVGRS

AFQYLPKLHTLSLNGAMDIQEFPDLKGTTSLEILTLTRGIRLLPSGMCQQLPRLRVL

ELSHNQIEELPSLHRCQKLEEIGLQHNRIWEIGADTFSQLSSLQALDLSWNAIRSIHP

EAFSTLHSLVKLDLTDNQLTTLPLAGLGGLMHLKLKGNLALSQAFSKDSFPKLRILEV

PYAYQCCPYGMCASFFKASGQWEAEDLHLDDEESSKRPLGLLARQAENHYDQDLDELQ

LEMEDSKPHPSVQCSPTPGPFKPCEYLFESWGIRLAVWAIVLLSVLCNGLVLLTVFAG

GPVPLPPVKFVVGAIAGANTLTGISCGLLASVDALTFGQFSEYGARWETGLGCRATGF

LAVLGSEASVLLLTLAAVQCSVSVSCVRAYGKSPSLGSVRAGVLGCLALAGLAAALPL

ASVGEYGASPLCLPYAPPEGQPAALGFTVALVMMNSFCFLVVAGAYIKLYCDLPRGDF

EAVWDCAMVRHVAWLIFADGLLYCPVAFLSFASMLGLFPVTPEAVKSVLLVVLPLPAC

LNPLLYLLFNPHFRDDLRRLRPRAGDSGPLAYAAAGELEKSSCDSTQALVAFSDVDLI

LEASEAGRPPGLETYGFPSVTLISCQQPGAPRLEGSHCVEPEGNHFGNPQPSMDGELL

LRAEGSTPAGGGLSGGGGFQPSGLALLHTY

SEQ ID NO:11 human GPR40 nucleic acid sequence
atggacctgc cccgcagct ctccttcggc ctctatgtgg ccgcctttgc gctgggcttc  61
ccgctcaacg tcctggccat ccgaggcgcg acggcccacg cccggctccg tctcaccct  121 agcctggtct acgccctgaa cctgggctgc tccgacctgc tgctgacagt ctctctgccc  181
ctgaaggcgg tggaggcgct agcctccggg gcctggccctc tgccggcctc gctgtgcccc  241
gtcttcgcgt ggcccactt cttcccactc tatgccggcg gggcttcct ggccgccctg  301 agtgcaggcc gctacctggg agcagccttc cccttgggct accaagcctt ccggaggccg  361
tgctattcct gggggggtgtg cgcggccatc tgggccctcg tcctgtgtca cctgggtctg  421
gtctttgggt tggaggctcc aggaggctgg ctggaccaca gcaacacctc cctgggcatc  481
aacacaccgg tcaacggctc tccggtctgc ctggaggcct gggaccccgc ctctgccggc  541
ccggcccgct tcagcctctc tctcctgctc ttttttctgc ccttggccat cacagccttc  601
tgctacgtgg gctgcctccg ggcactggcc cgctccggcc tgacgcacag gcggaagctg  661
cgggccgcct gggtggccgg cgggccctc ctcacgctgc tgctctgcgt aggaccctac  721
aacgcctcca cgtggccag cttcctgtac cccaatctag aggctcctg gcggaagctg  781 gggctcatca cgggtgcctg gagtgtggtg cttaatccgc tggtgaccgg ttacttggga  841

TABLE OF GPCR NUCLEIC ACID AND PROTEIN SEQUENCES agggtcctg gcctgaagac agtgtgtgcg gcaagaacgc aagggggcaa gtcccagaag 901 taa

SEQ ID NO:12 human GPR40 amino acid sequence
MDLPPQLSFGLYVAAFALGFPLNVLAIRGATAHARLRLTPSLVYALNLGCSDLLLTVSLPLKAVEALASGAW

PLPASLCPVFAVAHFFPLYAGGGFLAALSAGRYLGAAFPLGYQAFRRPCYSWGVCAAIWALVLCHLGLVFGL

EAPGGWLDHSNTSLGINTPVNGSPVCLEAWDPASAGPARFSLSLLLFFLPLAITAFCYVGCLRALARSGLTH

RRKLRAAWVAGGALLTLLLCVGPYNASNVASFLYPNLGGSWRKLGLITGAWSVVLNPLVTGYLRGRPGLKTV

CAARTQGGKSQK

SEQ ID NO:13 human GPR43 nucleic acid sequence
atgctgccgg actggaagag ctccttgatc ctcatggctt acatcatcat cttcctcact ggcctccctg ccaacctcct ggccctgcgg gcctttgtgg ggcggatccg ccagccccag cctgcacctg tgcacatcct cctgctgagc ctgacgctgg ccgacctcct cctgctgctg ctgctgccct tcaagatcat cgaggctgcg tcgaacttcc gctggtacct gcccaaggtc gtctgcgccc tcacgagttt tggcttctac agcagcatct actgcagcac gtggctcctg gcgggcatca gcatcgagcg ctacctggga gtggctttcc ccgtgcagta caagctctcc cgccggcctc tgtatggagt gattgcagct ctggtggcct gggttatgtc ctttggtcac tgcaccatcg tgatcatcgt tcaatacttg aacacgactg agcaggtcag aagtggcaat gaaattacct gctacgagaa cttcaccgat aaccagttgg acgtggtgct gcccgtgcgg ctggagctgt gcctggtgct cttcttcatc cccatggcag tcaccatctt ctgctactgg cgttttgtgt ggatcatgct ctcccagccc cttgtggggg cccagaggcg gcgccgagcc gtggggctgg ctgtggtgac gctgctcaat ttcctggtgt gcttcggacc ttacaacgtg tcccacctgg tggggtatca ccagagaaaa agccctggt ggcggtcaat agccgtggtg ttcagttcac tcaacgccag tctggacccc ctgctcttct atttctcttc ttcagtggtg cgcagggcat ttgggagagg gctgcaggtg ctgcggaatc agggctcctc cctgttggga cgcagaggca agacacagc agaggggaca atgaggaca ggggtgtggg tcaaggagaa gggatgccaa gttcggactt cactacagag tag SEQ ID NO:14 human GPR43 amino acid sequence
MLPDWKSSLILMAYIIIFLTGLPANLLALRAFVGRIRQPQPAPVHILLLSLTLADLLLLLLLPFKIIEAASN

FRWYLPKVVCALTSFGFYSSIYCSTWLLAGISIERYLGVAFPVQYKLSRRPLYGVIAALVAWVMSFGHCTIV

IIVQYLNTTEQVRSGNEITCYENFTDNQLDVVLPVRLELCLVLFFIPMAVTIFCYWRFVWIMLSQPLVGAQR

RRRAVGLAVVTLLNFLVCFGPYNVSHLVGYHQRKSPWWRSIAVVFSSLNASLDPLLFYFSSSVVRRAFGRGL

QVLRNQGSSLLGRRGKDTAEGTNEDRGVGQGEGMPSSDFTTE

SEQ ID NO:15 human TGR18 nucleic acid sequence
ATGATGGCAGAACCATTTACTGAAATTGGTGGATATGCTGCAGGCTTGGCATGGAATGCAACTTG

CAAAAACTGGCTGGCAGCAGAGGCTGCCCTGGAAAAGTACTACCTTTCCATTTTTTATGGGATTG

AGTTCGTTGTGGGAGTCCTTGGAAATACCATTGTTGTTTACGGCTACATCTTCTCTCTGAAGAAC

TGGAACAGCAGTAATATTTATCTCTTTAACCTCTCTGTCTCTGACTTAGCTTTTCTGTGCACCCT

CCCCATGCTGATAAGGAGTTATGCCAATGGAAACTGGATATATGGAGACGTGCTCTGCATAAGCA

ACCGATATGTGCTTCATGCCAACCTCTATACCAGCATTCTCTTTCTCACTTTTATCAGCATAGAT

CGATACTTGATAATTAAGTATCCTTTCCGAGAACACCTTCTGCAAAAGAAAGAGTTTGCTATTTT

-continued

TABLE OF GPCR NUCLEIC ACID AND PROTEIN SEQUENCES

AATCTCCTTGGCCATTTGGGTTTTAGTAACCTTAGAGTTACTACCCATACTTCCCCTTATAAATC

CTGTTATAACTGACAATGGCACCACCTGTAATGATTTTGCAAGTTCTGGAGACCCCAACTACAAC

CTCATTTACAGCATGTGTCTAACACTGTTGGGGTTCCTTATTCCTCTTTTTGTGATGTGTTTCTT

TTATTACAAGATTGCTCTCTTCCTAAAGCAGAGGAATAGGCAGGTTGCTACTGCTCTGCCCCTTG

AAAAGCCTCTCAACTTGGTCATCATGGCAGTGGTAATCTTCTCTGTGCTTTTTACACCCTATCAC

GTCATGCGGAATGTGAGGATCGCTTCACGCCTGGGGAGTTGGAAGCAGTATCAGTGCACTCAGGT

CGTCATCAACTCCTTTTACATTGTGACACGGCCTTTGGCCTTTCTGAACAGTGTCATCAACCCTG

TCTTCTATTTTCTTTTGGGAGATCACTTCAGGGACATGCTGATGAATCAACTGAGACACAACTTC

AAATCCCTTACATCCTTTAGCAGATGGGCTCATGAACTCCTACTTTCATTCAGAGAAAAGTGA

SEQ ID NO:16 human TGR18 amino acid sequence
MMAEPFTEIGGYAAGLAWNATCKNWLAAEAALEKYYLSIFYGIEFVVGVLGNTI

VVYGYIFSLKNWNSSNIYLFNLSVSDLAFLCTLPMLIRSYANGNWIYGDVLCISNR

YVLHANLYTSILFLTFISIDRYLIIKYPFREHLLQKKEFAILISLAIWVLVTLELLPILP

LINPVITDNGTTCNDFASSGDPNYNLIYSMCLTLLGFLIPLFVMCFFYYKIALFLKQ

RNRQVATALPLEKPLNLVIMAVVIFSVLFTPYHVMRNVRIASRLGSWKQYQCTQ

VVINSFYIVTRPLAFLNSVINPVFYFLLGDHFRDMLMNQLRHNFKSLTSFSRWAH

ELLLSFREK

SEQ ID NO:17 human TGR164 nucleic acid sequence
ATGAATGAGCCACTAGACTATTTAGCAAATGCTTCTGATTTCCCCGATTATGCAGCTGCTTTTGG

AAATTGCACTGATGAAAACATCCCACTCAAGATGCACTACCTCCCTGTTATTTATGGCATTATCT

TCCTCGTGGGATTTCCAGGCAATGCAGTAGTGATATCCACTTACATTTTCAAAATGAGACCTTGG

AAGAGCAGCACCATCATTATGCTGAACCTGGCCTGCACAGATCTGCTGTATCTGACCAGCCTCCC

CTTCCTGATTCACTACTATGCCAGTGGGCGAAAACTGGATCTTTGGAGATTTCATGTGTAAGTTTA

TCCGCTTCAGCTTCCATTTCAACCTGTATAGCAGCATCCTCTTCCTCACCTGTTTCAGCATCTTC

CGCTACTGTGTGATCATTCACCCAATGAGCTGCTTTTCCATTCACAAAACTCGATGTGCAGTTGT

AGCCTGTGCTGTGGTGTGGATCATTTCACTGGTAGCTGTCATTCCGATGACCTTCTTGATCACAT

CAACCAACAGGACCAACAGATCAGCCTGTCTCGACCTCACCAGTTCGGATGAACTCAATACTATT

AAGTGGTACAACCTGATTTTGACTGCAACTACTTTCTGCCTCCCCTTGGTGATAGTGACACTTTG

CTATACCACGATTATCCACACTCTGACCCATGGACTGCAAACTGACAGCTGCCTTAAGCAGAAAG

CACGAAGGCTAACCATTCTGCTACTCCTTGCATTTTACGTATGTTTTTTACCCTTCCATATCTTG

AGGGTCATTCGGATCGAATCTCGCCTGCTTTCAATCAGTTGTTCCATTGAGAATCAGATCCATGA

AGCTTACATCGTTTCTAGACCATTAGCTGCTCTGAACACCTTTGGTAACCTGTTACTATATGTGG

TGGTCAGCGACAACTTTCAGCAGGCTGTCTGCTCAACAGTGAGATGCAAAGTAAGCGGGAACCTT

GAGCAAGCAAAGAAAATTAGTTACTCAAACAACCCTTGA

SEQ ID NO:18 human TGR164 amino acid sequence
MNEPLDYLANASDFPDYAAAFGNCTDENIPLKMHYLPVIYGIIFLVGFPGNAVVIS

TYIFKMRPWKSSTIIMLNLACTDLLYLTSLPFLIHYYASGENWIFGDFMCKFIRFSF

HFNLYSSILFLTCFSIFRYCVIIHPMSCFSIHKTRCAVVACAVVWIISLVAVIPMTFLI

-continued

TABLE OF GPCR NUCLEIC ACID AND PROTEIN SEQUENCES

TSTNRTNRSACLDLTSSDELNTIKWYNLILTATTFCLPLVIVTLCYTTIIHTLTHGL

QTDSCLKQKARRLTILLLLAFYVCFLPFHILRVIRIESRLLSISCSIENQIHEAYIVSR

PLAALNTFGNLLLYVVVSDNFQQAVCSTVRCKVSGNLEQAKKISYSNNP

What is claimed is:

1. A method of identifying a modulator of a TGR18 polypeptide, wherein the TGR18 polypeptide has G-protein coupled receptor activity and is activated by succinic acid, the method comprising:

contacting a TGR18 polypeptide that comprises the amino acid sequence of SEQ ID NO:16 with a candidate modulator compound and succinic acid; and determining the level of activity of the polypeptide in comparison to the level of activity of the polypeptide in the absence of succinic acid.

2. The method of claim 1, wherein the step of determining the level of activity comprises a competitive assay.

3. The method of claim 1, wherein the compound is contacted with the polypeptide before the succinic acid is contacted with the polypeptide.

4. The method of claim 1, wherein the step of determining the level of activity comprises a binding assay.

5. The method of claim 1, wherein the polypeptide is recombinant.

* * * * *